(12) United States Patent
Doty

(10) Patent No.: US 7,927,375 B2
(45) Date of Patent: Apr. 19, 2011

(54) DYNAMIC SIX-DEGREES-OF-FREEDOM INTERVERTEBRAL SPINAL DISC PROSTHESIS

(76) Inventor: Keith L. Doty, Gainesville, FL (US)

( * ) Notice: Subject to any disclaimer, the term of this patent is extended or adjusted under 35 U.S.C. 154(b) by 357 days.

(21) Appl. No.: 12/209,363

(22) Filed: Sep. 12, 2008

(65) Prior Publication Data
US 2010/0070033 A1    Mar. 18, 2010

(51) Int. Cl.
*A61F 2/44* (2006.01)
(52) U.S. Cl. .............. 623/17.16; 623/17.12; 623/17.13
(58) Field of Classification Search ..... 623/17.11–17.16
See application file for complete search history.

(56) References Cited

U.S. PATENT DOCUMENTS

| | | | |
|---|---|---|---|
| 4,309,777 A | 1/1982 | Patil | |
| 4,759,766 A | 7/1988 | Buettner-Janz et al. | |
| 5,258,031 A | 11/1993 | Salib et al. | |
| 5,258,043 A | 11/1993 | Stone | |
| 5,314,477 A | 5/1994 | Marnay | |
| 5,320,644 A | 6/1994 | Baumgartner | |
| 5,401,269 A | 3/1995 | Buttner-Janz et al. | |
| 5,425,773 A | 6/1995 | Boyd et al. | |
| 5,458,642 A | 10/1995 | Beer et al. | |
| 5,674,296 A | 10/1997 | Bryan et al. | |
| 5,676,701 A | 10/1997 | Yuan et al. | |
| 5,782,832 A | 7/1998 | Larsen et al. | |
| 5,827,328 A | 10/1998 | Buttermann | |
| 5,865,846 A | 2/1999 | Bryan et al. | |
| 6,001,130 A | 12/1999 | Bryan et al. | |
| 6,019,792 A | 2/2000 | Cauthen | |
| 6,136,031 A | 10/2000 | Middleton | |
| 6,156,067 A | 12/2000 | Bryan et al. | |
| 6,179,874 B1 | 1/2001 | Cauthen | |
| 6,296,664 B1 | 10/2001 | Middleton | |

(Continued)

FOREIGN PATENT DOCUMENTS
EP     1 572 038     9/2005
(Continued)

OTHER PUBLICATIONS

Bao et al., "Artificial Disc Technology," *Neurosurg Focus*, American Association of Neurological Surgeons, Oct. 2000, pp. 1-7, vol. 9, No. 4.

(Continued)

*Primary Examiner* — Eduardo C Robert
*Assistant Examiner* — Elana B Fisher
(74) *Attorney, Agent, or Firm* — Saliwanchik, Lloyd & Eisenschenk

(57) ABSTRACT

The subject invention provides a modular six-degrees-of-freedom spatial mechanism for spinal disc prosthesis, with up to three rotational and up to three translational degrees-of-freedom within the entire workspace of a Functional Spinal Unit (FSU). The prosthetic disc mechanism consists of up to three independent cylindrical joints, each joint providing one linear and one rotational degree of freedom. The superior and inferior vertebral plates of the device anchor to the superior and inferior vertebrae of an FSU and the device maintains an inseparable mechanical linkage between those vertebrae for all normal motions and positions of the FSU. The device utilizes resilient spring elements, components that self-adjust in position and orientation, in conjunction with a fiber reinforced boot and toroidal belt, as well as a unique hydraulic damping system to accommodate dynamic and static forces and sudden shocks on the FSU. The device can adjust to maintain the appropriate, but changing, intervertebral spacing during normal FSU motion. Scaling, conjoined with cushioned, joint-limit stops, allows the device to realize almost any nominal spinal articulation, from the cervical to lumbar regions.

33 Claims, 33 Drawing Sheets

U.S. PATENT DOCUMENTS

| | | |
|---|---|---|
| 6,315,797 B1 | 11/2001 | Middleton |
| 6,368,350 B1 | 4/2002 | Erickson et al. |
| 6,375,682 B1 | 4/2002 | Fleishmann et al. |
| 6,395,032 B1 | 5/2002 | Gauchet |
| 6,419,704 B1 | 7/2002 | Ferree |
| 6,527,804 B1 | 3/2003 | Gauchet et al. |
| 6,579,320 B1 | 6/2003 | Gauchet et al. |
| 6,579,321 B1 | 6/2003 | Gordon et al. |
| 6,582,466 B1 | 6/2003 | Gauchet |
| 6,582,468 B1 | 6/2003 | Gauchet |
| 6,626,943 B2 | 9/2003 | Eberlein et al. |
| 6,645,248 B2 | 11/2003 | Casutt |
| 6,645,249 B2 | 11/2003 | Ralph et al. |
| 6,656,224 B2 | 12/2003 | Middleton |
| 6,682,562 B2 | 1/2004 | Viart et al. |
| 6,706,068 B2 | 3/2004 | Ferree |
| 6,726,721 B2 | 4/2004 | Stoy et al. |
| 6,733,532 B1 | 5/2004 | Gauchet et al. |
| 6,736,850 B2 | 5/2004 | Davis |
| 6,749,635 B1 | 6/2004 | Bryan |
| 6,770,095 B2 | 8/2004 | Grinberg et al. |
| 6,802,867 B2 | 10/2004 | Manasas et al. |
| 6,863,688 B2 | 3/2005 | Ralph et al. |
| 6,875,235 B2 | 4/2005 | Feree |
| 6,960,232 B2 | 11/2005 | Lyons et al. |
| 6,964,686 B2 | 11/2005 | Gordon |
| 6,966,929 B2 | 11/2005 | Mitchell |
| 6,972,038 B2 | 12/2005 | Zubok et al. |
| 6,981,989 B1 | 1/2006 | Fleishmann et al. |
| 6,989,032 B2 | 1/2006 | Errico et al. |
| 6,994,727 B2 | 2/2006 | Khandkar et al. |
| 7,011,685 B2 | 3/2006 | Arnin |
| 7,014,658 B2 | 3/2006 | Ralph et al. |
| 7,022,138 B2 | 4/2006 | Mashburn |
| 7,022,139 B2 | 4/2006 | Errico et al. |
| 7,044,969 B2 | 5/2006 | Errico et al. |
| 7,048,763 B2 | 5/2006 | Ralph et al. |
| 7,048,764 B2 | 5/2006 | Ferree |
| 7,060,100 B2 | 6/2006 | Ferree et al. |
| 7,066,960 B1 | 6/2006 | Dickman |
| 7,122,055 B2 | 10/2006 | Ralph et al. |
| 7,156,876 B2 | 1/2007 | Moumene et al. |
| 7,163,559 B2 | 1/2007 | Errico et al. |
| 7,186,268 B2 | 3/2007 | Errico et al. |
| 7,195,644 B2 | 3/2007 | Diaz et al. |
| 7,198,643 B2 | 4/2007 | Zubok et al. |
| 7,201,774 B2 | 4/2007 | Ferree |
| 7,201,776 B2 | 4/2007 | Ferree |
| 7,208,014 B2 | 4/2007 | Ralph et al. |
| 7,214,244 B2 | 5/2007 | Zubok et al. |
| 7,223,290 B2 | 5/2007 | Errico et al. |
| 7,235,102 B2 | 6/2007 | Ferree et al. |
| 7,258,699 B2 | 8/2007 | Errico et al. |
| 7,261,739 B2 | 8/2007 | Ralph et al. |
| 7,267,688 B2 | 9/2007 | Ferree |
| 7,270,680 B2 | 9/2007 | Ralph et al. |
| 7,270,681 B2 | 9/2007 | Cauthen |
| 7,273,496 B2 | 9/2007 | Mitchell |
| 7,291,171 B2 | 11/2007 | Ferree et al. |
| 7,314,487 B2 | 1/2008 | Ralph et al. |
| 7,316,714 B2 | 1/2008 | Gordon et al. |
| 7,331,994 B2 | 2/2008 | Gordon et al. |
| 7,331,995 B2 | 2/2008 | Eisermann et al. |
| 7,338,525 B2 | 3/2008 | Ferree |
| 7,361,192 B2 | 4/2008 | Doty |
| 2002/0111681 A1 | 8/2002 | Ralph et al. |
| 2003/0014110 A1 | 1/2003 | Ralph et al. |
| 2003/0014112 A1 | 1/2003 | Ralph et al. |
| 2004/0167626 A1 | 8/2004 | Geremakis et al. |
| 2004/0260396 A1 | 12/2004 | Ferree |
| 2005/0015152 A1 | 1/2005 | Sweeney |
| 2005/0192670 A1 | 9/2005 | Zubok |
| 2005/0234555 A1 | 10/2005 | Sutton |
| 2005/0240270 A1 | 10/2005 | Zubok |
| 2005/0273169 A1 | 12/2005 | Purcell |
| 2006/0036324 A1 | 2/2006 | Sachs |
| 2006/0136062 A1 | 6/2006 | Dinello |
| 2006/0235525 A1 | 10/2006 | Gil et al. |
| 2006/0235527 A1 | 10/2006 | Buettner-Janz et al. |
| 2006/0235529 A1 | 10/2006 | Ralph |
| 2007/0067038 A1 | 3/2007 | Studer et al. |
| 2007/0150062 A1 | 6/2007 | Zubok |
| 2008/0015699 A1 | 1/2008 | Voydeville |
| 2008/0021557 A1 | 1/2008 | Trieu |
| 2008/0027547 A1 | 1/2008 | Yu |
| 2008/0058940 A1 | 3/2008 | Wu |
| 2008/0065211 A1 | 3/2008 | Albert |
| 2008/0077242 A1 | 3/2008 | Reo |
| 2008/0077244 A1 | 3/2008 | Robinson |
| 2008/0077246 A1 | 3/2008 | Fehling |

FOREIGN PATENT DOCUMENTS

| | | |
|---|---|---|
| WO | WO 2007/076194 A2 | 7/2007 |
| WO | WO 2007/076194 A3 | 7/2007 |

OTHER PUBLICATIONS

Bao et al., "The artificial disc: theory, design and materials," *Biomaterials*, 1996, pp. 1157-1167, vol. 17, No. 12.

Bogduk, N. et al., "Biomechanics of the cervical spine. I: Normal kinematics," *Clinical Biomechanics*, 2000, pp. 633-648, vol. 15.

Bogduk et al., "A biological basis for instantaneous centers of rotation of the vertebral column," *Proc. Instn. Mech. Engrs.*, 1995, pp. 177-183, vol. 209.

Bogduk et al., *Clinical Anatomy of the Lumbar Spine*, ISBN 0-443-03505-9, 1987, Churchill-Livingstone Melbourne Edinburgh London New York.

Büttner-Jantz, et al., *The Artificial Disc*, ISBN 3-540-41779-6, 2003, Springer-Verlag, Berlin Heidelberg New York.

van Mameren et al., "Cervical Spine Motion in the Sagittal Plane II: Position of Segmental Averaged Instantaneous Centers of Rotation—A Cineradiographic Study," *Spine*, 1992, pp. 467-474, vol. 17, No. 5.

Mow et al., *Basic Orthopaedic Biomechanics*, Lippincott-Raven Pub., N.Y., 2$^{nd}$ Edition, 1997.

Panjabi, M. "Instantaneous Center of Rotation and Instability of the Cervical Spine: A Clinical Study," *Spine*, 1997, pp. 647-648, vol. 22, No. 6.

Panjabi et al., "Articular Facets of the Human Spine: Quantitative Three-Dimensional Anatomy," *Spine*, 1993, pp. 1298-1310, vol. 18, No. 10.

Yoganandan N. et al., "Chapter 5—Biomechanics of the Cervical Spine," *Principles of Spinal Surgery*, 1996, pp. 69-83.

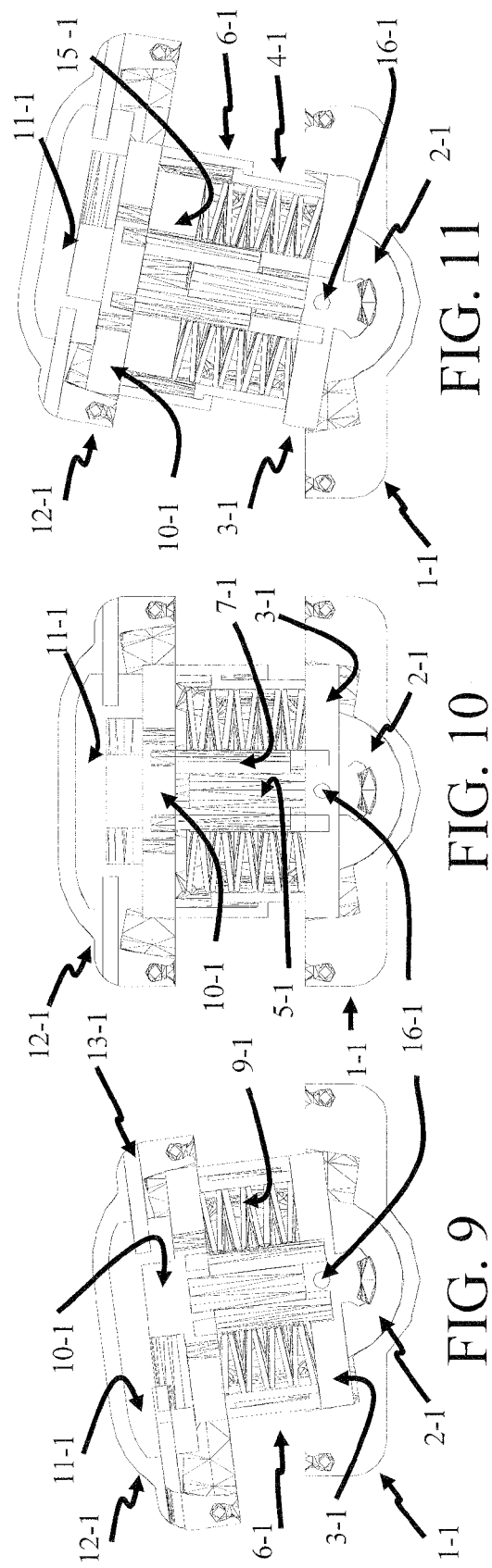

DYNAMIC SIX-DEGREES-OF-FREEDOM INTERVERTEBRAL SPINAL DISC PROSTHESIS

BACKGROUND OF INVENTION

Spinal disc herniation, a common ailment, often induces pain, as well as neurologically and physiologically debilitating processes for which relief becomes paramount. If conservative treatments fail, the more drastic measures of discectomies and spinal fusion may be indicated. The latter treatment, while providing short term relief, often leads to excessive forces on facet joints adjacent to the fusion and creates further problems over time. Drastic treatments are usually unable to restore normal disc function. The loss of disc function has led to a number of disc prostheses that attempt to provide natural motion.

The literature documents that the Instantaneous Axis of Rotation (IAR) during sagittal rotation of the superior vertebra with respect to the inferior vertebra of a Functional Spinal Unit (FSU) in the cervical spine moves significant distances during flexion and extension of the spine (Mameren H. van, Sanches H., Beursgens J., Drukker, J., "Cervical Spine Motion in the Sagittal Plane II: Position of Segmental Averaged Instantaneous Centers of Rotation—A Cineradiographic Study", *Spine* 1992, Vol. 17, No. 5, pp. 467-474). This motion varies widely between functional spinal units on an individual spine and between individuals and depends on age, time-of-day, and the general health and condition of the intervertebral discs, facet joints and other components of the FSU and spine. A moving IAR means that the superior vertebra both rotates and translates while moving with respect to the inferior vertebra of an FSU. Natural spinal motions place severe requirements on the design of a prosthetic disc; simple rotational joints are not able meet those requirements.

In addition, motion coupling between axial and lateral bending and other functional spinal units involved in the overall spinal motion increases the complexity and difficulty in developing a prosthetic disc replacement that realizes natural spinal motion. The complex facet surfaces in an FSU significantly influence and constrain sagittal, lateral and axial motions. The orientation of these facet surfaces vary with FSU location in the spine and induce wide variations in motion parameters and constraints. The complex motion of a superior vertebra with respect to the associated inferior vertebra of an FSU, certainly in the cervical spine, cannot be realized by a simple rotation or simple translation, or even a combination of rotation and translation along a fixed axis, and still maintain the integrity and stability of the FSU and facet joints.

One advantage of a general motion spatial mechanism of a disc prosthesis, as described in this application, is that it solves the natural motion problem for disc prostheses and offers a scalable mechanism for disc replacement without loss of general motion capabilities in the FSU.

Researchers have attempted to design a successful intervertebral disc for years. Salib et al., U.S. Pat. No. 5,258,031; Marnay, U.S. Pat. No. 5,314,477; Boyd et al., U.S. Pat. No. 5,425,773; Yuan et al., U.S. Pat. No. 5,676,701; and Larsen et al., U.S. Pat. No. 5,782,832 all use ball-and-socket arrangements fixed to the superior and inferior plates rigidly attached to the vertebrae of an FSU. However, these designs limit motion to rotation only about the socket when the two plates are in contact. As the literature points out (Bogduk N. and Mercer S., "Biomechanics of the cervical spine. I: Normal kinematics", *Clinical Biomechanics*, Elsevier, 15(2000) 633-648; and Mameren H. van, Sanches H., Beursgens J., Drukker, J., "Cervical Spine Motion in the Sagittal Plane II: Position of Segmental Averaged Instantaneous Centers of Rotation—A Cineradiographic Study", Spine 1992, Vol. 17, No. 5, pp. 467-474), this restricted motion does not correspond to the natural motion of the vertebrae, for either sagittal plane motion, or for combined sagittal, lateral and axial motion. Further, when the two plates, as described in the cited patents, are not in contact, the devices are unable to provide stability to the intervertebral interface, which can allow free motion and lead to disc related spondylolisthesis, FSU instability, and excessive facet loading.

As a further elaboration on the many ball-and-socket configurations, consider Salib et. al. (U.S. Pat. No. 5,258,031) as an example of previous efforts to address this problem. The Salib ball-and-socket arrangement only provides 3 independent axes of rotation and no translation when engaged.

During complex motions of an FSU, the superior vertebra, in general, requires translation along three independent directions. A sliding ovate structure in an oversized socket cannot perform such general translation motions, either, as it must engage in a trajectory dictated by its socket's geometrical surface and does not change the deleterious effects that may occur on the facet joints of the unit.

Currently known devices appear to have similar motion and instability limitations, such as the rocker arm device disclosed by Cauthen (U.S. Pat. Nos. 6,019,792; 6,179,874; 7,270,681), the freely moving sliding disc cores found in the Bryan et al. patents (U.S. Pat. Nos. 5,674,296; 5,865,846; 6,001,130; and 6,156,067) and the SB Charité™ prosthesis, as described by Buttner-Jantz K., Hochschuler S. H., McAfee P. C. (Eds), *The Artificial Disc*, ISBN 3-540-41779-6 Springer-Verlag, Berlin Heidelberg New York, 2003; and U.S. Pat. No. 5,401,269; and Buettner-Jantz et al. U.S. Pat. No. 4,759,766). In addition, the sliding disc core devices of the Bryan et al. and SB Charité™ devices do not permit natural motion of the joint for any fixed shape of the core.

With the above-described prosthetic devices, when the FSU extends, the prosthesis's sliding core, in some cases, generates unnatural constraining forces on the FSU by restricting closure of the posterior intervertebral gap in the FSU. Further, the core does not mechanically link the upper and lower plates of the prosthesis and is unable to maintain the intervertebral gap throughout the range of motion. Such conditions can contribute to prosthetic disc spondylolisthesis. In general, unconstrained or over-constrained relative motion between the two vertebral plates in a prosthetic disc can contribute to FSU instability over time.

Static loading in current prosthetic disc technology appears to be minimal and limited to mostly rigid support. For example, load bearing and shock absorption in the SB Charité™ design and others (e.g. Bryan et al., U.S. Pat. No. 5,865,846) rely on the mechanical properties of the resilient, ultra-high-molecular-weight polyethylene core to provide both strength and static and dynamic loading. The rigidity of the sliding core appears to offer little energy absorption and flexibility to meet the intervertebral gap requirements during motion, and may likely generate excessive reaction forces on the spine during flexion, forces that can potentially produce extra stress on facet joints and effect mobility.

More recent attempts to provide dynamic and static loading capability is taught in the series of patents by Ralph et al (U.S. Pat. Nos. 6,645,249, 6,863,688, 6,863,688, 7,014,658, 7,048,763, 7,122,055, 7,208,014, 7,261,739, 7,270,680, 7,314,487) wherein the force restoring mechanism begins with a multi-pronged domed spring between two plates and ends with a wave-washer as the force restoring element. The multi-pronged domed spring employs a ball-and-socket arrangement on the upper plate and allows relative rotations between the spring-lower plate and the upper plate. This arrangement, during normal FSU operation, places moments of force on the spring that tend to distort the spring and place high stresses on the set screws holding the spring down. The effects of force moments on the prongs and the dome spring is mitigated by later designs where various modifications of the spring element, as for example the spiral Belleville washer in U.S. Pat. No. 7,270,680, provides the spring more resilience to moments of force. As taught in these patents, the motion of the upper plate is limited to compression and rotation. Lateral and sagittal translations are not accommodated and so general motion in the FSU is not enabled by the device.

The work of Errico et al (U.S. Pat. Nos. 6,989,032, 7,022, 139, 7,044,969, 7,163,559, 7,186,268, 7,223,290, and 7,258, 699) elaborates on the mechanical design of the patents of Ralph et al. A specially designed Belleville type washer provides a restoring force to compressions. Rotations of the superior plate of the device in a fixed ball-and-socket arrangement transfers moments of force about the washer central axis to a rigid structure. It is notable that the instruction in these designs specifically proscribes lateral motions (sagittal and lateral translation). Errico et al. employ a tapered projection attached to the ball to limit rotation angles.

Another approach to incorporate dynamic and static force response is taught by Gauchet (U.S. Pat. Nos. 6,395,032, 6,527,804, 6,579,320, 6,582,466, 6,582,468, and 6,733,532) wherein a hydraulic system provides shock absorption by means of a cushion between two plates contained within sealed flexible titanium bellows. Gauchet suggests the bellows can be designed to accommodate lateral forces and axial rotation that is permitted by the cushion, which, to allow sliding motion, is not attached to at least one plate. The titanium bellows can accommodate some axial rotations, but do not seem suitable for other rotations, which can cause excessive stresses on the bellows. A cushion internal to the cylinder, being flexible and not attached to at least one plate, can accommodate any rotation (U.S. Pat. Nos. 6,582,466 and 6,733,532).

Fleishman et al in U.S. Pat. Nos. 6,375,682 and 6,981,989 utilize hydraulic action coupled with a flexible bellows to mitigate sudden forces. The bellows concept is similar to that of Gauchet.

Eberlein et al (U.S. Pat. No. 6,626,943) utilizes a fiber ring to enclose a flexible element. The forces and moments of force are absorbed by the ring and the flexible element. The device taught in this invention uses a boot in much the same manner as Eberlein's fiber ring. Other inventions teach this concept as well, namely, Casutt in U.S. Pat. No. 6,645,248. Diaz et al (U.S. Pat. No. 7,195,644) also uses a membrane and enclosed cushioning material in their ball and dual socket joint design.

Middleton suggests a variety of machined springs as the central component of a disc prosthesis in U.S. Pat. Nos. 6,136,031, 6,296,664, 6,315,797, and 6,656,224. The spring is notched to allow static and dynamic response primarily in the axial direction of the spring. But, lateral and sagittal translations and general rotations appear to be problematic in these designs. The ability of such springs to tolerate off-axis compression forces may also be problematic.

Gordon instructs deforming a machined spring as the principle separating and force management component (U.S. Pat. Nos. 6,579,321, 6,964,686, and 7,331,994). In U.S. Pat. No. 7,316,714, also to Gordon, the emphasis is on posterior insertion of a disc prosthesis that can provide appropriate motion. However, this latter design does not appear to accommodate for static and dynamic loading and there appears to be no accommodation for lateral and sagittal translations.

Zubok instructs in U.S. Pat. No. 6,972,038(Column 3; Line 35) that " . . . the present invention contemplates that with regard to the cervical anatomy, a device that maintains a center of rotation, moving or otherwise, within the disc space is inappropriate and fails to properly support healthy motion." This may be true as long as translations within the prosthesis mechanism do not adequately compensate for the total motion induced by an LAR outside of the disc space. Several approaches by Ferree (U.S. Pat. Nos. 6,419,704, 6,706,068, 6,875,235, 7,048,764, 7,060,100, 7,201,774, 7,201,776, 7,235,102, 7,267,688, 7,291,171, and 7,338,525) primarily instruct how to cushion a prosthetic FSU in various ways. An exception is U.S. Pat. No. 6,706,068, which describes a design to perform certain kinematic motion of a disc prosthesis without dynamic or static cushioning support, and U.S. Pat. No. 7,338,525, which instructs on anchoring a disc prosthesis.

Aebi incorporates what essentially amounts to a hook joint (orthogonal revolute joints) in EP1572038B1 as the means for realizing motion. While the Aebi arrangement of revolute joints does allow for sagittal and lateral rotations, it does not engage in the remaining four degrees of freedom in three-space, namely, sagittal, lateral, and axial translations along with axial rotations.

Mitchell (U.S. Pat. No. 7,273,496B2) uses two revolute joints by means of orthogonal cylinders placed on top of each other and embedded as a crossbar element between vertebral plates with cavities for accepting the crossbar. This device has the limitations of motion similar to the Aebi device, and the further limitation of not linking the two plates together with the crossbar.

Khandkar (U.S. Pat. No. 6,994,727 B2) provides two orthogonal convex curvate bearing structures, with offset cylindrical radii of curvature, placed between the vertebral plates. An insert, with orthogonal, variable-curvature concave bearing surfaces, is placed between, and generally conforms to, the orthogonal convex bearings on the vertebral plates. This arrangement of bearings allows sagittal, lateral, and axial rotations of various ranges, dictated by the curvate bearing structures and the insert. The variable curvate surfaces allows some lateral and sagittal translations with FSU distractions, utilizing normal spinal forces to resist the distraction and, hence, the motion. There is no control on the forces involved, so this method could lead to possible stress on other spinal joints. The inserted device is not kinematically chained to the rest of the device and can possibly be spit out. Although, as instructed, the device is self-correcting within a limited range, tending towards a stable equilibrium established for the device in normal position. The variable curvatures can result, typically, in line-contact bearing manifolds that will wear the surfaces, possibly causing changes in the performance and characteristic motion of the device.

DiNello (US Publication No. 2006/0136062A1) instructs on how to adjust height and angulation of a motion disc after implantation.

With respect to the lower vertebra in an FSU, all possible, natural loci of motion of any four non-planar, non-collinear points located in the superior vertebra define the natural workspace of a FSU. This workspace varies from one FSU to another on the spine, creating considerable spinal disc prosthesis design problems.

The FSU workspace boundary is dictated by the sagittal, lateral and axial angle limits reported in the literature (Mow V. C. and Hayes W. C., *Basic Orthopaedic Biomechanics*, Lippincott-Raven Pub., N.Y., $2^{nd}$ Addition, 1997). However, these angle limits do not reveal the underlying complex motion between two vertebrae in an FSU. The study by Mameren H. van, Sanches H., Beursgens J., Drukker, J., "Cervical Spine Motion in the Sagittal Plane II: Position of Segmental Averaged Instantaneous Centers of Rotation—A Cineradiographic Study", Spine 1992, Vol. 17, No. 5, pp. 467-474 demonstrates this complexity in the cervical spine, even when the motion is restricted to flexion and extension.

In light of the above observations and limitations, it can be appreciated that there is a need for a spinal disc prosthesis that can accommodate a broader range of motions, while maintaining disc stability and integrity under static and dynamic loads.

BRIEF SUMMARY

The subject invention provides a spinal disc prosthesis capable of providing spatial movement with up to 6 degrees of freedom (FIG. 1 and FIG. 2). In a preferred embodiment, the device of the subject invention facilitates sagittal, lateral, and axial vertebral displacements and rotations when utilized in the spine of a patient.

In one embodiment, the modular spinal disc prosthesis of the subject invention comprises superior and inferior vertebral plates, as well as a flexible, boot-protected, replaceable 6-DOF modular prosthetic disc mechanism (linkage). The devices of the subject invention can achieve up to 6 degrees of freedom, including up to 3 independent rotational degrees of freedom and up to 3 independent linear degrees of freedom, such that the device of the subject invention facilitates sagittal, lateral, and axial vertebral displacements and rotations when utilized in the spine of an animal. The modular prosthetic disc mechanism of the subject invention can comprise three orthogonal cylindrical joint elements for general positioning and orienting of the superior vertebra with respect to the inferior vertebra of a Functional Spinal Unit.

In one embodiment, the cylindrical joints kinematically connect a superior and inferior vertebral plate by means of mechanically interlocking and inseparable cylindrical joint elements arranged mutually orthogonal to each other. Thus, the elements remain attached to one another and the vertebral plates throughout natural FSU motion. In a further embodiment, the vertebral plates can be rigidly fixed to the superior and inferior vertebrae of a Functional Spinal Unit (FSU) or, with obvious modification of the device's vertebral plates, modularly fixed to such plates, as discussed in Doty (U.S. Pat. No. 7,361,192), which is hereby incorporated by reference. In a still further embodiment, displacements along the axial axis, a line perpendicular to the axial plane of the FSU (not the patient body axial axis), arise from compressing a spring-dashpot element that also constitutes a central axial cylindrical joint whose components constitute a central shock absorbing system. Hydraulic portals within the device can also facilitate shock absorbing characteristics while at the same time forcing a bio-lubricant, or other substance, to flow through and around the components of the device. This central axial cylindrical joint, which includes a combined dual cylinder and a spring stack, provide a column element that resists shear forces and promotes the rotation and translation of the various joint elements when the FSU is subjected to shear forces.

To further assist with shock-absorption, a flexible, elastomer boot can be utilized to surround the functional elements of the prosthetic device. The boot can further be sealed such that surrounding bodily fluids cannot contact the functional elements of the prosthetic device. In still a further embodiment, the sealed boot can contain fluids or other substances to lubricate the functional elements of the prosthetic device. The central cylindrical joint, can further act as a hydraulic pump, to helps divert compression shocks to the walls of the boot, causing the boot to bulge and absorb some of the energy of the shock.

To further assist the boot and central cylindrical joint in resisting shocks and arbitrary FSU force loads, an internal toroidal-belt cushioning element can be utilized with the subject invention.

Thus, the present invention provides an articulated, modular 6-Degrees-of-Freedom (6-DOF) spatial mechanism for intervertebral spinal disc prosthesis that provides highly advantageous spatial motion between upper and lower vertebrae of an FSU with static and dynamic load capabilities.

The device of the subject invention can be used to assist in maintaining natural spinal flexibility and motion during simultaneous, dynamically changing, curvilinear axial, lateral and sagittal rotations and translations, regardless of the details and wide variations of that motion in a patient.

The unit can also assist in accommodating variable disc spacing under static and dynamic load during normal FSU operation. For example, the disc spacing under static load in the normal spinal position can be selected by adjusting certain components of the device. The invention can absorb compression shocks, sustain static loads, respond to dynamic loads, help alleviate spinal cord and nerve root compression, resist torsion and extension forces and reduce excessive facet joint stress and wear.

The mechanism's components, when coupled together, form a device that preserves its own mechanical integrity, connectedness (inseparable kinematic chain), and motion properties throughout the biologically constrained motion space (workspace) of the FSU. The complete generality of the device allows for modifying the range of the mechanism's motion parameters and workspace, physical size, material composition, and mechanical strength to suit ordinary mechanical applications as well as spinal disc prosthetics.

The complete 6-DOF motion capability of the prosthetic disc linkage mechanism is able to allow natural motions dictated by the muscles and ligaments of the spine. Throughout normal motion, the system of the subject invention stabilizes the FSU because of its ability to maintain continuity of mechanical connection between the superior and inferior vertebrae while at the same time providing load bearing and permitting motion only within the nominal disc operating range or workspace. The mechanical continuity is realized by a kinematic chain of inseparable jointed elements.

BRIEF DESCRIPTION OF DRAWINGS

In order that a more precise understanding of the above recited invention be obtained, a more particular description of the invention briefly described above will be rendered by reference to specific embodiments thereof that are illustrated in the appended drawings. Understanding that these drawings depict only typical embodiments of the invention and are not therefore to be considered as limiting in scope, the invention will be described and explained with additional specificity and detail through the use of the accompanying drawings in which:

FIG. 9, FIG. 10, and FIG. 11 illustrate a bootless, sagittal plane cutaway of an embodiment of the subject invention in flexion, normal and extension as shown in FIG. 6, FIG. 7, and FIG. 8. A spring element 9-1 opposes the collapse of the superior hydraulic cylinder wall 6-1 over the inferior hydraulic cylinder wall. In this embodiment, the two hydraulic cylinder wall elements slideably move along their matching wall surfaces without interference, except for the wall projections or lock rings at the top edge of 4-1 and bottom edge of 6-1. The turning axis for the sagittal rotation cylinder 2-1 is indicated by 16-1

DETAILED DISCLOSURE

Figure 1:
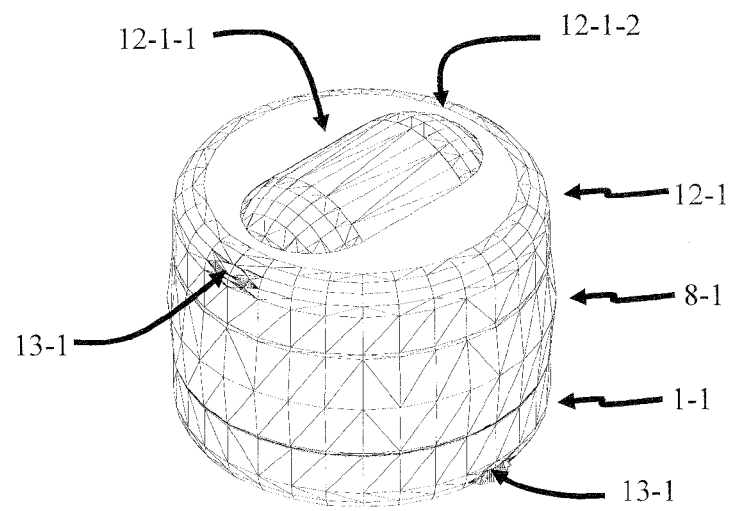
FIG. 1 depicts one embodiment of an assembled disc prosthesis of the subject invention in perspective. Visible elements of this embodiment, shown in this view, are a superior vertebral plate 12-1, a fiber-reinforced, resilient boot 8-1 and an inferior vertebral plate 1-1. Also shown, are a locking key 13-1 that can be pressure fit, welded or otherwise fixedly positioned into 1-1 and projects interiorly into a sagittal rotating cylinder 2-1 (not shown here), which rotates about the curvate projection of the locking key.
Figure 2:
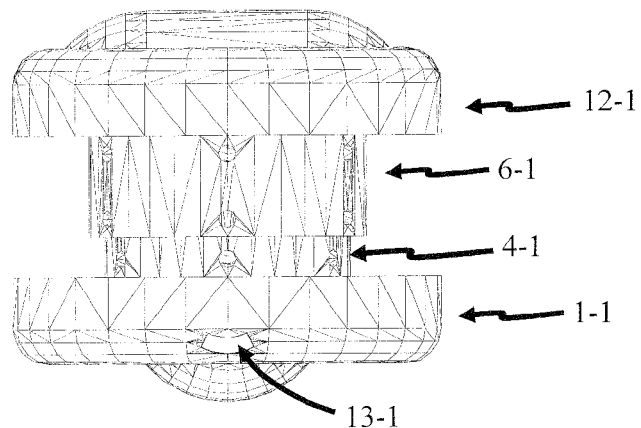
FIG. 2 shows an embodiment of the invention without the boot, revealing an inferior hydraulic cylinder wall 4-1 and a superior hydraulic cylinder wall 6-1.
Figure 3:
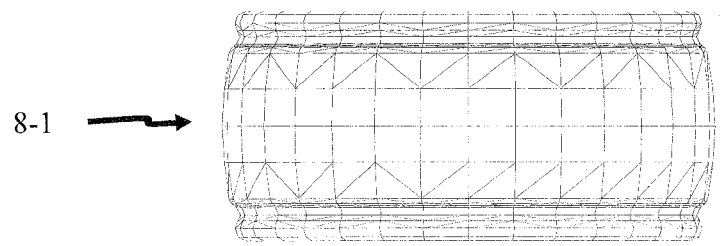
FIG. 3 illustrates an embodiment of a boot of the subject invention of resilient, fiber-reinforced elastomer matrix that can be firmly attached to the superior and inferior vertebral plates (12-1 and 1-1).

The subject invention provides embodiments of intervertebral disk protheses. More specifically, the subject invention pertains to one or more embodiments of an intervertebral disk prosthesis capable of providing up to 6 degrees of freedom.

The subject invention is particularly useful for the treatment of spinal disk herniation. However, a person with skill in the art will be able to recognize numerous other uses that would be applicable to the devices and methods of the subject invention. Thus, while the subject application describes a use for treatment and/or removal of spinal disk herniation, other modifications apparent to a person with skill in the art and having benefit of the subject disclosure are contemplated to be within the scope of the present invention.

Throughout the subject application, reference is made to a "first embodiment" and a "second embodiment". These terms are used merely for literary convenience to refer to two specific embodiments described herein that illustrate the various features of the subject invention. For example, the first embodiment of the subject invention is described as having kinematically chained or kinematically linked surface bearings or contacts. The second embodiment of this invention is described as having the surface bearings replaced by kinematically chained or kinematically linked line rod or multi-point contact ball bearings. As will be described herein, features and elements of each embodiment can be interchangeable. A person with skill in the art, having benefit of the subject disclosure, would be able to determine numerous alternative arrangements of the elements and/or components described herein, or equivalent alternative embodiments therefore. Thus, the subject invention is not limited to only the first and second embodiments disclosed herein.

As used in the subject application, "kinematic chain", "kinematic linkage", and "kinematic connection" refer to a mechanical linkage inseparably connecting the components of the device of the subject invention. It is known to those with skill in the art that a 'mechanical linkage' is a series of physical links connected with joints to form a closed chain, or a series of closed chains. Thus, as will be described herein, the components of the device of the subject invention are inseparably linked, such that the components can move relative to each other, but do not become separated one from the other. That is, the components of the device of the subject invention remain interconnected or physically attached at all times to each other, and to the vertebrae when installed in an FSU.

The term "patient" as used herein, describes an animal, including mammals to which the systems and methods of the present invention are applied. Mammalian species that can benefit from the disclosed systems and methods include, but are not limited to, apes, chimpanzees, orangutans, humans, monkeys; domesticated animals (e.g., pets) such as dogs, cats, guinea pigs, hamsters; veterinary uses for large animals such as cattle, horses, goats, sheep; and any wild animal for veterinary or tracking purposes.

The terms "surgeon" or "physician" as used in the subject application are merely for literary convenience. The terms should not be construed as limiting in any way. The devices, apparatuses, methods, techniques and/or procedures of the subject invention could be utilized by any person desiring or needing to do so and having the necessary skill and understanding of the invention.

Also, as used herein, and unless otherwise specifically stated, the terms "operable communication" and "operably connected" mean that the particular elements are connected in such a way that they cooperate to achieve their intended function or functions. The "connection" may be direct, or indirect, physical or remote.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

With reference to the attached figures, which show certain embodiments of the subject invention, it can be seen that the subject invention (shown generally in FIG. 1, FIG. 12, FIG. 14, FIG. 29 and FIG. 30) differs from existing designs. A novel implementation 1) allows six-degrees-of-freedom throughout the Functional Spinal Unit (FSU) workspace while simultaneously bearing compressive, tension and torsion loads; 2) maintains the integrity of the variable intervertebral spacing required (under compression the intervertebral gap should narrow some and under tension widen some); and retains an unbroken (fully connected) mechanical linkage between the superior and inferior vertebra during any normal motion of the affected FSU, the later can promote joint stability and assist in preventing spondylolisthesis of the FSU.

When appropriately scaled, the invention is capable of tracking arbitrary three-dimensional translational and three-dimensional rotational motions of the superior vertebra with respect to the inferior vertebra. In a patient, this can include an FSU from spinal discs C2-C3 down to L5-S1, while adjusting the disc height and accommodating the various forces and moments-of-force applied to the FSU during any motion. Thus, the subject invention can accommodate the workspace of any FSU along the spine and is a considerable improvement over current disc designs.

One to three cylindrical joints can kinematically permit motion from two to six degrees of freedom throughout the workspace of the FSU. The range of motion for all revolute (0 to ±15 degrees of rotation) and slider (0 to ±1.5 millimeters of displacement) joints in the invention can be mechanically programmed with judicious choice of joint limit stops, including cushioned stops to reduce impact wear on the stops. A central hydraulic cylinder spring-dashpot system offers both static and dynamic stability to the FSU with shock absorbing characteristics. The central hydraulic cylinder rotates and slides sagittally with respect to the inferior vertebra of an FSU and rotates and slides laterally with respect to the superior vertebra of an FSU. The relative motion of the central hydraulic spring-dashpot with respect to the inferior and superior vertebrae of an FSU allows it to generate an opposing force to any compressive static or dynamic load acting on the rotating and sliding axial axis of the FSU, regardless of the position of the vertebrae and the complex motion involved. Non-axial components of the force will act to move the prosthesis until joint limit stops rigidly oppose any further motion in that particular direction or orientation. A protective boot assists in the hydraulic and shock absorption properties. Additional cushioning elements can also be used to enhance shock absorption.

The cylindrical joint axes of the invention can parallel a rotated version of the sagittal, frontal and axial plane axes, as defined for an animal body, enabling lateral, sagittal, and axial axes displacements and lateral, sagittal and axial axes rotations. The actual inclination of the invention with respect to the body coordinates depends upon the natural inclination of the FSU to the body planes. Specifically, the invention should be inserted into an FSU, with disc removed, such that the superior and inferior surfaces are parallel to the client's FSU vertebral surfaces in the normal posture. Such placement will maximize the effective work space of the prosthesis.

In the description to follow, the axes of the cylindrical joints will be labeled as sagittal, lateral, and axial, it being understood that these axes are actually parallel to rotated versions of the typically defined patient body axes and that the frontal, sagittal and axial planes in the text will refer to those of the FSU body and not the animal body.

Figure 13:
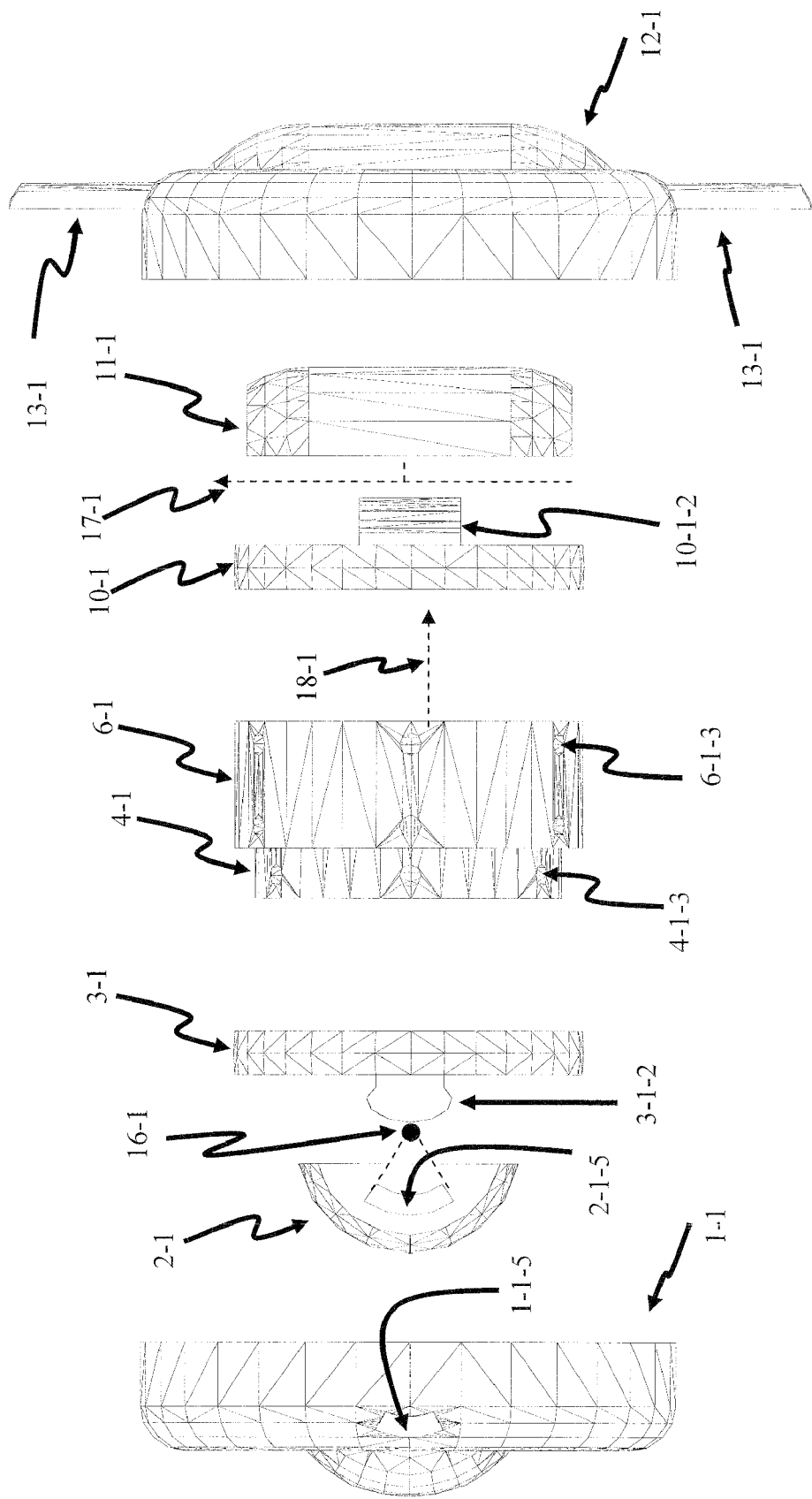
FIG. 13 shows a exploded side view of an embodiment of the subject invention without the boot, illustrating most, but not all, of the invention elements, from left to right, an inferior vertebral plate 1-1, a sagittal rotation cylinder 2-1, a spring platform and an inferior hydraulic cylinder base 3-1, an inferior hydraulic cylinder wall 4-1, a superior hydraulic cylinder wall 6-1, a top cover 10-1 to the superior hydraulic cylinder wall, a lateral rotation cylinder 11-1, a superior vertebral plate 12-1, and locking keys 13-1. In this embodiment, the locking keys, which can press fit or weld into the inferior vertebral plate 1-1 are not shown, but the slot 1-1-5 into which the keys fit is illustrated. A sagittal rotation and slider axis 16-1 (out of the page), a lateral rotation and slider axis 17-1, and an axial rotation and slider axis 18-1 are also shown.
Figure 14:
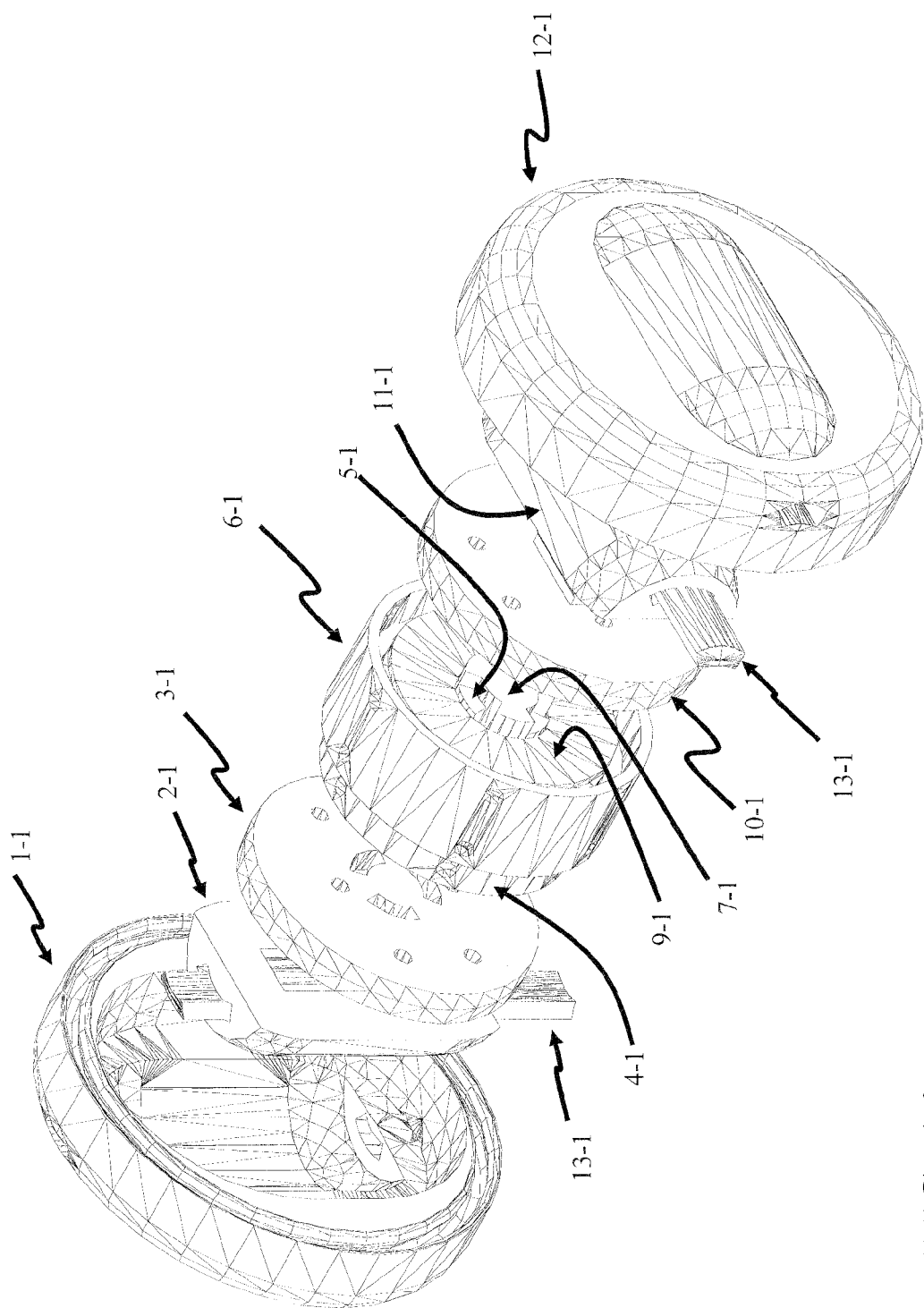
FIG. 14 is a perspective exploded view of an embodiment of the invention assembly without the boot. More details of the corresponding invention elements come into view. In particular, a spring stack element 9-1, an inferior segmented-wall cylinder core 5-1, and a superior segmented-wall cylinder core 7-1.
Figure 17:
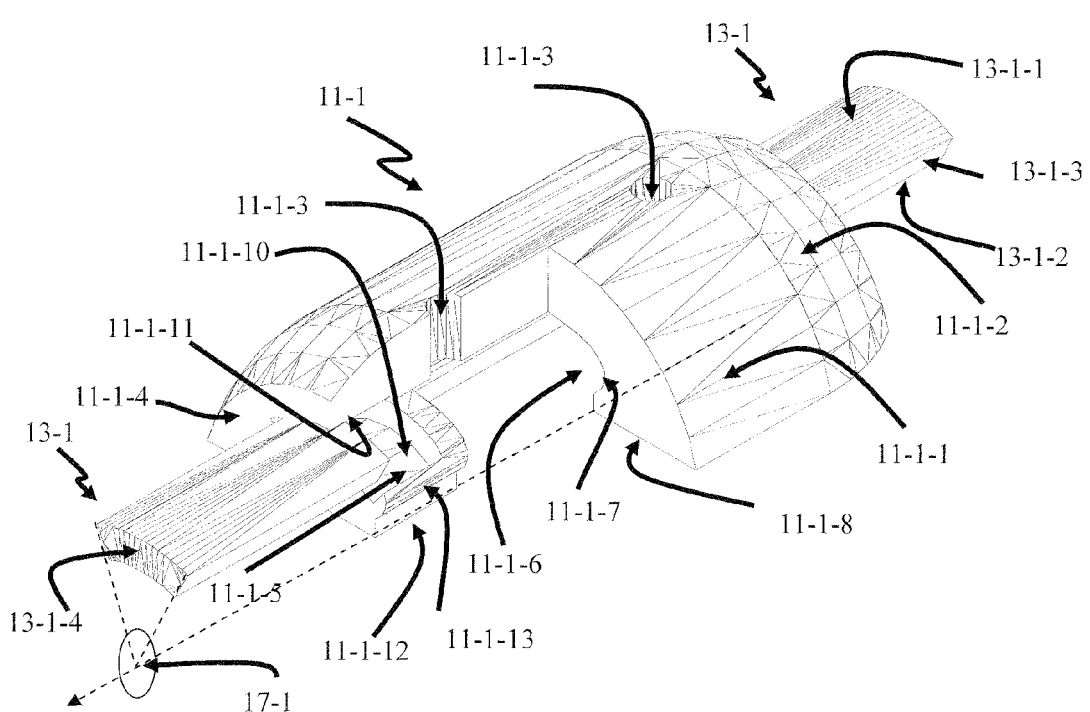
FIG. 17 details a top cutaway perspective view of an embodiment of a lateral rotation cylinder of the subject invention. A sagittal rotation cylinder oriented the same way (curved cylinder surface up) would appear the same in this embodiment. This embodiment shows how the lock key can fit into an oversized slot 11-1-5 in the cylinder. The slot is slightly larger than the key and the curvatures for both the top key surface 13-1-1 and underside key surface 13-1-2 match the slot surfaces 11-1-11 and 11-1-10. The center of curvature for all these surfaces falls on the cylinder's turning axis. This arrangement allows the lateral rotation cylinder to rotate freely about the keys located at each end. At the same time, the keys can retain the lateral rotation cylinder within the socket of the superior vertebral plate 12-1. The key slot 11-1-5 can be oversized in degrees by twice the desired maximum rotation angle of the cylinder. Also shown are hydraulic portals 11-1-3 that can drain the central hydraulic cylinder and provide lubricating fluid, under pressure, to the joint.
Figure 18:
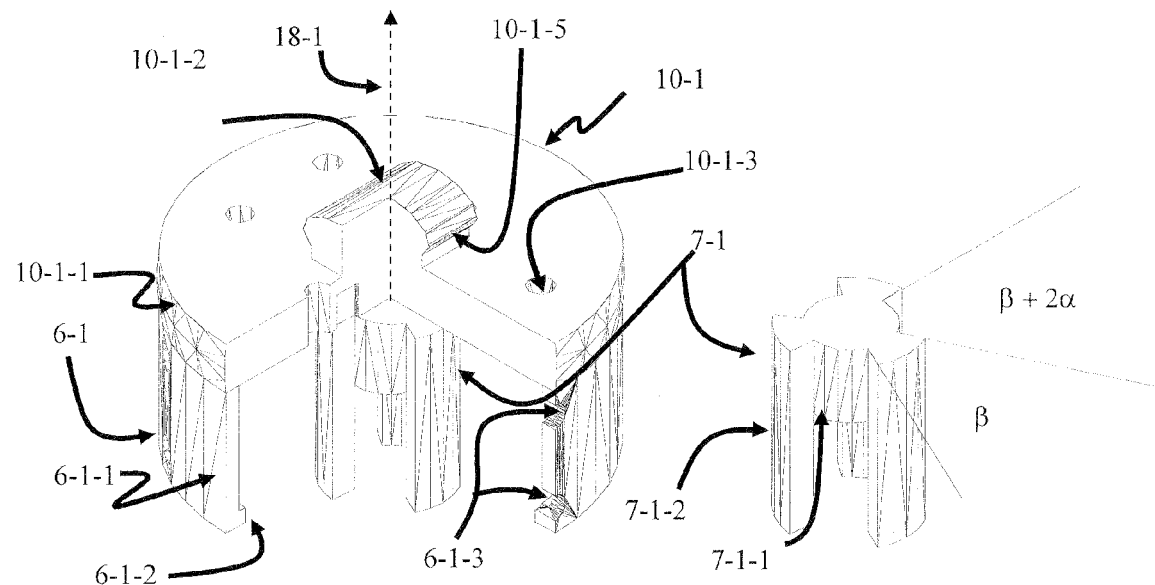
FIG. 18 details an embodiment of a superior hydraulic cylinder wall 6-1 and its superior inner core 7-1, the latter consisting of inner cylinder 7-1-1 and walled segments 7-1-2. Also seen are the top cover 10-1 and some of its features.
Figure 23:
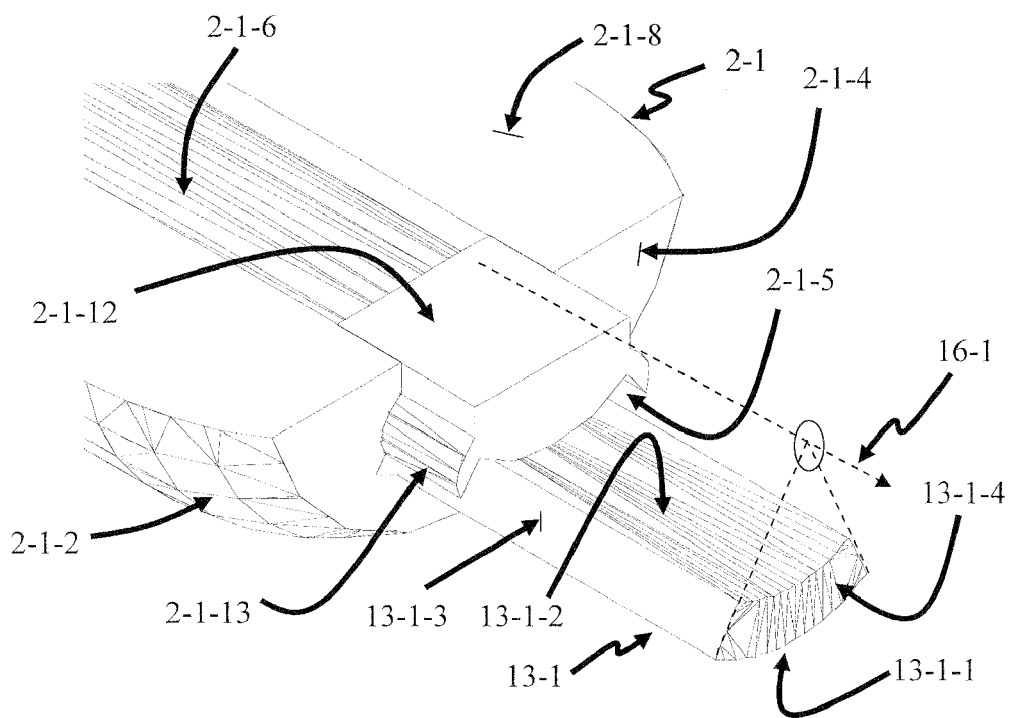
FIG. 23 shows how the sagittal rotation cylinder 2-1, the bearing stop 2-1-12 and the lock key 13-1 fit together in an embodiment of the subject invention. The lock keys at each end of the sagittal rotation cylinder can press fit or weld into the inferior vertebral plate 1-1, but fit loosely into the bearing stops 2-1-12 so as not to bind or hinder rotation of the sagittal cylinder about the keys or to bear any load, which is transmitted through the larger surface 2-1-1 and 2-1-2 of the cylinder. At the same time, the keys retain the sagittal rotation cylinder within the socket of the inferior vertebral plate 1-1.

A particular embodiment of the spinal disc prosthesis of the subject invention is operated by the muscles and ligaments of the spine when installed in an FSU. These muscles and ligaments drive the spring-damping system and resultant motion of the prosthesis. The kinematic generality of the prosthesis's motion capabilities, allows natural movements of any FSU in which the prosthesis is placed. In one embodiment, the three cylindrical joint axes (16-1, 17-1, 18-1, FIG. 13) are mutually orthogonal, providing three independent degrees of freedom for rotation and translation along the sagittal cylindrical joint's turning and sliding axis, referred to herein as the sagittal axis 16-1 (FIG. 23), the lateral cylindrical joint turning and sliding axis, referred to herein as the lateral axis 17-1 (FIG. 17), and the central axis of the hydraulic cylinder, referred to herein as the axial axis 18-1 (FIG. 18). In one embodiment, the sagittal axis 16-1 is fixed to the inferior vertebral plate 1-1, hence, by rigid connection, to the superior vertebra of the FSU. In a further embodiment, the lateral axis is fixed to the superior vertebral plate 12-1, hence, by rigid connection, to the superior vertebra of the FSU. In a yet further embodiment, the axial axis is always the common normal of the skew sagittal and lateral axes for arbitrary motions of the superior vertebra of the FSU with respect to its inferior vertebra.

The Instantaneous Axis of Rotation (IAR) of an FSU often changes during the motion of its superior vertebra with respect to its inferior vertebra. As mentioned above, the orienting capability of the sagittal, lateral, and axial axes of rotation of the three revolute joints, which is constrained to be within the device, and is not kinematically sufficient to mimic natural motion of the FSU, but, the translation capabilities of the three cylindrical joints correct this. In one embodiment, to sufficiently kinematically mimic natural motion of an FSU and accommodate additional translational requirements, the subject invention is configured with three independent linear translations, one associated with each cylindrical joint, that can, when coupled with the three cylindrical rotations, accommodate the differences in displacements induced by a variable IAR. This embodiment of the subject invention provides the same motion capabilities of a moving IAR without needing to duplicate the means by which the spine generates the FSU motion.

In a specific embodiment of the subject invention, the three, spatially-independent, cylindrical joints form a kinematic chain, joined together in continuous physical linkage that is inseparable at all times and for all motions, that determines the location and orientation of the superior vertebra with respect to an inferior vertebra of an FSU. The spinal disc prosthetic can constrain the relative motion of the superior vertebra with respect to the inferior vertebra to its natural locus of motion and can maintain, through the load bearing spring and cushion elements, the correct variation in intervertebral spacing during motion (see FIGS. 6-11).

Advantageously, embodiments the subject application can provide 1) effective static load bearing through one or more spring elements, 2) hydraulic damping and shock absorption by means of hydraulic pumping action, 3) cushioning in the various joint axes conjoined with a torus-shaped, general-purpose cushion element, constrained within the device by a central cylindrical core, 4) automatic hydraulic lubrication of all joints, 5) intervertebral stability and inseparability through mechanical linkage from superior to inferior vertebral plates that prevents motion outside the normal, natural range, 6) mechanically programmable vertebral spacing under nominal compression load-bearing by appropriate selection of spring constants, height and number in the central spring element or stack, 7) 6-DOF motion tracking with variable disc height throughout the prosthesis workspace, and 8) a mechanically programmable prosthesis workspace through judicious sizing of linear and rotational joint stops. The degrees of rotation and millimeters of linear translation allowed by the joint stops can be independently specified for each cylindrical joint, enabling the invention to match the device workspace to that of the client's FSU workspace.

The motion elements of the prosthetic device of the subject invention can be fabricated of, for example, titanium steel, titanium-carbide-coated stainless steel, bio-inert hardened stainless steel, polyurethane, polyurethane thermoplastic, cobalt-chromium-molybdenum alloy, plastic, ceramics, glass, or other materials or combinations thereof. In a second embodiment, the motion elements of the prosthetic device of the subject invention can be fabricated with hardened stainless steel ball-bearings and bearing rods that can move on hardened stainless steel curvate or linear rods that fit into raceway cavities of the various titanium or plastic elements. In an alternative embodiment, a mix of polyurethane thermoplastic bearings and polyurethane, titanium, ceramics, cobalt-chromium-molybdenum alloy and titanium-carbide-coated hardened stainless steel components can be utilized. The device of the subject invention allows for joint limits and stops on all degrees of freedom, which permits mechanical programming of its workspace to match the FSU workspace. The invention can, thus, accommodate the wide variability of FSU motion at different locations within the spine and between spines of different individuals.

In one embodiment, the modular 6-DOF spatial mechanism for spinal disc prosthesis of the subject invention comprises a superior and an inferior vertebral plate (12-1 and 1-1). In a further embodiment, the spinal disc prosthesis of the subject invention comprises a flexible, boot-protected, modular and replaceable 6-DOF prosthetic disc mechanism (mechanical linkage). In one embodiment, the vertebral plates can be formed from a biocompatible material such as, for example, titanium, cobalt-chromium-molybdenum alloy, or titanium-carbide-coated stainless steel with a bone fusion matrix on the side of the plate shaped as a spherical surface to enhance surface area contact between vertebra and the vertebral plate.

Any number of existing techniques known to those with skill in the art may be used to embed the superior vertebral plate of the subject invention into the bone of the superior vertebra and the inferior vertebral plate into the bone of the inferior vertebra of an FSU. It is contemplated that such techniques are within the scope of the subject invention.

Figure 4:
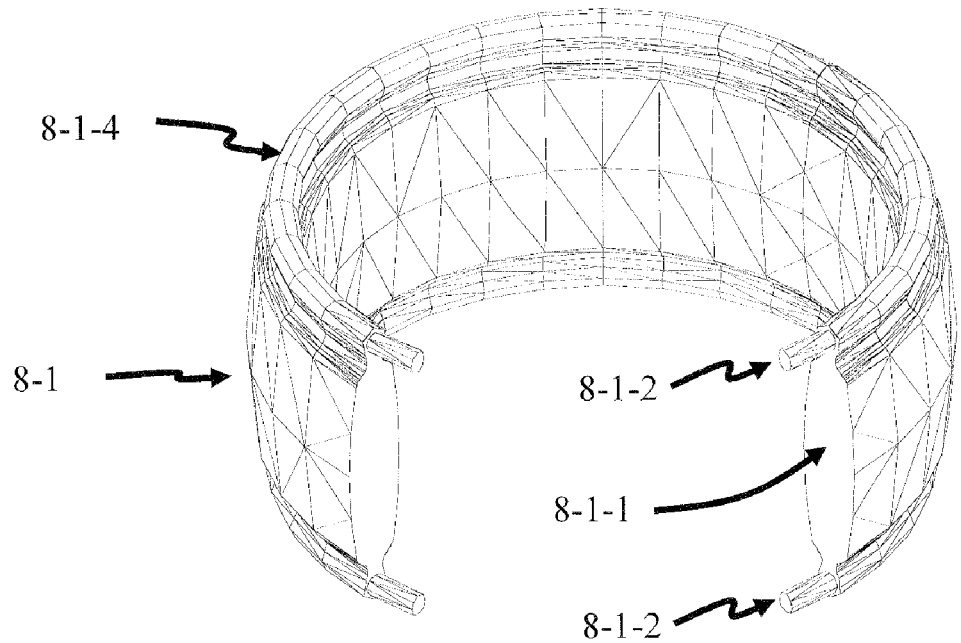
FIG. 4 shows an embodiment of clamping and reinforcing rings embedded into the boot matrix. Various fiber weaving schemes can use the rings as a starting platform for the weave.
Figure 5:
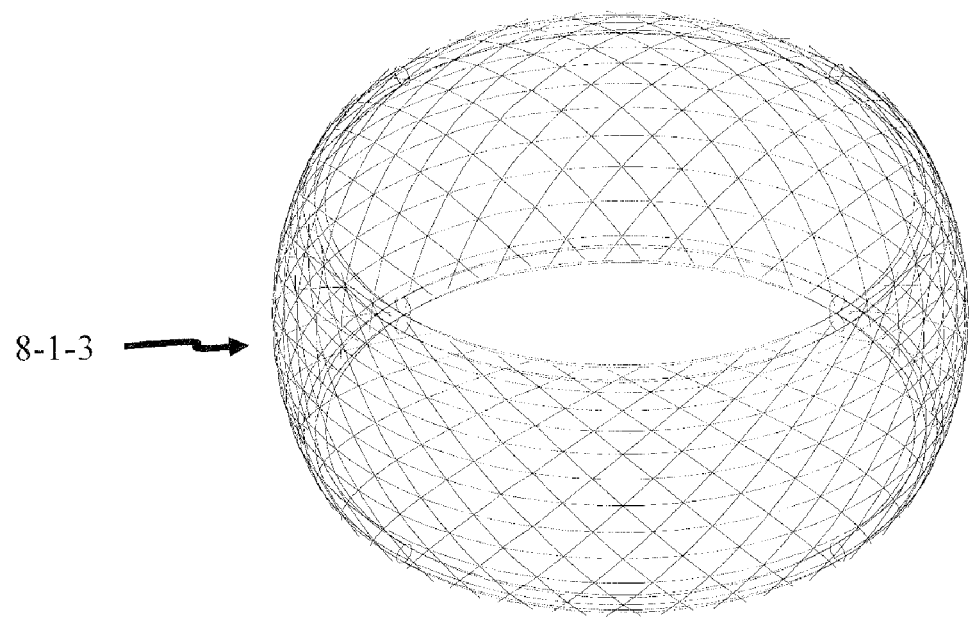
FIG. 5 illustrates a spherical cross weave 8-1-3 embodiment for a boot.
Figures 6, 7, 8:
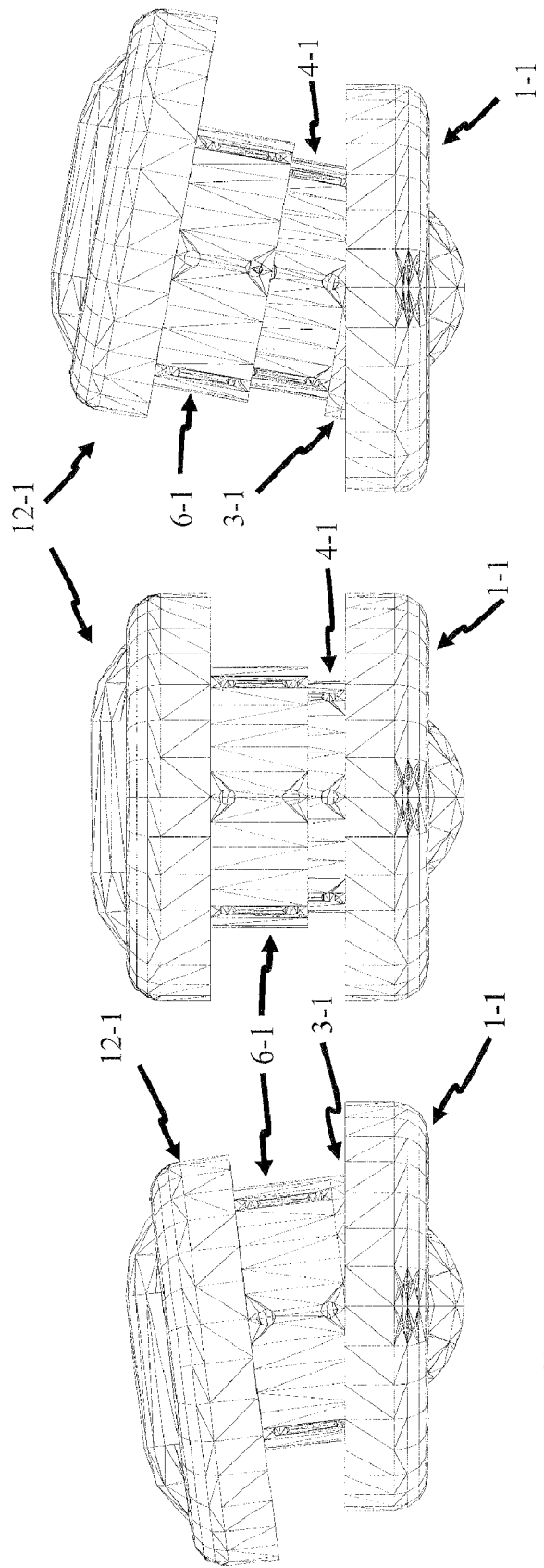
FIG. 6 shows an embodiment of the invention, without the boot, in full flexion, that is, maximum rotation of sagittal rotation cylinder 2-1 (see FIG. 9) about the sagittal axis. Note, in this embodiment, the translation and rotation of the superior vertebral plate with respect to the inferior vertebral plate and the collapse of the superior hydraulic cylinder wall 6-1 over the inferior hydraulic cylinder wall 4-1 in a telescoping manner. Also, observe that, in this position, a portion of the spring platform and hydraulic cylinder base 3-1 projects slightly above the inferior vertebral plate 1-1.
FIG. 7 portrays an embodiment of the invention, without the boot, in normal position wherein the superior 12-1 and inferior 1-1 vertebral plate parallel each other and the superior hydraulic cylinder wall 6-1 slides up to reveal some of the inferior hydraulic cylinder wall 4-1.
FIG. 8 illustrates an embodiment of the invention in full extension with the superior hydraulic cylinder wall 6-1 at its maximum extension with respect to the inferior hydraulic cylinder wall 4-1. The two cylinders have locking rings or interlocking wall projections to prevent further separation.

In a further embodiment, a flexible boot (8-1: FIGS. 1, 4, and 5) surrounds the prosthetic device of the subject invention. The boot can provide a biocompatible impermeable barrier between fluids that may be sealed within the prosthetic device and fluids within surrounding tissues, such as, for example, a silicone fluid biocompatible saline solution. In one embodiment, the boot can consist of a sturdy, flexible or elastic material, such as, for example, corrugated materials, woven fiber materials, and elastic materials, or other non-homogeneous materials. In a further preferred embodiment, the boot comprises woven, flexible fibers embedded in a strong, flexible silicon elastomer that can block fluid transfer. The embedded fiber weave, in the embodiment mentioned above, can assist in torsion loading on the prosthesis as well as loading during flexion and extension. In a further embodiment, the weave direction of the embedded fibers is diagonal relative to the central axis of a spherical or right-circular cylinder embodiment of the boot structure. In a particular embodiment, a corrugated boot, consisting of a rugged fiber elastomer designed for flexibility and toughness, assists in torsion loading on all axes and opposes extension under nominal conditions, thus, reducing nominal spinal muscle stress in the neutral position. In a further embodiment, one or more joint limit stops can be utilized on one or more of the rotational joints of the invention to limit the amount of torsion the boot can experience, reducing the possibility of tears from overstress.

All displacements and rotations of the joints can be mechanically programmed to specific joint limits by appropriately installed joint stops. The joint stops can be rigid, or, to reduce wear, cushioned with materials falling within a wide range of durometer choices from 50 to 100. For the ball-bearing embodiment the rotating joint stops are inserted into the bearing raceways.

In one embodiment, the corrugated boot has asymmetric thickness, using more reinforcing fiber in the posterior portion and less in the anterior portion, making the anterior portion more flexible and the posterior portion less flexible, but stronger and more durable. This configuration can reduce interaction with the spinal column or nerve ganglia when the boot is expanding and/or contracting. For example, as the FSU flexes, the boot can contract, primarily the highly flexible thinner sections. In a neutral position of the FSU, the boot can be under slight tension. At maximum compression of the FSU, the boot can bulge from hydraulic pressure and expanding cushioning material inside the device; however, without those pressures the boot would be slack. At maximum extension, the boot stretches, from its neutral position. In one embodiment, at maximum extension, the boot stretches an additional 20% in its anterior portion and about 10% or less in the posterior.

Figure 51:
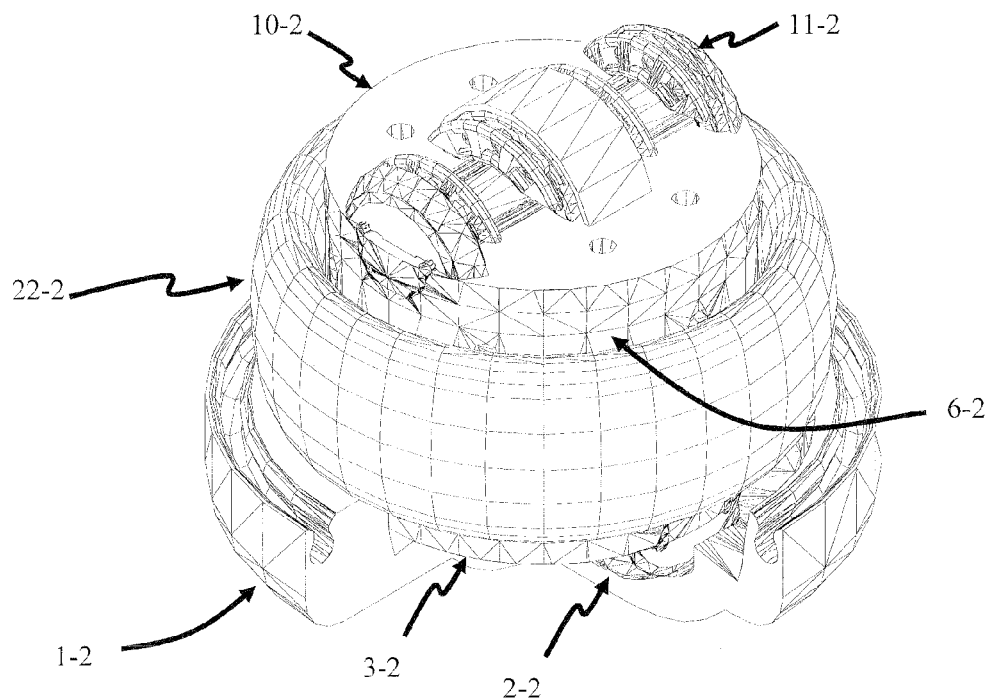
FIG. 51 illustrates a perspective view of an embodiment of a toroid belt cushion 22-2 that can be utilized with embodiments of the subject invention. In this view, the superior vertebral plate 12-2 and boot 8-1 have been removed and a quadrant of the inferior vertebral plane 1-2 excised. The toroid belt can assist with cushioning off-axial axis compressive motions of the superior vertebral plate with respect to the inferior vertebral plate and helps relieve shear stresses.
Figure 52:
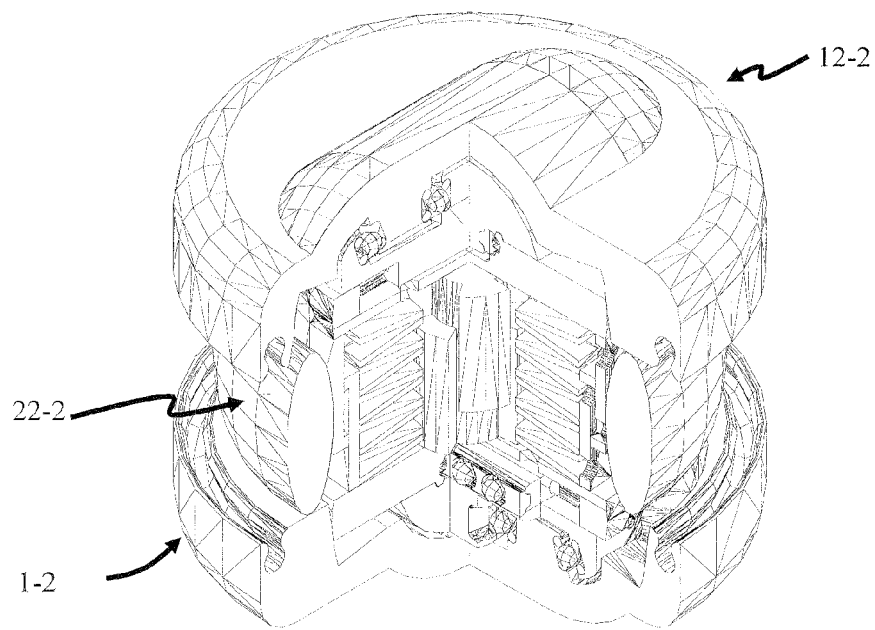
FIG. 52 depicts a toroid belt cushion element 22-2 of FIG. 5 in a quadrant cutaway perspective of the entire device with the boot removed.

A further embodiment utilizes a fibrous belt or toroidal tube 22-2 (FIGS. 51 and 52) as an additional cushioning element in the subject invention to assist the boot and central cylindrical joint in resisting shocks and arbitrary FSU force loads by compressing sections of the toroid. In one embodiment, the toroidal tube 22-2 is filled with compressible fluids or gels, such as, for example, hydrophilic gels or hydrogels. In an alternative embodiment, the toroidal tube 22-2 is a solid material. This belt can wrap around the central hydraulic cylinder elements and be confined to the disc volume by same. In a further embodiment, a toroidal belt or tube can float, not be fixed to any other elements. In an alternative embodiment, a toroidal belt can attached one or both of the vertebral plates. In a still further alternative embodiment, a toroidal belt can be integrated into the boot. With this embodiment, the boot and toroidal belt resembles the concept of fiber ring and cushion element as instructed by Casutt (U.S. Pat. No. 6,645,248B2). In one embodiment of the subject invention, the toroidal belt moves about with the central hydraulic cylinder as the cylinder translates axially, laterally or sagittally with respect to the vertebral plates. The toroidal belt can oppose the cylinder motion in all cases since it either pushes against the boot when not fixed to any elements or, if fixed to the vertebral plates, the belt pulls against those plates. Effectively, in either case, the toroidal belt can provide a three-dimensional, universal resilient or spring-like action opposing the cylinder motion. The belt can also strengthen the central hydraulic cylinder walls to provide additional sheer stress tolerance for the device.

In a further embodiment, a lubricating fluid is contained within the prosthetic device of the subject invention by the impermeable boot seal. The lubricating fluid can be pumped through fluid portals, or otherwise moved around the elements of the device, by the piston action of the superior and inferior hydraulic cylinders during spinal motion. These cylinders can further contain spring 9-1 and cushioning elements 15-1 (FIG. 11) to provide a spring-dashpot action during FSU motion.

In one embodiment, the spring-dashpot element of the central cylindrical joint element consists of superior and inferior external walls that slide over one another in a telescoping manner with retaining rings that prevent separation. The external walls enclose a cavity that can be cylindrical in shape. The superior and inferior external walls can have corresponding segmented-wall inner cores that slide past one another as the external walls slide to and fro. The inner segmented walls mesh without interference with one another. Each gap in the superior inner core wall is matched by a solid wall segment in the inferior wall, and vice versa. The preferred number of segments can be three or more and be cut from a solid cylindrical shape with a partial cavity, thus, forming supporting inner center posts to the segmented walls. The center posts of the inner core elements, top and bottom, can partially consist of cushion elements mounted on rigid elements to further promote shock absorption. The external walls and the segmented-wall internal cores can, together, firmly hold one or more spring elements in place, for example, a stack of Bellville springs, in a variety of series/parallel spring configurations within the available cavity space of the central hydraulic cylinder. The number, arrangement and spring rates of the Belleville springs in the stack will determine the intervertebral spacing when the invention is under load in the spine. This means the invention can accommodate a wide variety of practical situations by the simple expedient of changing the composition of the spring stack during manufacture, leading to easily produced different model numbers. In this way, the invention can compensate for client needs without changing the design and structure of any of the invention elements. In effect, in the preferred embodiment, only the spring stack composition changes for a wide range of models.

The walls of the superior and inferior cylindrical elements, along with the spring, can constitute a spring-dashpot shock absorbing system. Hydraulic portals within the device can facilitate shock absorbing characteristic while at the same time forcing a bio-lubricant to flow through and around the components of the bearing interfaces of the device. The combined dual cylinder and the spring stack provide a column element that resists shear forces and promotes the rotation and translation of the various joint elements when the FSU is subjected to shear forces.

In one embodiment, the inferior hydraulic cylinder telescopes in and out of the superior hydraulic cylinder during flexion and extension. Lateral and other motions can also affect the amount of telescoping, which accommodates, up to joint limits, the natural dictates of the FSU motion. In a further embodiment, the superior and inferior hydraulic cylinders have guard-rings or edges (4-1-2, FIG. 19 and 6-1-2, FIG. 18) to keep them from separating at maximum extension, thus preserving the mechanical linkage or inseparable connection between the vertebrae of the FSU. In a still further embodiment, the guard-rings or edges do not have to extend all the way around the cylinder, but can be segmented to occupy, only every other 60 degree arc around the cylinder wall. This allows the cylinder walls to be thicker and stronger in those 60 degree segments where there is no edge, guard-ring, or bearing.

Figure 53:
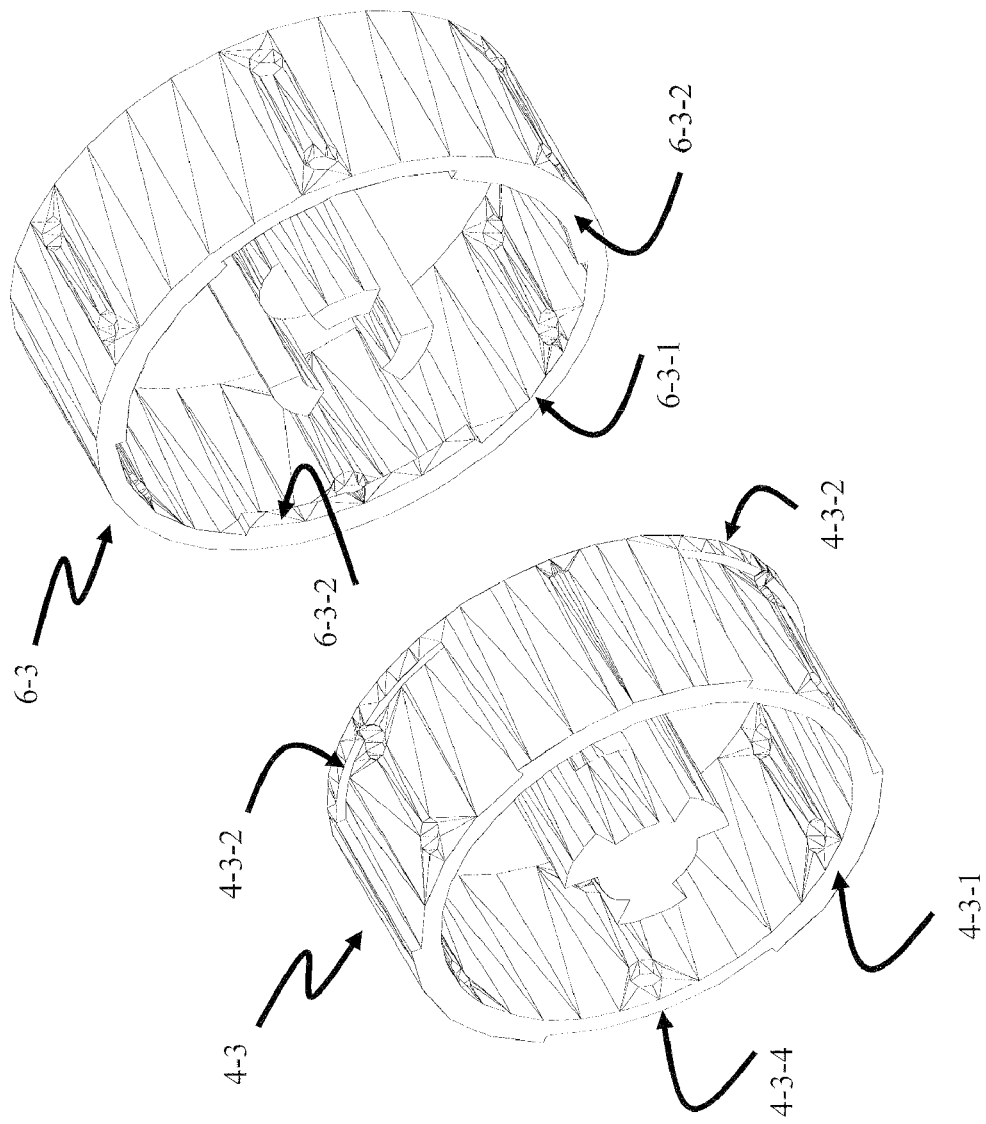
FIG. 53 shows a perspective view of a further alternative embodiment of the inferior and superior hydraulic cylinder shells 4-3 and 6-3. In a particular embodiment, shell 4-3 has three 60 degree, thick-wall segments 4-3-1 and three 60 degree, thin-wall segments 4-3-4, with guard ring segments 4-3-2 for each of the three thin-wall segments. Shell 6-3 can have a single thin-wall segment 6-3-1, with guard ring segments 6-3-2 associated with, and conforming to, each of the guard rings 4-3-2 at the top of each of the three thin-wall segments 4-3-4 of the inferior hydraulic cylinder shell. The thick-walled segments 4-3-1 of shell 4-3 add greater strength to the central hydraulic cylinder, and example of which is shown in FIG. 35 for the higher order bearing version.

FIG. 53 shows a perspective view of an embodiment of the inferior 4-3 and superior 6-3 hydraulic cylinder shells. In this embodiment, 4-3 has three 60 degree, thick-wall segments 4-3-1 and three 60 degree, thin-wall segments 4-3-4, with guard ring segments 4-3-2 for each of the three thin-wall segments. Shell 6-3 has only a single thin-wall segment 6-3-1, with guard ring segments 6-3-2 associated with, and conforming to, each of the guard rings 4-3-2 at the top of each of the three thin-wall segments 4-3-4 of the inferior hydraulic cylinder shell. The thick-walled segments 4-3-1 of shell 4-3 can add greater strength to the central hydraulic cylinder while still providing axial slider joint limits using the guard ring segments 4-3-2 in the three 60 degree segments 4-3-4 that have matching guard ring segments 6-3-2 at base of 6-3. In this arrangement there is no sacrifice in the wall thickness of 6-3. The compromise is that the guard rings span only 180 degrees of the walls circumference. This should not affect the joint limit stop function. In a further embodiment, the guard rings can be approximately ¼ to ½ the thickness of a wall segment.

In a further embodiment of the subject invention, hydraulic portals 3-1-3, 4-1-3, 6-1-3, and 10-1-3 (FIGS. 13 and 19) through the various surfaces allow transfer of fluid into and out of the telescoping cylinders. The hydraulic fluid, which can be pumped under pressure by the natural action of spinal flexion and extension, tends to separate all the interacting bearing surfaces in a manner similar to the action of synovial fluid in a diarthrodial joint; this can increase the efficiency of the bearing surface and reduce wear. Such fluids can include, but are not limited to a biocompatible silicone fluid, a biocompatible saline solution, oils of various types and viscosities, water, gels, other viscous materials, or combinations thereof.

The subject invention provides a spinal disc prosthesis (FIGS. 2, 14, and 30) capable of providing spatial movement with up to 6 independent degrees of freedom. The modular prosthetic disc of the subject invention contains the mechanisms responsible for its general motion capability. In a further embodiment, the prosthesis can be surrounded by an impermeable boot 8-1 consisting of a resilient, fiber-reinforced elastomer matrix that firmly attaches to the superior and inferior vertebral plates 12-1 and 1-1. In a particular embodiment, the boot fiber weave is diamond shaped and can be woven into cylindrical or spherical 8-1-3 form (FIG. 5) or in bellows form (not shown). Various types of reinforcing materials, weave type, and the fiber properties, along with mixed fibers can be used to construct the boot, much as tire making in the automotive industry. The boot structures can further have reinforcing rings 8-1-2 at the top and bottom. These rings with surrounding fiber and elastomer attach fixedly to 12-1 and 1-1 in any number of methods known to a person with skill in the art. In a particular embodiment, a channel 12-1-6 and 1-1-6 can be configured to clamp onto the rings, so the boot can withstand large forces without tearing the boot matrix or pulling boot away from the device. The boot can be shaped as in 8-1-1, to provide addition cushioning effect. The boot can also block out bio-debris that might reduce joint mobility.

Figure 28:
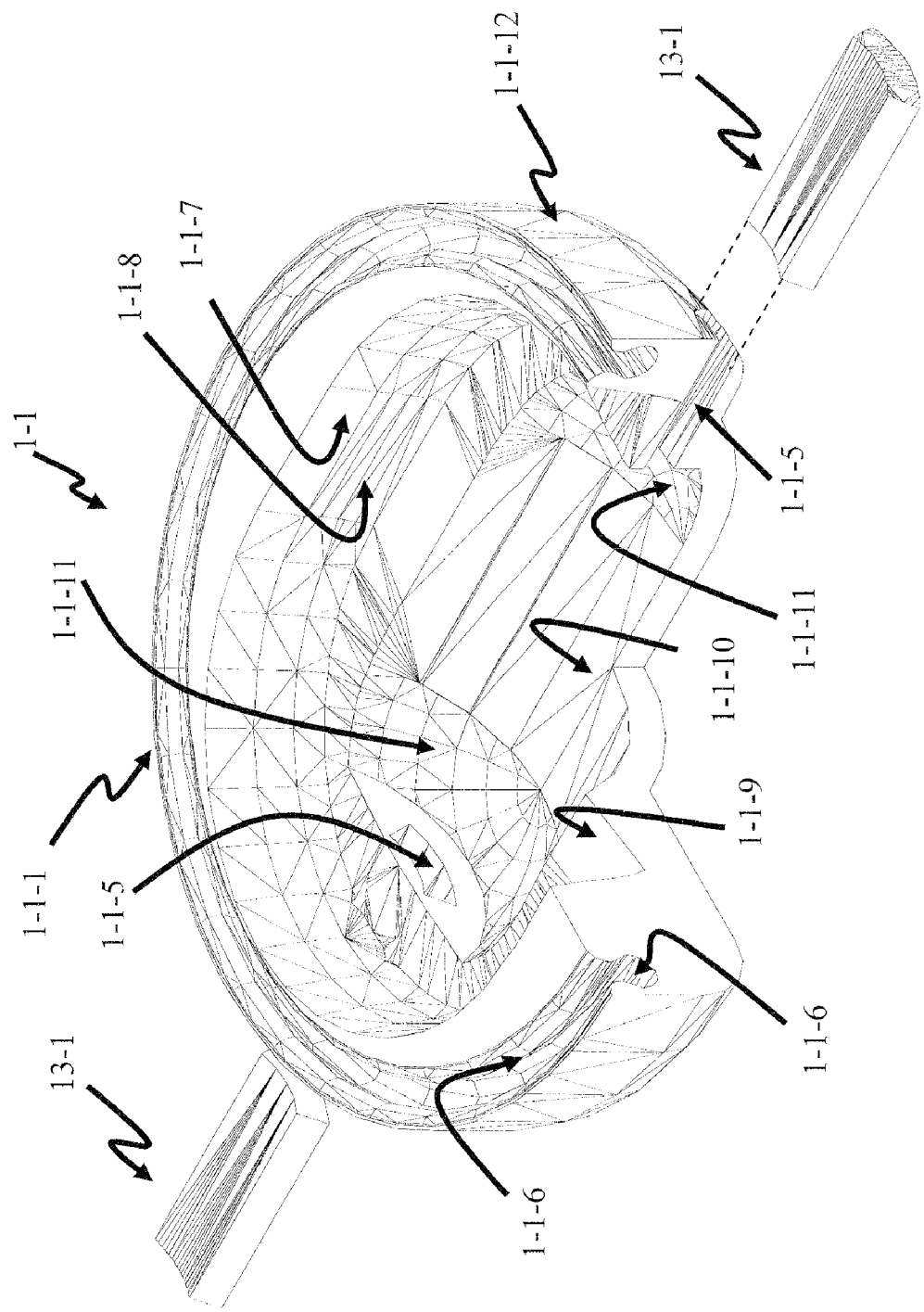
FIG. 28 provides a quadrant, perspective cutaway view to illustrate the various features and surfaces of an embodiment of the inferior vertebral plate 1-1. In a further embodiment, the superior vertebral plate underside matches the topside shown here. However, the sagittal cylinder socket 1-1-10 and 1-1-11 is oriented at 90 degrees to lateral cylinder socket 12-1-10 and 12-1-11 in the superior vertebral plate 12-1 (see FIG. 16).

In a specific embodiment, principal mechanisms of the subject invention consists of three, spatially-independent cylindrical joints, for general positioning and orienting in three-dimensional space, that establish an inseparable kinematic chain or kinematic linkage between a superior vertebral plate (12-1, FIG. 16) and an inferior vertebral plate (1-1, FIG. 28). The inferior vertebral plate 1-1 and superior vertebral plate 12-1, in an embodiment, can be identical. More specifically, 1-1 can be 3-dimensionally congruent to 12-1, i.e. there exists a rigid body transformation that will allow one to superimpose 1-1 onto 12-1. In certain embodiments described herein, a statement regarding the features of one, therefore, applies to the other in such an embodiment. For example, surfaces 12-1-1, 12-1-2, 12-1-3, and 12-1-4 can be constructed to enhance bone fusion to 12-1. This observation also applies to corresponding surfaces (not labeled) of 1-1.

Figure 15:
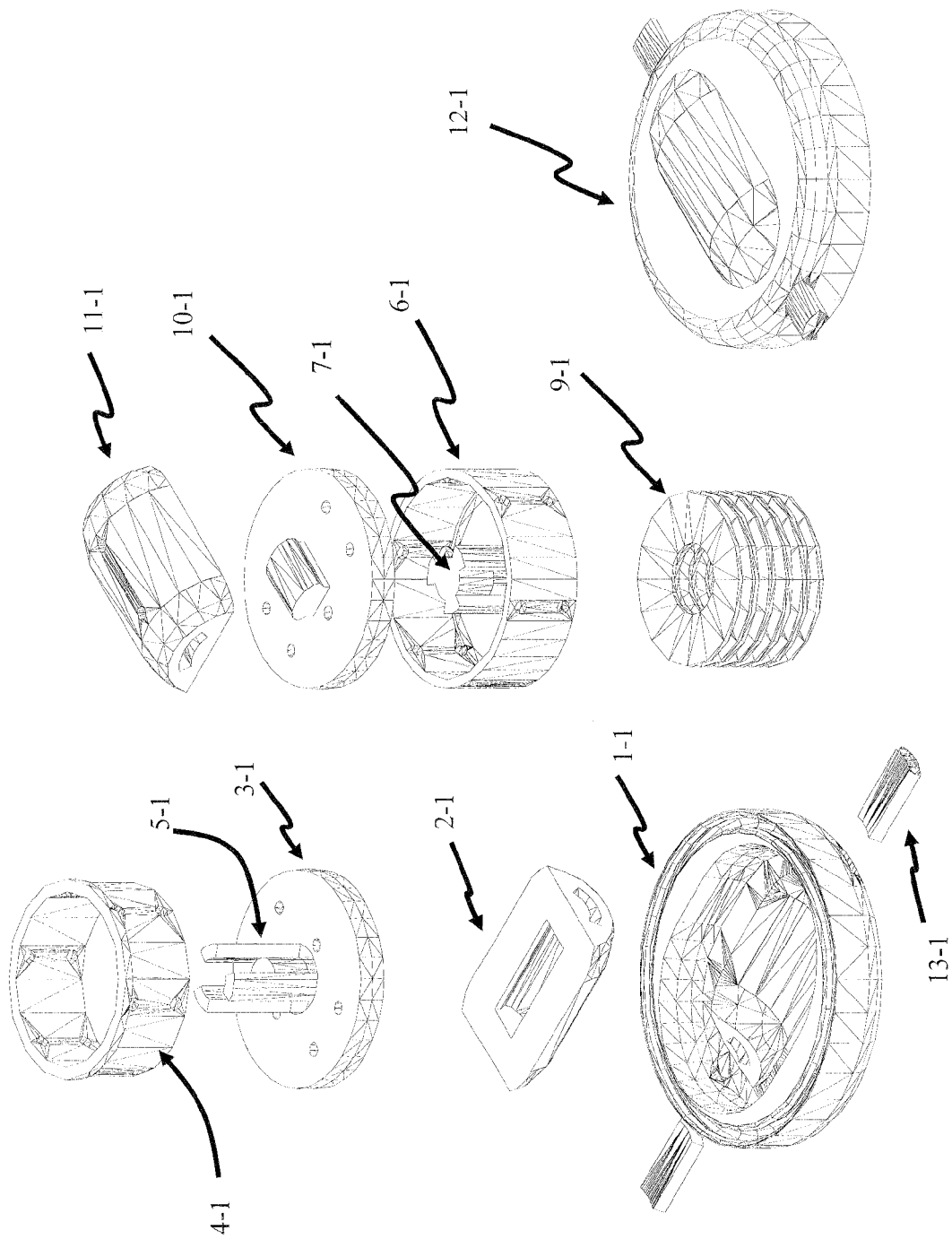
FIG. 15 shows, in exploded perspective view, all the elements of a particular embodiment of the subject invention except the boot, a toroidal belt, and various cushioning structures that can be used within the mechanism.
Figure 22:
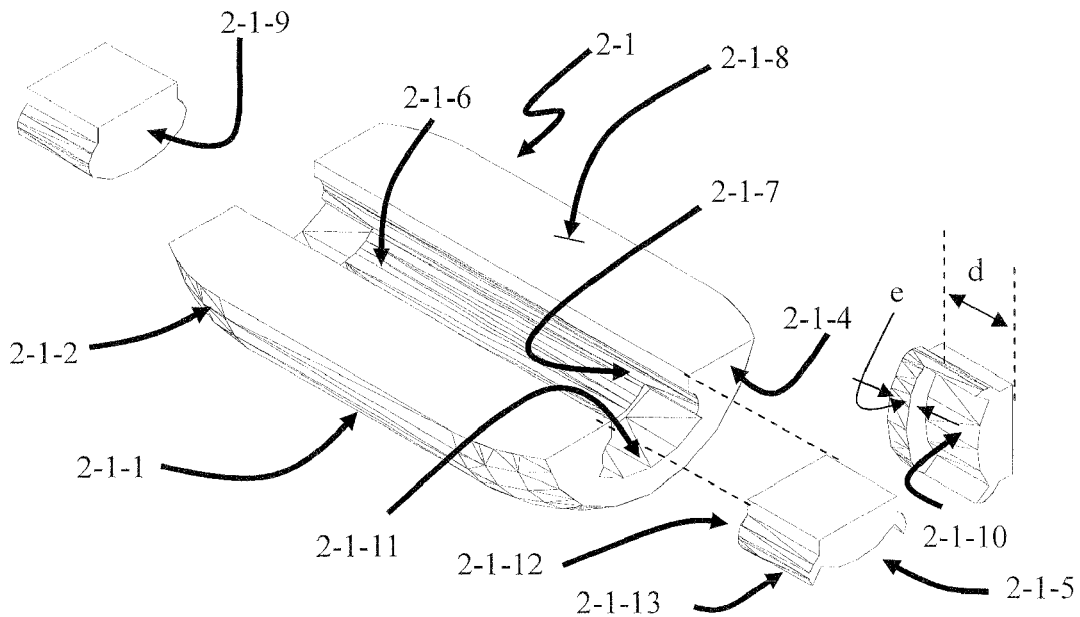
FIG. 22 illustrates the principal features of the sagittal rotation cylinder, which, in one embodiment, is identical in structure to the lateral rotation cylinder. This view shows what would be the other side of the lateral rotation cylinder in FIG. 17. The concavity 2-1-6 is a bearing raceway with bearing stops 2-1-12. These bearing stops support a curvate concavity 2-1-5 through which the cylinder can rotate freely about conforming surfaces on the lock keys.

In a particular embodiment, each cylindrical joint provides one independent rotational and one independent linear translational degree of freedom with mechanically programmable joint stops and the means for load bearing elements for each degree of freedom. The sagittal rotation cylinder 2-1 (FIG. 22) and the lateral rotation cylinder 11-1 (FIG. 17), appear in context in FIGS. 13, 14, and 15. The third cylindrical joint, also referred to herein as the central hydraulic cylinder, can be configured from the inferior hydraulic cylinder, consisting of elements 3-1, 4-1, and 5-1, and the superior hydraulic cylinder, consisting of elements 6-1, 7-1, and 10-1.

Figure 16:
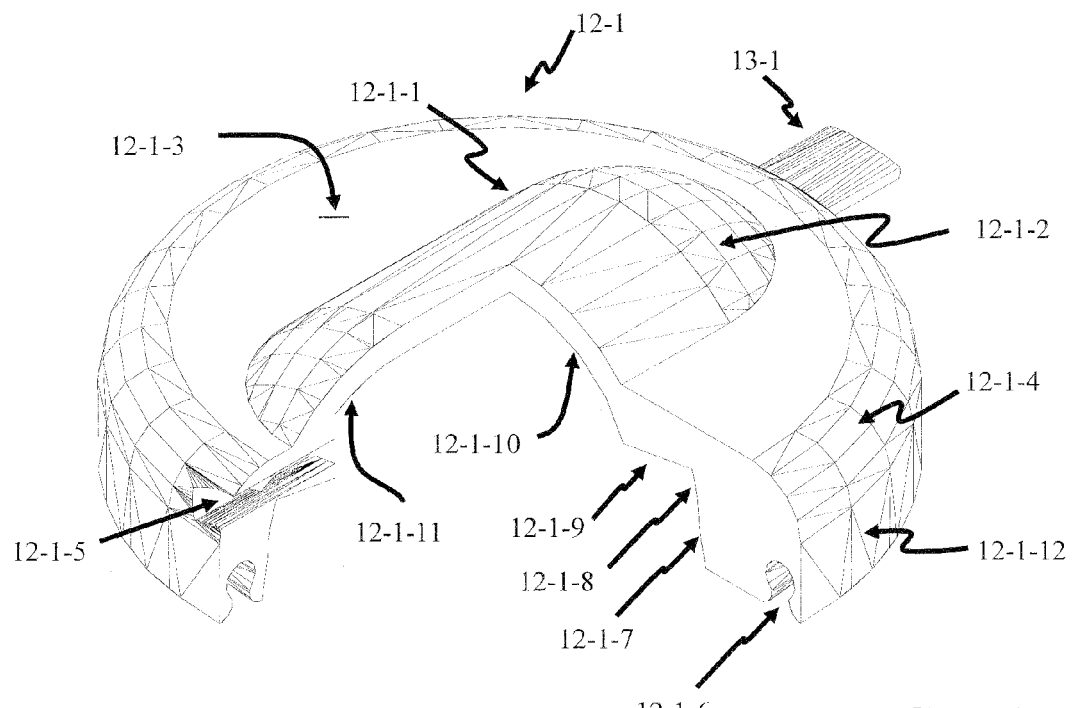
FIG. 16 is a perspective view of an embodiment of the subject invention from the top of the plate with a quadrant cut out that allows one to observe the different structures and surfaces of the superior vertebral plate.

In a further embodiment, the lateral rotation cylinder 11-1 (FIG. 17) fits into a conforming cavity in the superior vertebral plate 12-1 (FIG. 16). In a still further embodiment, the cylindrical cavity 12-1-10 conforms to the cylindrical surface 11-1-1 and the spherical cavities 12-1-11 at each end conforms to the spherical surfaces 11-1-2 at each end of 11-1. These cavities and surfaces can all have centers of rotation on the lateral axis 17-1. As mentioned above, hydraulic portals 11-1-3 pass lubricating fluid under pressure to the joint surfaces.

In another embodiment, the surfaces 11-1-4 at each end of cylinder 11-1 are matched by surfaces at the end of the superior vertebral plate's cylinder cavity, planar in a preferred embodiment. A curvate slot 12-1-5 allows press-fit insertion of lock keys 13-1 through plate 12-1. The key length is such that it projects into the slightly oversized curvate cavity 11-1-5 of the lateral cylinder raceway plug 11-1-12. The surface 13-1-4 at the other end of the key conforms to the surface 12-1-12 of the superior vertebral plate.

Figure 12:
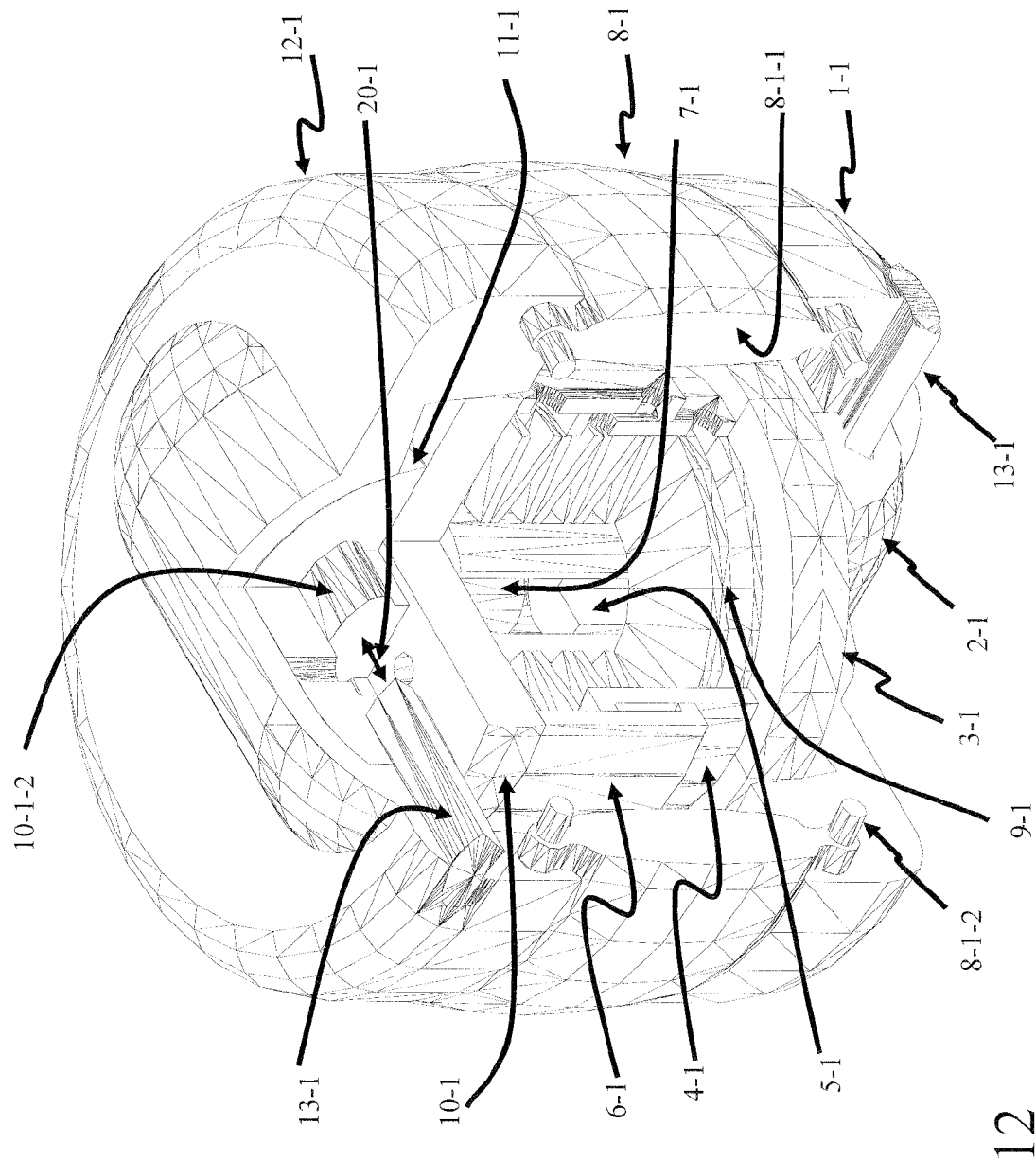
FIG. 12 is a quadrant cutaway of a perspective view of an embodiment of the assembled invention, which exposes most of the invention's principle elements.

The superior hydraulic cylinder plate 10-1 (FIG. 18), using slide bearing block 10-1-2 fixed to its top and with locking projection 10-1-5, can be slid into the lateral raceway 11-1-6 (FIG. 18), where locking edge cavities 11-1-7 can conform to projections 11-1-5, forming a lateral prismatic joint with plus or minus displacement 20-1 (FIG. 12). A corresponding displacement can be applied to the sagittal prismatic joint. The latter is not shown for this embodiment, but the sagittal prismatic displacement 20-2 of the ball-bearing embodiment, FIG. 29, demonstrates the idea. After sliding 11-1 onto an already assembled central hydraulic cylinder by means of bearing block 10-1-2 fixed on top of plate 10-1 and inserting the subassembly into the lateral rotation socket of 12-1 described earlier, assembly can proceed with positioning the lock keys 13-1 through the superior vertebral plate slot 12-1-5 and loosely into the oversized cavities 11-1-5 at either end of the lateral rotation cylinder. In one embodiment, the lock keys are press-fit into position. The slots 11-1-5 allow the lateral cylinder to rotate about the keys that project into the cylinder ends. An end-on, perspective view is shown for the sagittal rotation cylinder in FIG. 24. In one embodiment, the maximum value of angle $\gamma$ can be 15 degrees. The actual size of $\gamma$ dictates the maximum rotation joint range, namely, $2\gamma$ degrees. Shims can be placed in the slot on either side of the center position to limit rotation to less than the maximum for that side. Further, the range about center can be unequal by appropriate shims. A similar observation applies to the lateral rotation cylinder.

After the lateral rotation cylinder 11-1 mates with the central hydraulic cylinder, but before the lock keys 13-1 are positioned in slot 12-1-5, both ends of the lateral rotation cylinder 11-1 can be sealed with raceway plugs 11-1-12 into cavities 11-1-5 with upper curvate surface 11-1-11 and lower curvate surface 11-1-10. In one embodiment, the raceway plugs 11-1-12 are inserted in the ends of the lateral rotation cylinder 11-1 by press fitting. In another embodiment, upper curvate surface 11-1-11 and lower curvate surface 11-1-10 are cylindrical with the center of curvature on the lateral axis 17-1. Flange 11-1-13 on the plug can increase surface area contact with the bearing raceway cavity 11-1-6. Further, top curvate surface 11-1-1 can conform to curvate surface 13-1-1 as can 11-1-10 and 13-1-2, allowing the cylinder to rotate about the lock keys from the common centers on the lateral axis 17-1. The planar surfaces 13-1-2 of the keys conform to those found at the sides of cavity 11-1-5. In a further embodiment, the length d of plug 11-1-12 (shown for the corresponding sagittal plug 2-1-12 in FIG. 22) fixes the displacement 20-1, allowing mechanical programming of the displacement using different length plugs. In a still further embodiment, a parameter e of the plug fixes the length of the cavity 11-1-5 (only shown for the sagittal plug 2-1-12 and its cavity 2-1-5, FIG. 22).

In yet another embodiment, a sagittal rotation cylinder 2-1 (FIGS. 22 and 23) provides similar features and functions for sagittal rotation and translation as the lateral rotation cylinder 11-1 does for lateral rotations and translations. In this embodiment, the sagittal rotation cylinder 2-1 fits into a conforming cavity in the inferior vertebral plate 1-1 (FIG. 28). In a further embodiment, the cylindrical cavity 1-1-10 conforms to the cylindrical surface 2-1-3 and the spherical cavities 1-1-11 at each end conforms to the spherical surfaces 2-1-2 at each end of 2-1. In a still further embodiment, these cavities and surfaces all have centers of rotation on the sagittal axis 16-1.

In another embodiment, the surfaces 2-1-4 at each end of cylinder 2-1 are matched by conforming surfaces at the end of the inferior vertebral plate cylinder cavity, planar in a preferred embodiment. A curvate slot 1-1-5 allows positioning of lock keys 13-1 through plate 1-1. In one embodiment, the lock keys are press-fit into the curvate slot. The key length can be such that it projects into the slightly oversized curvate cavity 2-1-5 of the sagittal cylinder raceway plug 2-1-12. The surface 13-1-4 at the other end of the key can also conform to the surface 1-1-12 of the superior vertebral plate.

Figure 24:
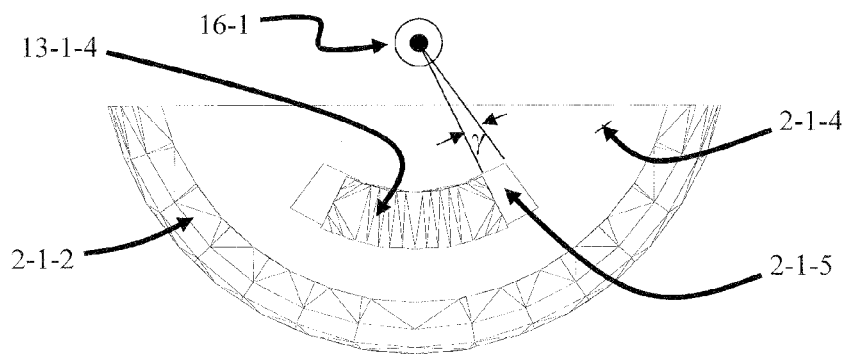
FIG. 24 is a perspective end-view of the sagittal rotation cylinder shown in FIG. 23. In this embodiment the lock key 13-1 has 2γ degrees of clearance in the bearing stop slot 2-1-5, permitting ±γ degrees of rotation of the cylinder about the lock key. Only the end surface 13-1-4 of lock key is visible from this perspective. The rotational joint formed by the lock key and the bearing stop forms a lower order pair. The axis of rotation 16-1 of the cylinder is out of the page.

By way of a non-limiting example, the superior hydraulic cylinder plate 3-1, can utilize slide bearing block 3-1-2 fixed to its top and with locking projection 3-1-5, and slide into the sagittal raceway 2-1-6, where locking edge cavities 2-1-7 can further conform to projections 3-1-5, forming a sagittal prismatic joint whose displacement equals the length of 2-1 minus twice the length d of plug 2-1-12. After sliding 2-1 onto an already assembled central hydraulic cylinder by means of plate 3-1 and inserting the subassembly into the sagittal rotation socket of 1-1 described earlier, assembly can proceed with positioning of the lock keys 13-1 through the superior vertebral plate slot 1-1-5 and loosely into the oversized cavities 2-1-5 at either end of the sagittal rotation cylinder 2-1. The slots 2-1-5 allow the sagittal cylinder to rotate about the keys that project into the cylinder ends. An end-on, perspective view is shown in FIG. 24. The angle $\gamma$ allows the cylinder to rotate $\pm\gamma$ degrees about the sagittal rotation axis 16-1. In one embodiment, the maximum value of angle $\gamma$ can be 15 degrees. Slots with smaller values $15 > \gamma > 0$ can be used in a particular embodiment. The actual size of $\gamma$ dictates the maximum rotation joint range, namely, $2\gamma$ degrees. Shims can be placed in the slot on either side of the center position to limit rotation to less than the maximum for that side. Further, the range about center can be made unequal by inserting more shims on one side of the slot than on the other side. After the sagittal rotation cylinder 2-1 mates with the central hydraulic cylinder, but before the lock keys 13-1 are positioned into 1-1-5, both ends of the sagittal rotation cylinder 2-1 can be sealed with raceway plugs 2-1-12 into cavities 2-1-5 with upper curvate surface 2-1-11 and lower curvate surface 2-1-10. In one embodiment, these surfaces are cylindrical, with center of curvature on the sagittal axis 16-1. In addition, flange 2-1-13 on the plug can increase surface area contact with the bearing raceway cavity 2-1-6. Curvate surface 2-1-11 can conform to curvate surface 13-1-1 as can 2-1-10 and 13-1-2, allowing the cylinder to rotate about the lock keys from the common centers on the sagittal axis 16-1. The planar surfaces 13-1-2 of the keys can also conform to those found at the sides of cavity 2-1-5. The lengths d of bearing plug or stop 2-1-12 in FIG. 22 can fix the sagittal slider displacement, allowing mechanical programming of the displacement using different length plugs. A parameter e of the plug cans also fix the length of the cavity 2-1-5.

A spring element, in a one embodiment, is a series configured spring stack (9-1) of up to 10 Belleville springs (9-1-1), loosely fit (FIGS. 12 and 14) within the central hydraulic cylinder formed from superior elements 10-3, 6-1, and 7-1 and inferior elements 3-1, 4-1, and 5-1. In a particular embodiment, the Belleville springs are of a bio-inert material. Other embodiments can configure combinations of series and parallel stacks with varying spring constants to provide non-linear spring performance when the springs are allowed to saturate, i.e. reach their maximum allowed deflection and, thus, operate the stack out of its linear range. For example, as Belleville springs with smaller spring constants reach maximum deflection, the overall spring constant will increase.

Figure 19:
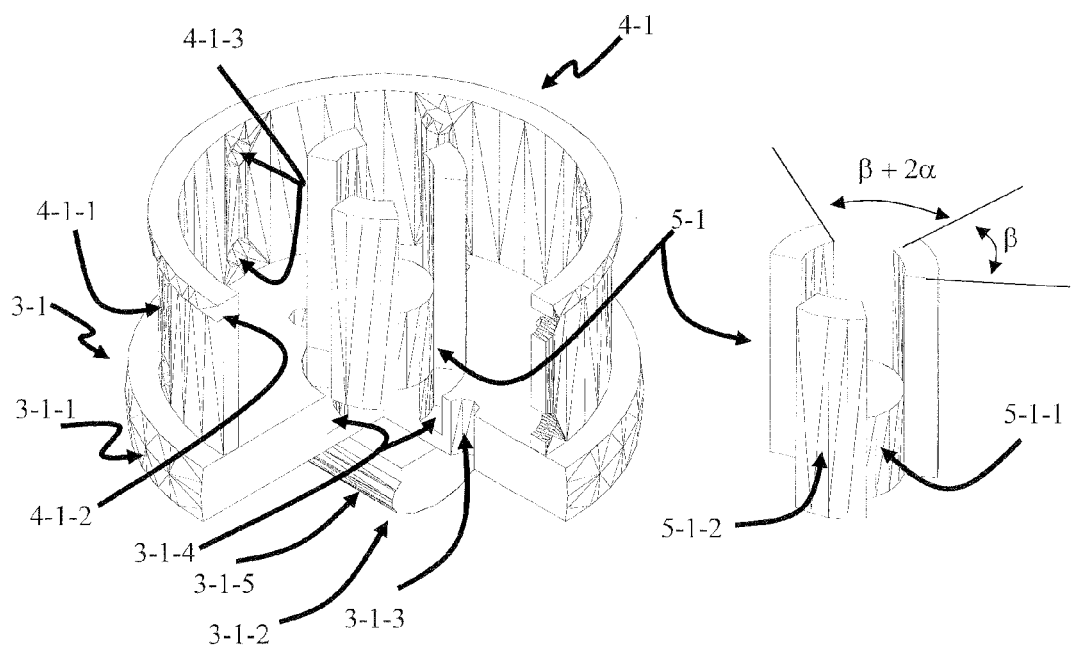
FIG. 19 details an embodiment of an inferior hydraulic cylinder wall 4-1, its interior core 5-1, the walled segments 5-1-2 of the inferior inner core.
Figure 20:
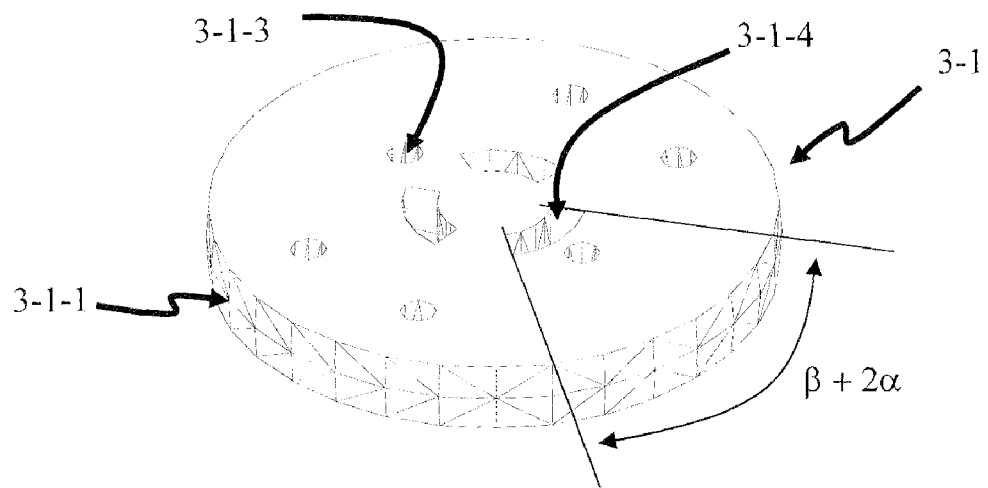
FIG. 20 illustrates various features of an embodiment of the spring base 3-1 that can be utilized with an embodiment of the subject invention, which, in this embodiment, simultaneously serves as the inferior hydraulic cylinder wall base and spring element platform.
Figure 21:
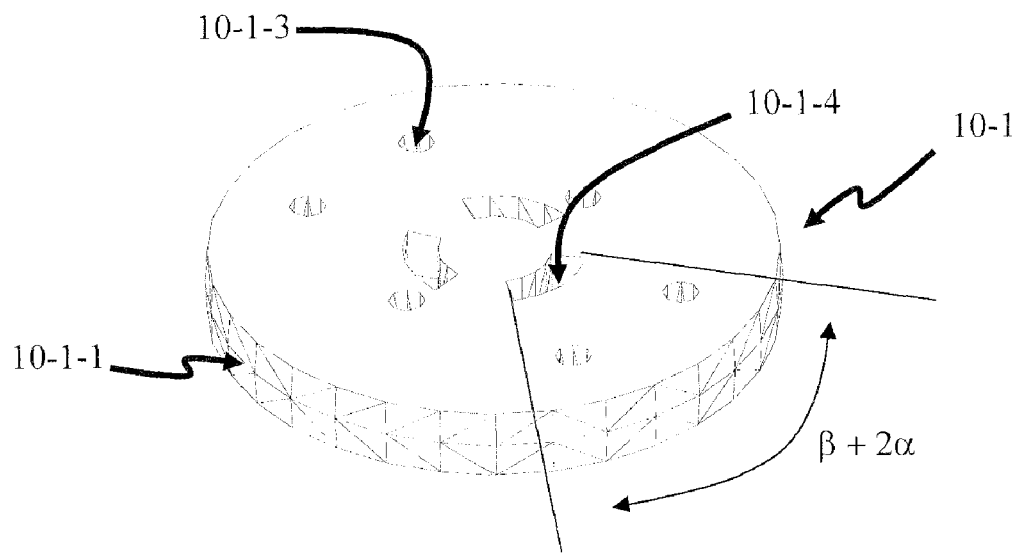
FIG. 21 shows the undersurface features of the top cover 10-1 of the superior hydraulic cylinder wall. In this embodiment, the hydraulic portals 10-1-3 have a 90 degree rotation to similar elements 3-1-3 and the indented wall-slots 10-1-4 have a $\beta+2\alpha$ rotation with respect to similar element 3-1-4 on the base 3-1. This arrangement of wall slots allows the walled segments of the inferior (superior) inner core to slide into the wall-slots of element 10-1 (3-1) without interference. The walls subtend an angle $\beta$ and the maximum angle of rotation about the axial axis through the center of the top cover and spring base equals $2\alpha$, or $\pm\alpha$.
Figures 25A, 25B, 25C:
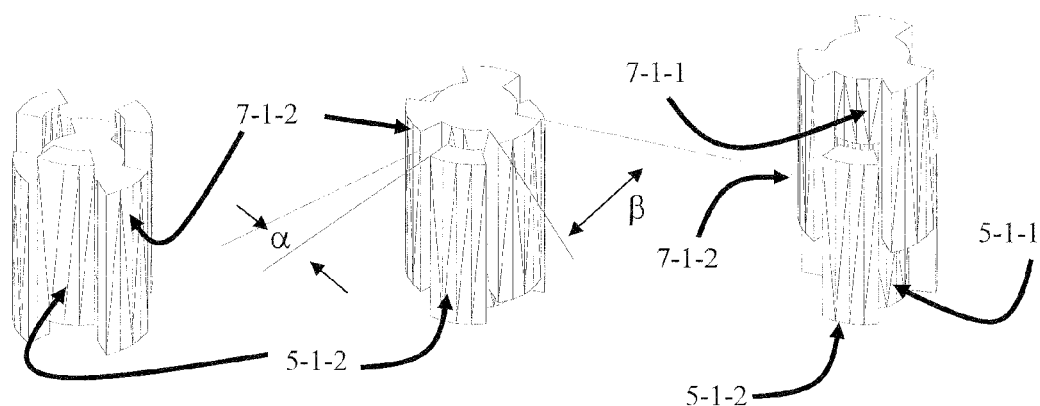
FIG. 25 illustrates how the superior segmented-wall cylinder 7-1 and the inferior segmented-wall cylinder 5-1, of an embodiment of the subject invention shown above, mesh together as the superior and inferior hydraulic cylinder walls start from full flexion a) to neutral b) and then full extension c). Stand alone drawings of 7-1 and 5-1 appear in FIG. 18 and FIG. 19. In a particular embodiment, the walled segments 5-1-2 extend into slots 10-1-4 of the top plate 10-1 of the superior when the superior hydraulic cylinder wall completely closes, as in the full flexion position of the FSU as shown in a). Similarly, the walled segments 7-1-2 extend into slots 3-1-4 of the spring base 3-1. At maximum compression and maximum extension, and all positions in between, there exists a central core of support within the inside diameter of the spring elements. The overlap in the segmented walls 7-1-2 and 5-1-2 assures this feature and that overlap requires that retaining cavities 3-1-4 and 10-1-4 be cut into plates 3-1 and 10-1 to accommodate full compression. Axial rotation is still permitted, even when the wall segments penetrate into cavities 3-1-4 and 10-1-4, as those cavities are oversized to accommodate the permitted axial rotation.

In a further embodiment, the segmented-wall inner cores 5-1 (FIG. 19) and 7-1 (FIG. 18) loosely fit into inner circular opening of the springs, allowing the cores to slide by the springs during operation while providing an intact central shaft to stabilize and hold the spring elements at all times and for all device configurations. The core wall segments 5-1-2 and 7-1-2 can form a central column to help stabilize the springs through all nominal movements of the FSU as seen in FIGS. 9-11 and 25. In this embodiment, the segmented walls slide past one another without hindrance, and, at full compression, mesh as shown in FIG. 25. The wall segments 5-1-2 that extends past core 7-1-1 are capable of fitting into slots 10-1-4 of plate 10-1. The wall segments 7-1-2 that extends past core 5-1-1 are also capable of fitting into slots 3-1-4 of plate 3-1. In one embodiment, slots 3-1-4 and 10-1-4 subtend angle $\beta+2\alpha$ in order to allow axial rotation of $\pm\alpha$, even in the fully compressed position. The central elements 5-1-1 and 7-1-1 strengthen the inner cores and can assist in resisting shear forces. The segmented walls subtend $\beta$ degrees and the gaps $\beta+2\alpha$ degrees (FIGS. 18 and 19). If 2n equals the number of walls, then preferred embodiments satisfy $2n(\beta+\alpha) = 360$ degrees. For preferred embodiments n=3 or 4, but other choices are possible. In an example embodiment n=3, 2n=6 and $\beta+\alpha=60$ degrees. For an axial rotation specification of $\pm 5$ degrees, $\alpha=5$ degrees, $\beta=55$ degrees. For an axial rotation specification of $\pm 10$, $\alpha=10$ degrees, $\beta=50$ degrees. The wall segments 5-1-2 and 7-1-2 can also act as joint stops and limit axial rotations to $\pm\alpha$ degrees, $\pm 5$ up to $\pm 10$ degrees in one embodiment.

Figure 26:
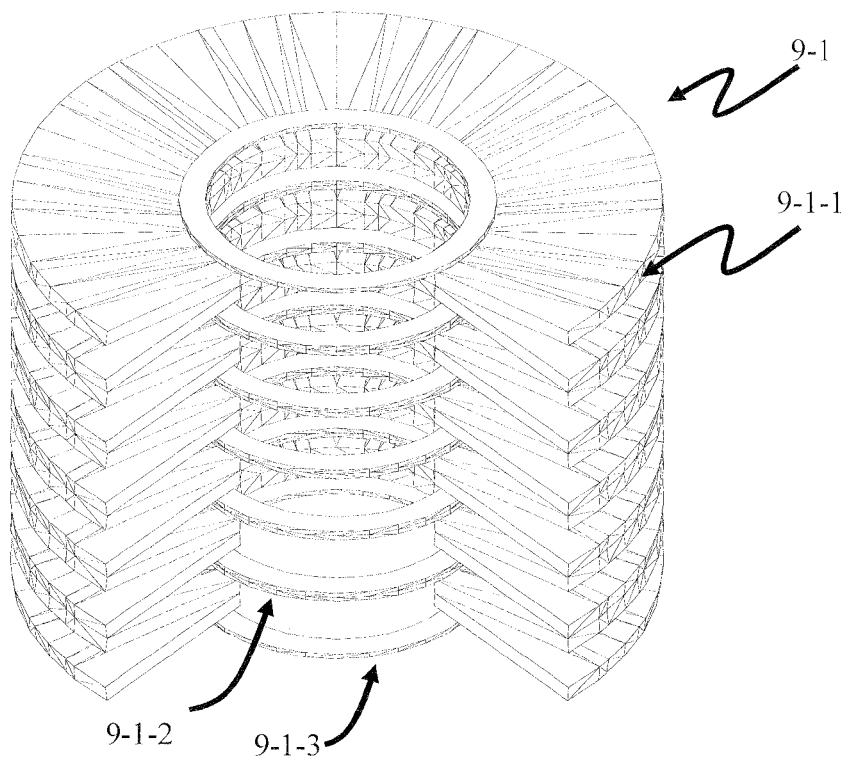
FIG. 26 shows one embodiment of the spring stack 9-1 using Belleville springs 9-1-1 in a series stack with guard rings 9-1-2 and 9-1-3. The guard rings keep series of approximately matched-pairs of Belleville springs from inverting to parallel configuration under full compression.
Figure 27:
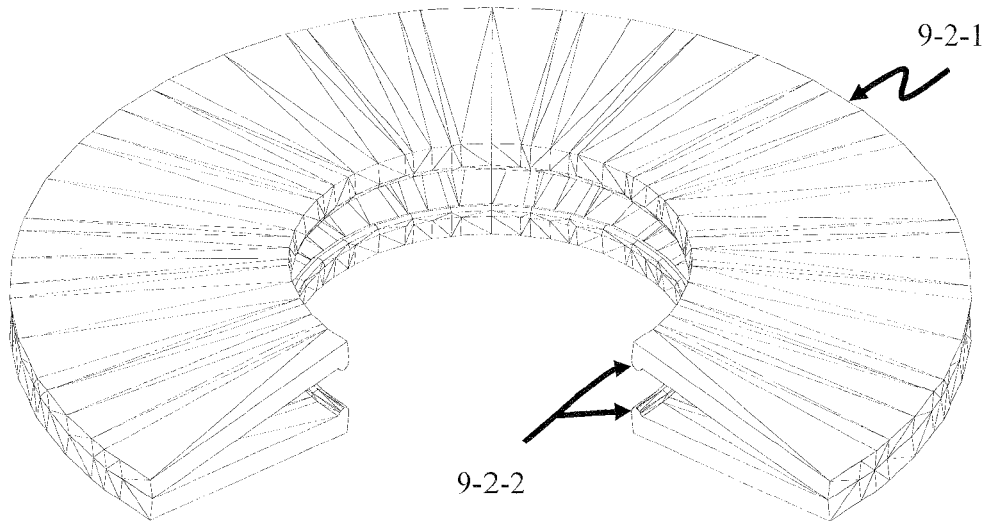
FIG. 27 demonstrates another embodiment of the subject invention utilizing a modified Belleville spring 9-2-1 comprising raised lips 9-2-2 on the edge shown. In this embodiment, when series spring configurations use approximately matched-pairs, the edges prevent complete closure under full compression and, hence, prevent inversion of a washer in the pair. The edges act in the same manner as the guard rings of the previous figure.

In one embodiment, the outer walls 4-1 of the inferior hydraulic cylinder and 6-1 of the superior hydraulic cylinder have conforming curvate shapes 4-1-1 and 6-1-1, which can also help stabilize the spring stack. In a further embodiment, seen for example, in FIG. 15, the outer wall curvate shape is cylindrical. In one embodiment, sufficient space is provided between 4-1, 6-1, and the springs to allow them to be compressed as much as 100%. But, in an alternative embodiment, guard slip-rings 9-1-2 and 9-1-3 (FIG. 26) or integrated lip guards 9-2-2 (FIG. 27) are included to prevent inversion of any Belleville spring in the stack, i.e., the frustum of the spring changing from pointing up to down or down to up. In one embodiment, a guard slip-ring is approximately ¼ to approximately ½ the height of a single Belleville spring. In another embodiment, the lip guards are approximately ¼ the height of a Belleville spring. With lip guards, the guard slip-rings are not necessary. The advantage of the guard slip-rings is that standard Belleville springs can be used in the spring stack. The advantage of the lip guards is that a separate part is not needed to eliminate spring inversion.

A person with skill in the art would recognize that an inversion of any spring can damage the spring and can change, at least minimally, the spring constant of the stack by converting a series configuration, in which the inverted spring is a part, into a parallel configuration. Unless the spring somehow re-inverts, this can have a deleterious effect on the intended operation of the device and should be avoided. Similarly, a parallel configuration would convert to a series configuration if only one spring inverted. Blocking rings or lip guards can, thus, restrict the amount of linear displacement along the axial axis since the springs are prevented from closing down completely.

There are several differences between Evan's instruction and that taught here. First, the guard rings lie in the active displacement space of the spring(s) and do not require a ring stub between stacked springs. This reduces the height for the spring stack, a critical aspect since the space height available is limited. The method taught here also provides that the Belleville springs themselves can be modified in their manufacture with lip guards that perform the same function as the guard slip-rings, without requiring a separate device. The use of deflection-limiting guards avoids the inversion singularity that occurs for Belleville springs if 100% deflections are allowed. If series coupled springs are not matched in pairs, there is some risk of spring inversion, in both Evan's scheme and the one instructed here. For instance, if one spring in series with another has a much smaller spring constant than the second spring in the pair, the softer spring might invert before the stiffer spring compress any significant amount. To avoid this possibility, approximately-matched series coupled Belleville springs can be desirable.

For 10 springs in series, the total displacement equals $10 \cdot h_e$ millimeters, where $h_e$, in millimeters, is the effective height of the Belleville spring, i.e., the actual amount the guards will allow each spring to compress. For example, if $h_e$ equals 0.224 mm, the spring stack of 10 springs in series will compress a maximum of 2.24 mm. Therefore, a Belleville spring with height 0.32 mm and guard lips of 0.08 mm will constrain a spring in a serial matched pair to compress no more than 70% of its height. The effective height then is 0.7 times 0.32 mm or 0.224 mm. At maximum compression, the central hydraulic cylinder and spring stack essentially becomes a fixed column between the FSU vertebrae that transmits any further compression forces to the FSU below.

The axial cylindrical joint, also called the central hydraulic cylinder, as noted in previous embodiments, comprises the combined elements of the inferior hydraulic cylinder 3-1, 4-1, and 5-1, and the superior hydraulic cylinder, consisting of elements 6-1, 7-1, and 10-1 (FIGS. 18-21). Thus, in one disclosed embodiment the slide block bearing 10-1-2 fixedly joins to the top center of plate 10-1 with hydraulic portals 10-1-3 drilled through the top surface to allow the transfer of fluid into and out of the upper chamber. The segmented-wall inner core 7-1 is centered and fixed to the underside of 10-1, such that the top surfaces of wall segments 7-1-2 alternate with slots 10-1-4. In an alternative embodiment, the guard rings 4-1-2 and 6-1-2 are cut or molded as one piece with the walls 4-1 and 6-1, this allows wall 4-1, whose outer surface 4-1-1 conforms to 6-1-1 and has hydraulic portals 4-1-3 drilled through the surface, to slide inside 6-1 from the top so the guard rings 4-1-2 and 6-1-2 do not interfere with the assembly. Further, the outer wall 6-1 with hydraulic portals 6-1-3 drilled into its side is fixed to the underside of 10-1, completing the superior hydraulic cylinder with inferior hydraulic cylinder wall 4-1 attached. In a further alternative embodiment, the guard ring 6-1-2 is a separate item that can be welded to the bottom of 6-1, then the superior and inferior hydraulic cylinders can be constructed separately. The axial cylindrical joint can then be assembled by telescoping the inferior hydraulic cylinder into the superior hydraulic cylinder and welding guard ring 6-1-2 to the bottom of 6-1. In a specific embodiment, one can insert any of a variety of resilient materials 15-1 and the spring stack 9-1 into the inferior cylindrical chamber, where 5-1 and 7-1 project through the inside diameters of the springs and resilient material and 4-1 and 6-1 surround and contain the springs and resilient material. A cutaway perspective view of the resulting axial cylindrical joint can be seen in FIGS. 9-11.

Figure 35:
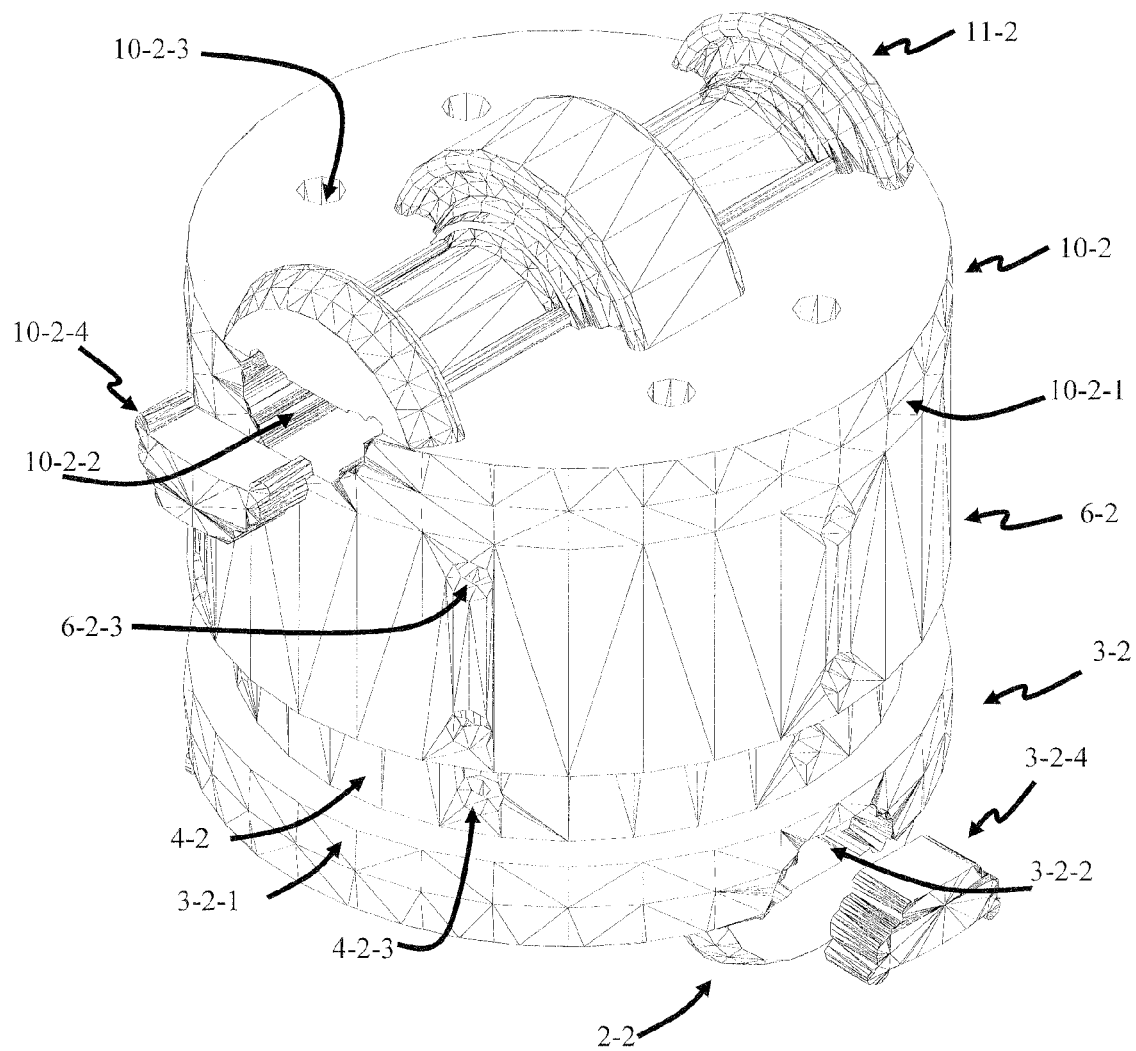
FIG. 35 depicts the alternative embodiment with the assembly of the central hydraulic cylinder with the lateral and sagittal rotational cylinders mounted. Constituent elements that can be used with this embodiment are the lateral rotation cylinder 11-2, the top plate 10-2, the superior hydraulic cylinder wall 6-2, the inferior hydraulic cylinder wall 4-2, the spring platform base 3-2, and the sagittal rotation cylinder 2-2. In a further embodiment, the ball bearings of the prismatic joint slideably lock 11-2 and 10-2 together. The bearing plugs 10-2-4 can be press-fit or otherwise fixed into place at each end, 11-2 and 10-2 do not separate during lateral translation of 11-2 with respect to the subassembly below it. Element 12-2, not shown in this diagram, is fixed to 11-2 with respect to any relative translation between 11-2 and 12-2, but 12-2 is free to rotate about cylinder 11-2. Element 1-2, not shown in this diagram, is fixed to 2-2 with respect to any relative translation between 1-2 and 2-2, but 1-2 is free to rotate about cylinder 2-2.

In one embodiment of the subject invention, the guard rings serve as joint stops for the axial prismatic motion of the axial cylindrical joint and prevent the device from separating when nominal forces attempt to hyperextend the FSU. In one embodiment, the guard rings circle the entire wall. In an alternative embodiment, the walls 4-1 and 6-1 can be segmented (three or four segments in a preferred embodiment) so that parts of the walls have no guard rings and other parts do. In this way, the walls can be thicker at those points where there are no guard rings. For example, 4-1 could be uniformly thicker around the circumference than 6-1, except for those segments of the two walls which have guard rings (FIG. 35). Alternatively, the thickness of both walls could be equal, but larger than the segments with no guard rings. In a further alternative, each wall segment can have a different thickness, as long as the total additional thickness equals the gap width produced by the guard ring projections. The point of these alternatives is to add mechanical strength to the core with thicker walls so that larger sheer forces can be tolerated.

In one embodiment, the inferior hydraulic cylinder is constructed such that the slide block bearing 3-1-2 fixedly joins to the bottom center of plate 3-1 with hydraulic portals 3-1-3 drilled through the top surface to allow the transfer of fluid into and out of the lower chamber. In a further embodiment, the segmented-wall inner core 5-1 is centered and fixed to the topside of 3-1 such that bottom surfaces of the wall segments 5-1-2 alternate with slots 3-1-4. Further, the bottom surface of wall 4-1 is centered and welded or otherwise fixed to the upper surface of 3-1, completing the construction of the inferior hydraulic cylinder.

It should be understood that in an embodiment where the guard rings are part of the wall structure, wall 4-1 is already telescoped into the superior hydraulic cylinder at this point in the construction. To finish the axial cylindrical joint, attach inner core 5-1 to the top of upper surface 3-1, place the spring stack 9-1, topped by resilient material 15-1, onto the spring platform base 3-1, and then affix wall 4-1 to the top of upper surface 3-1. The axial cylindrical joint can now slide along and rotate about the axial axis 18-1 with mechanically programmable joint stops for each of the two degrees of freedom. The spring stack and a resilient element provide resistance to compression and maintain variable intervertebral spacing throughout motion in the FSU workspace. In particular, the spring stack parameters are designed so that the invention maintains normal disc spacing when the FSU is in the normal position, but decreases the spacing during flexion and increases the spacing during extension in order to mimic natural disc behavior.

With the axial cylindrical joint realized, the superior end can be joined to the lateral rotation cylinder 11-1 and the inferior end can be joined to the sagittal rotational cylinder 2-1, as described earlier. The novelty and importance of incorporating spring elements into a moving, central hydraulic cylinder acting as a cylindrical joint can now be explained. In this embodiment of the subject invention, the spring elements move with the central hydraulic cylinder, a force acting on the FSU can sagittally and/or laterally rotate and/or slide the vertebral plates in the FSU moving frame and/or compress and rotate the central hydraulic cylinder along/about its axis. This action can continue until joint limit stops are encountered or the force or moment-of-force along a particular joint axis becomes zero. Any axial force component can tend to compress the spring elements along the preferred axis of the spring element and can be balanced out. Other components of the force can tend to activate the non-axial joint motions. At joint limit stops, the rigidity of the device is capable of opposing any non-axial forces or moment-of-force in the particular direction governed by that joint-at-limit. This feature of directing only normal forces onto the spring elements can be important for Belleville springs and other types of axial springs, as they do not function well under non-normal forces and is an important, novel element of this invention.

With the entire invention assembled the functions of cavity surfaces 1-1-7, 1-1-8, and (FIG. 28) of the inferior vertebral plate 1-1 and 12-1-7, 12-1-8, and 12-1-9 (FIG. 16) of the superior vertebral plate 12-1 can be inferred, especially after careful consideration of FIGS. 9, 10 and 11.

In one embodiment, the curvate, convex edge surface 3-1-1 conforms to concave surface 1-1-8. In a particular embodiment, surface 1-1-8 is cylindrical with center of curvature on sagittal axis 16-1 and edge surface 3-1-1 is spherical with center on sagittal axis 16-1. As the plate 3-1 rotates about 16-1, the surfaces 3-1-1 and 1-1-8 do not interfere. When 3-1 sagittally translates to its extreme values, the surface concavity at each end of the cylinder socket of 1-1 is not a continuation of cylindrical surface 1-1-8, but is actually spherical with center coinciding with the moved center of surface 3-1-1. The displaced center of 3-1-1 is still on 16-1, since the motion is along the direction of 16-1. The surfaces 3-1-1 and those at the end of the cylinder socket conform to one another and do not interfere during sagittal rotation. This approach allows the walls of 1-1 to be thicker and more robust at the end of the socket concavity as opposed to a rectangular shaped cut for the socket.

Surface 1-1-9 can conform to the lower surface of plate 3-1 and serve as a joint stop for sagittal rotation. The acute angle plane 1-1-9 makes with the axial plane when the device is in normal position (FIG. 10) defines the maximum sagittal angle of rotation in one direction that the elements above the inferior vertebral device can rotate, in flexion (FIG. 9) or extension (FIG. 11). The planar cut 1-1-7 can prevent the walls 6-1 (and necessarily walls 4-1) of the superior hydraulic cylinder from interfering with the inferior vertebral plate 1-1, even at maximum flexion or extension. In one embodiment, at the socket ends of 1-1, the surface 1-1-7 becomes a rotated planar cut about the axial axis to prevent interference between 1-1 and 6-1 when the central hydraulic cylinder, at either extreme of sagittal translation, rotates about 16-1, even at maximum flexion and maximum extension.

In a further embodiment, the curvate, convex edge surface 10-1-1 conforms to concave surface 12-1-8. In a particular embodiment, surface 12-1-8 is cylindrical with center of curvature on lateral axis 17-1 and edge surface 10-1-1 is spherical with center on lateral axis 17-1. In this embodiment as the plate 10-1 rotates about 17-1, the surfaces 10-1-1 and 12-1-8 do not interfere. When 10-1 laterally translates to its extreme values, the surface concavity at each end of the cylinder socket of 12-1 is not a continuation of cylindrical surface 12-1-8, but can actually be spherical with center coinciding with the moved center of surface 10-1-1. The displaced center of 10-1-1 can still be on 17-1, since the motion is along the direction of 17-1. The surfaces 10-1-1 and those at the end of the cylinder socket are also able to conform to one another and do not interfere during lateral rotation. This approach allows the walls of 12-1 to be thicker and more robust at the end of the socket concavity as opposed to a rectangular shaped cut for the socket.

Further, surface 12-1-9 can conform to the upper surface of plate 10-1 and serves as a joint stop for lateral rotation. The acute angle that plane 12-1-9 makes with the frontal plane, with the device in normal position, defines the maximum lateral angle, in one direction, that the superior vertebral plate can rotate about 17-1. The planar cut 12-1-7 can also prevent the walls 6-1 (and necessarily walls 4-1) of the superior hydraulic cylinder from interfering with the inferior vertebral plate 12-1, even at maximum flexion or extension. In a further embodiment, at the socket ends of 12-1, the surface 12-1-7 becomes a rotated planar cut about the axial axis to prevent interference between 12-1 and 6-1 when the central hydraulic cylinder, at either extreme of lateral translation, rotates about 17-1, even at maximum left or right lateral bending.

A second embodiment (shown, for example, in FIGS. 29 and 30) is, in general, the embodiment(s) described above, but with all lower order pair joints replaced by higher order pairs. In a specific embodiment, ball or rod bearings are utilized running on raceway rods. The bearings and rods in the subject invention can comprise any of a variety of materials, including, for example, titanium-carbide-covered hardened stainless steel, ultra-high-molecular-weight polyethylene or similar thermoplastic material; metal alloys, biocompatible materials and other suitable materials or combinations thereof. In a specific embodiment, the raceway rods comprise hardened stainless steel. The general elements n-2 of the second embodiment corresponds to the general elements n-1 of the first embodiment in overall shape and function, although their detail structures may differ substantially. In one embodiment, the subject invention is basically cylindrical in shape with cylindrical surfaces 12-2-12 and 1-2-12. However, a person with skill in the art and benefit of the subject disclosure would be able to devise alternative embodiments having different enclosing surfaces for the interior mechanism. Such alternative are within the scope of the subject invention.

Figure 29:
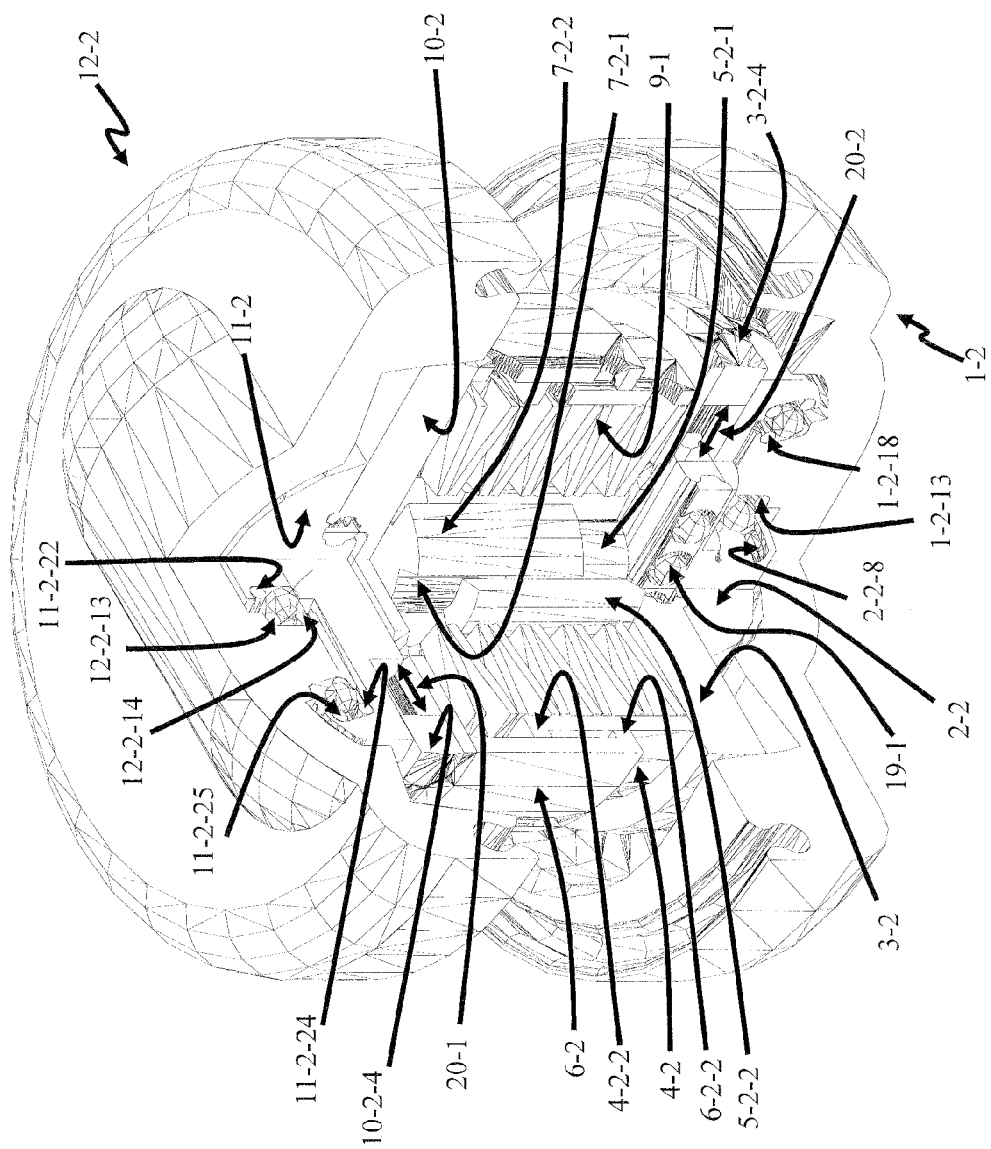
FIG. 29 illustrates a quadrant cutaway perspective of a second embodiment of the subject invention, without a boot, that uses ball bearings in place of lower order pairs for the joints. The part numbering scheme can show the functional relationships between the two embodiments. Often, for example, n-2 or n-2-m corresponds functionally, to elements n-1 or n-1-m. There are exceptions, but this observation will make understanding the second embodiment easier, if the first embodiment is understood.
Figure 36:
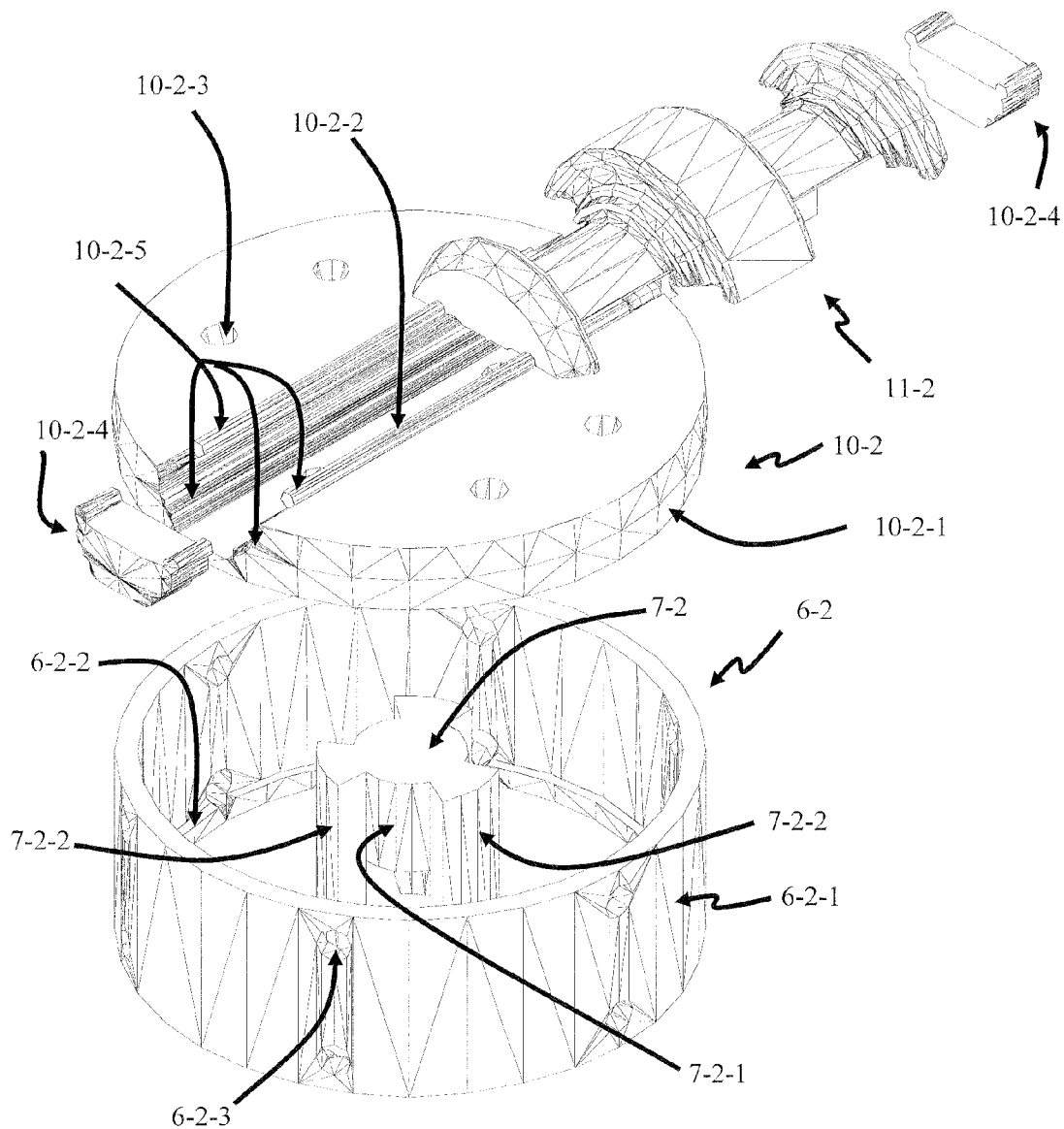
FIG. 36 shows a view that exposes the interior of the superior hydraulic cylinder and the lateral slider bearing raceway in the top plate 10-2, of the alternative embodiment. In this particular embodiment, ball bearings (not shown) rest on the rods 10-2-5 and lock 10-2 and 11-2 together, after the later is slid into position and blocked at either end with prismatic bearing stops 10-2-4. In a further particular embodiment, the superior hydraulic cylinder wall 6-2 and superior segmented-wall cylinder 7-2 weld or fix to the top plate 10-2. In another embodiment, 10-2, 7-2, and 6-2 can be produced as a single unit or, in another method, 7-2, as a separate unit, and can be centered and welded or otherwise fixed to an integrated, or molded, 10-2 combined with 6-2.
Figure 37:
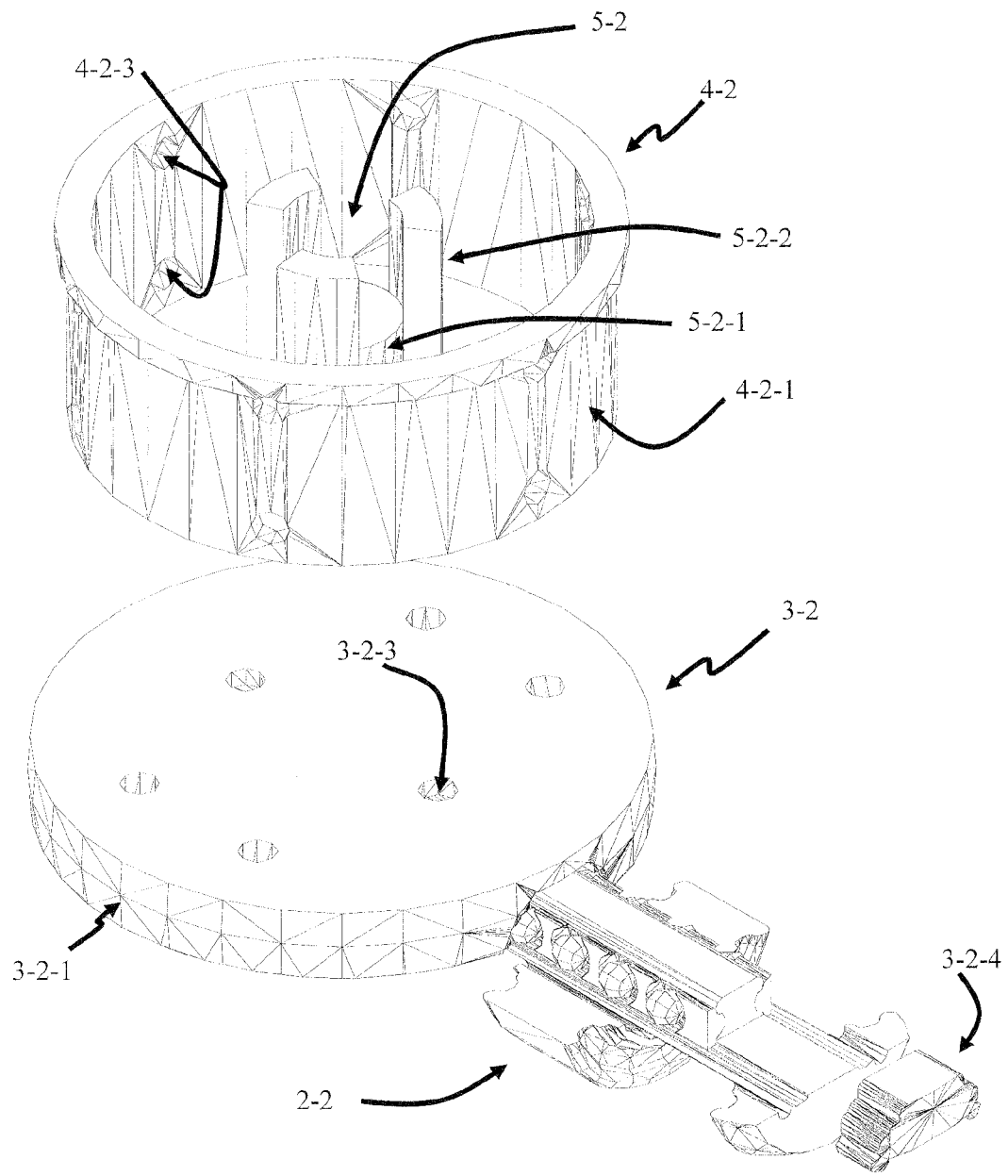
FIG. 37 provides an exploded, perspective view of a sub-assembly of the subject alternative embodiment having the inferior hydraulic cylinder wall 4-2, the inferior segmented-wall cylinder 5-2, the spring platform 3-2, and the sagittal rotation cylinder 2-2 with attached sagittal prismatic ball bearings inserted with ball bearing separators and stops. In this embodiment, element 2-2 slides into the slot provided in 3-2 and locks into place by press fit of prismatic bearing blocks 3-2-4 at each end of 3-2. Elements 4-2 and 5-2 can be welded or fixed to 3-2 or cut or molded as an integrated part with 3-2.
Figure 47:
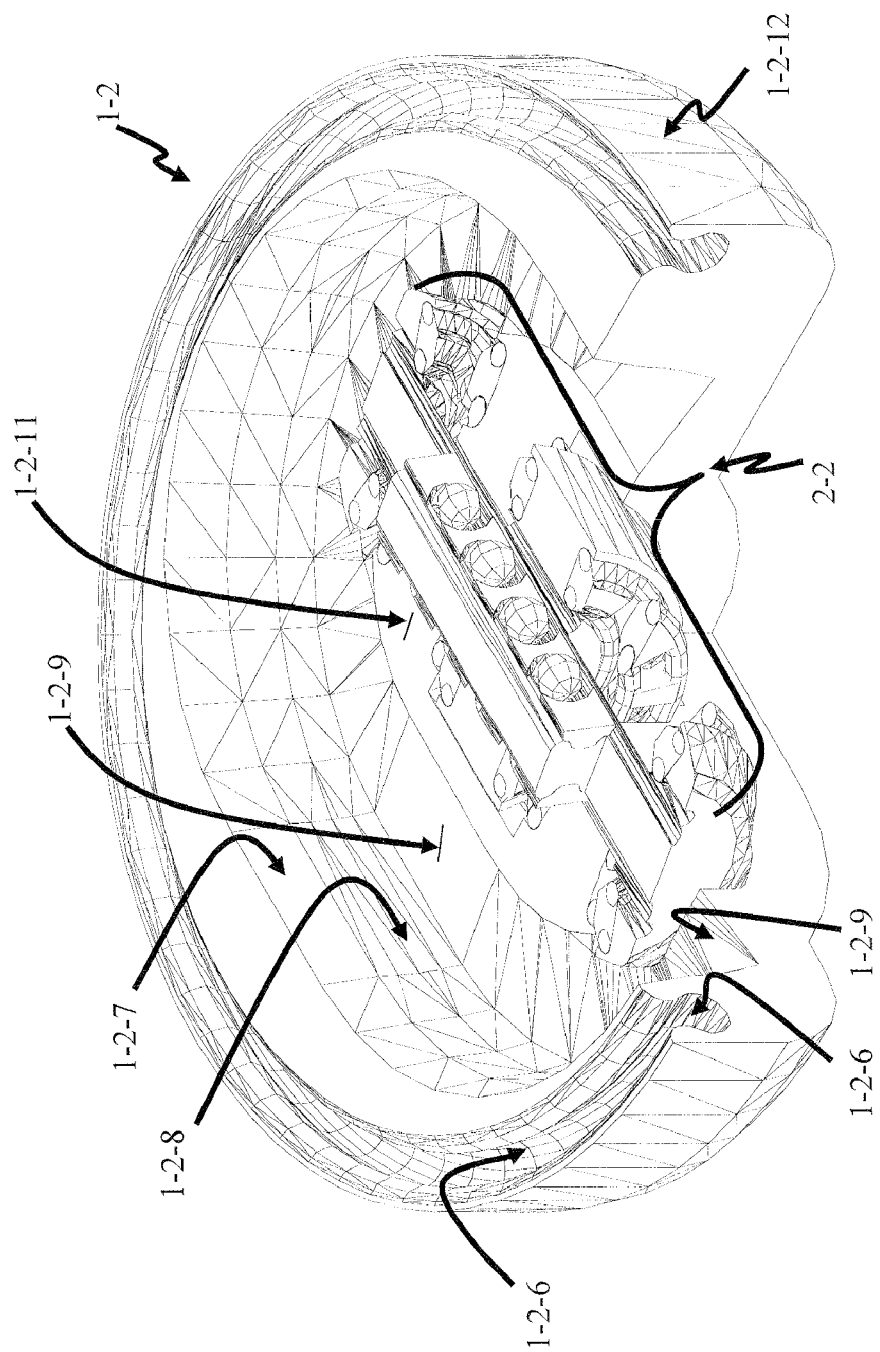
FIG. 47 shows a quadrant cutaway perspective view of 1-2 and the whole element 2-2 depicting surface features of an embodiment of a sagittal cylindrical socket in 1-2 along with the embedded element 2-2.

In an alternative embodiment, lock keys are not needed to retain the sagittal 2-2 and lateral cylinders 11-2 into the inferior 1-2 and superior vertebral plates 12-2. Rather, to insure unbroken kinematic linkage between the two vertebral plates, bearing elements can rotationally or slidingly lock the various joints together, namely, the lateral cylindrical joint (lateral revolute and slider joints) and the sagittal cylindrical joint (sagittal revolute and slider joints). In a further embodiment, the lateral revolute joint consists of principal elements 11-2 and 12-2 (FIG. 29). The sagittal revolute joint consists of principal elements of 1-2 and 2-2 (FIG. 47). The lateral slider joint consists of principal elements 10-2 and 11-2 (FIG. 36). The sagittal slider joint elements consist of principal elements 3-2 and 2-2 (FIG. 37).

Figure 30:
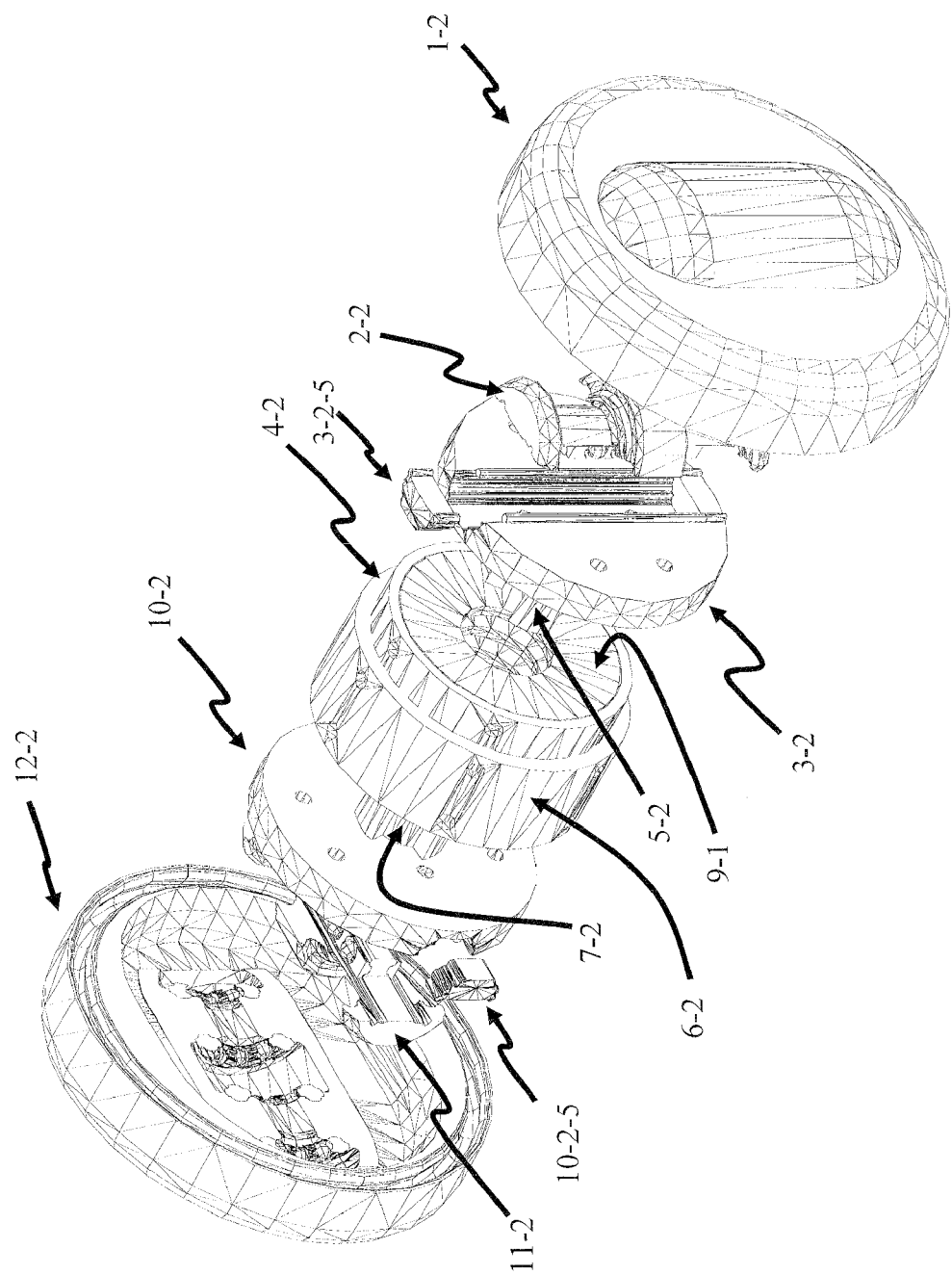
FIG. 30 is a perspective exploded view of the assembly of the alternative embodiment, again, without the boot. The various bearing raceways can be seen here without the ball bearings. Seen are the principle elements of this embodiment: the inferior vertebral plate 1-2, the sagittal rotation cylinder 2-2, the spring base plate 3-2, the inferior segmented-wall cylinder 5-2, the spring stack 9-1, the inferior hydraulic cylinder wall 4-2, the superior hydraulic cylinder wall 6-2, the superior segmented-wall cylinder 7-2, the top plate 10-2 of the superior hydraulic cylinder wall, the lateral rotation cylinder 11-2, and the superior vertebral plate 12-2.

FIG. 30 is an exploded perspective view of a second embodiment that illustrates examples of the principal elements: 1) the inferior vertebral plate with bearings 1-2, 2) the sagittal rotation cylinder with bearings 2-2, 3) the spring base with sagittal slider raceway 3-2 and bearing stop 3-2-5, 4) the spring element 9-1 (options and variations in the spring elements are unchanged from the first embodiment), 5) the inferior hydraulic cylinder outer walls 4-2 and inner core 5-2, 6) the superior hydraulic cylinder outer walls 6-2 and inner core 7-2, 7) the top plate 10-2 of the hydraulic cylinder with lateral prismatic raceway and bearing stops 10-2-5, 8) the lateral rotation cylinder with bearings 11-2, and 9) the superior vertebral plate with bearings 12-2.

FIG. 29, which is a quadrant cutaway perspective of an embodiment of the entire unit without the boot, shows a few more details. The distances 20-1 and 20-2 show examples of the lateral and sagittal slider joint displacements. In one embodiment, distances 20-1 and 20-2 show approximately one-half the lateral and sagittal slider joint displacements The segmented walls 5-2-2 and 7-2-2 and cores 5-2-1 and 7-2-1 work as described above, except the walls do not penetrate into plates 10-2 and 3-2. The guard rings 4-2-2 and 6-2-2 keep the telescoping walls 4-2 and 6-2 from separating, and can, thus, serve as a joint stop for the axial slider joint by limiting maximum extension. During sagittal rotations, plate 3-2 and elements attached above can rotate with cylinder 2-2 within the socket of 1-2.

Ball bearings 19-1 are shown in all the joints of FIG. 29, but, in an alternative embodiment, they can be replaced by rod bearings, cylindrical bearings, or any of a variety of other suitable options known to those skilled in the art. FIG. 29 does not show all the lateral revolute joint bearing rods that can be utilized with embodiments of the subject invention. But, the easily visible ones are 11-2-22, 11-2-24, 11-2-25, 12-2-13, and 12-2-14. In one embodiment, each bearing raceway, in general, will have four bearing rods to support the joint loads through ball bearings or other such elements. In a further embodiment, the bearing rods comprise hardened stainless steel. Embodiments employing bearing elements for the sagittal revolute joint and sagittal slider joint will be discussed in detail below. In one embodiment, the lateral revolute and slider joints function the same way as the sagittal revolute and slider joints and have similar or identical structure as described previously herein.

Figure 39:
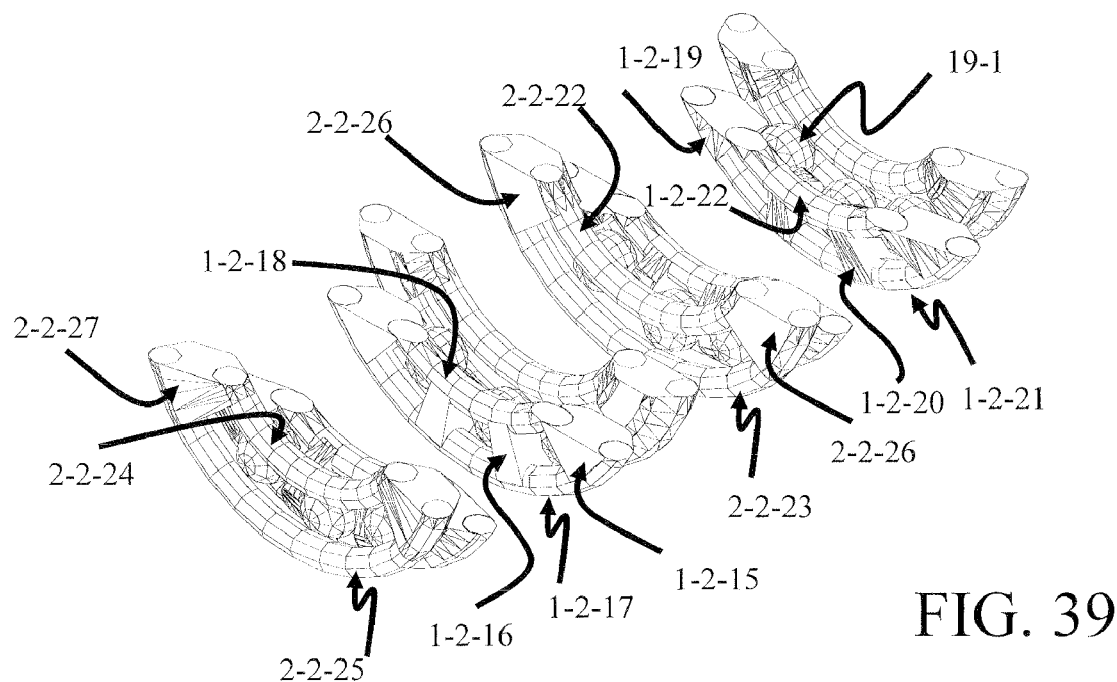
FIG. 39 shows in the alternative embodiment, the curvate bearing rods 2-22, 2-23, 2-24, and 2-25, bearing stops 2-26, and 2-27, and their mirror images in the sagittal plane passing through the central axis of the subject invention, that fit into the raceways of 2-2. The curvate bearing rods 2-22, 2-23, 2-24, and 2-25, bearing separators 1-2-16, bearing stops 1-2-20 and 1-2-19 and their mirror images in the sagittal plane passing through the central axis of the device, fit into the raceways of 1-2.
Figure 40:
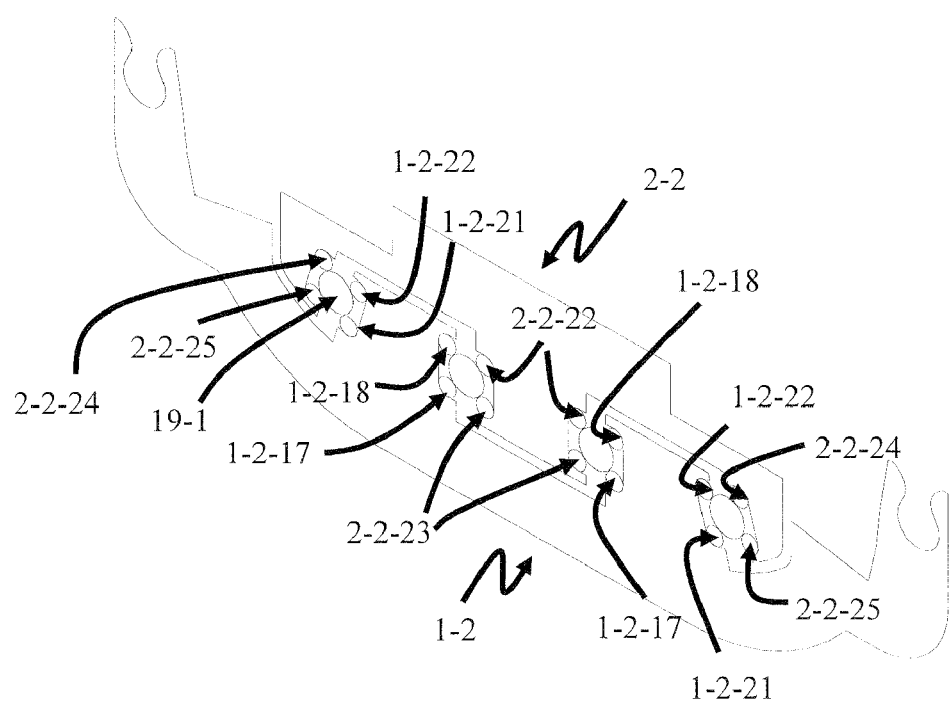
FIG. 40 is a view of the frontal plane section of the inferior vertebral plate 1-2 and the sagittal rotation cylinder 2-2 through the central axis of an alternative embodiment of the invention. The section shows how steel ball bearings suspend on four rails (for example, pair 1-2-17, 1-2-18 and pair 2-22, 2-23). This arrangement can allow limited rotation of 2-2 with respect to 1-2 about the sagittal axis 16-1, while forcing the two elements 1-2 and 2-2 to move together without relative motion for all other directions.
Figure 50:
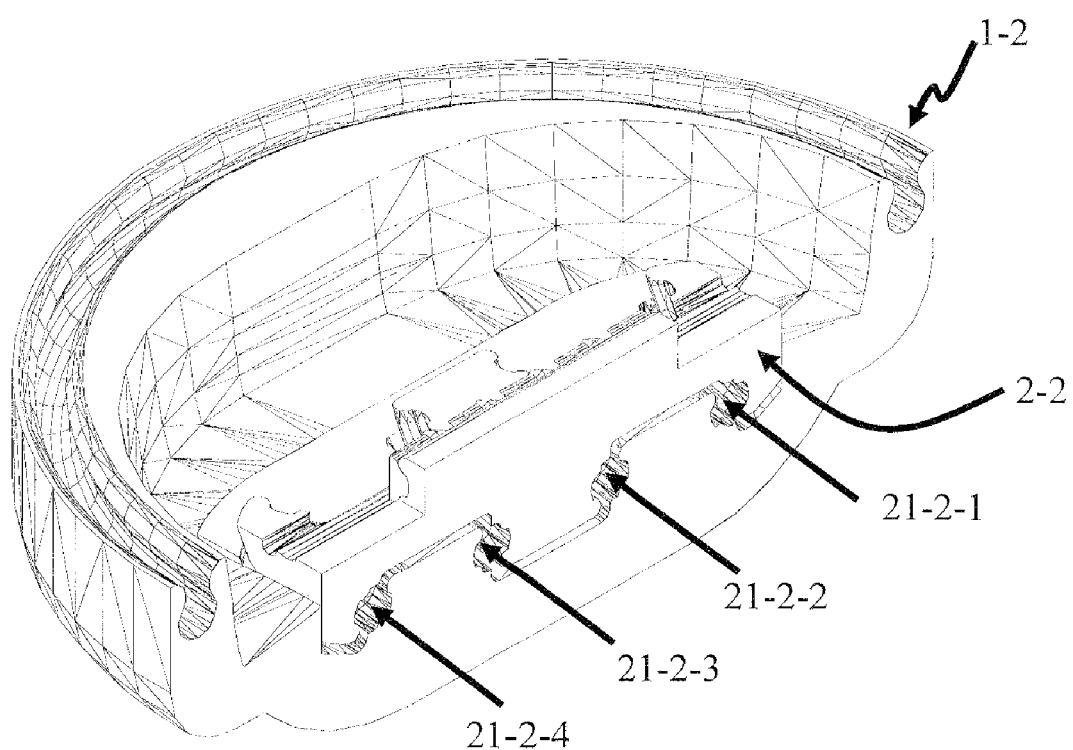
FIG. 50 shows a perspective, frontal plane cutaway view through the middle of 1-2 and 2-2, but with the bearing elements removed so the bearing pathways can be seen clearly.

In the second embodiment, the inferior vertebral plate 1-2 can form four bearing raceways 21-2-1, 21-2-2, 21-2-3, and 21-2-4 (FIG. 50) with the sagittal revolute cylinder with bearings, 2-2. Each of these raceways can further have four rods each, comprising, for example, hardened stainless steel: rods 1-2-21, 1-2-22, 2-2-24, and 2-2-25 for raceways 21-2-1 and 21-2-4; and rods 1-2-17, 1-2-18, 2-2-22, and 2-2-23 for raceways 21-2-2 and 21-2-3 (FIG. 40). A perspective view of all the bearing elements for these four raceways is illustrated in FIG. 39.

Figure 42:
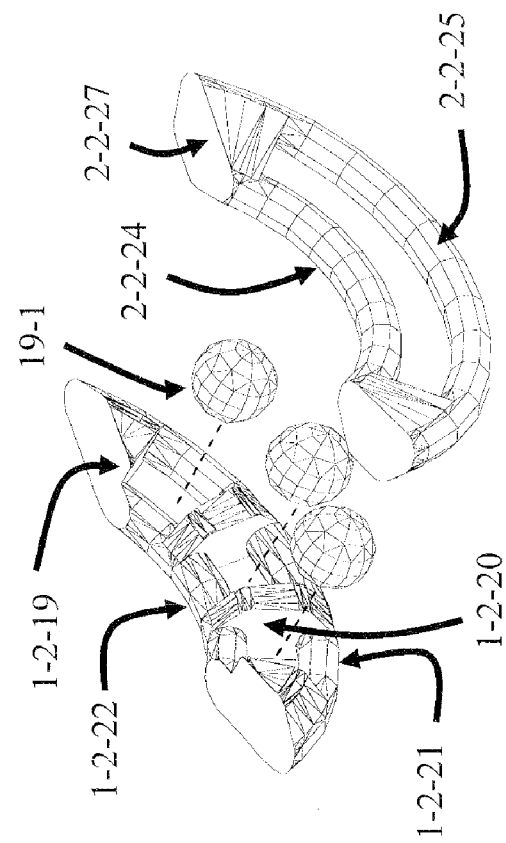
FIG. 42 provides a partially exploded view of an alternative embodiment showing the end bearings of 2-2.
Figure 41:
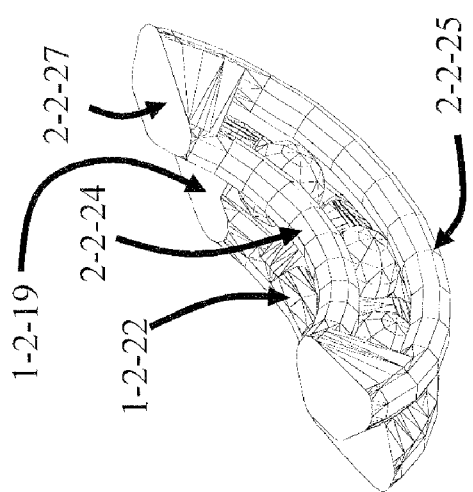
FIG. 41 details sagittal rotation bearing elements at one end of 2-2 an embodiment of the subject invention. The bearing elements at the other end are a mirror images of this one about a frontal plane through the center axis of the device. These end bearing elements can have center of curvature on the axis 16-1, but have different dimensions than the inside bearing elements (FIG. 43 and FIG. 44) as they fit at an angle (see FIG. 40)
Figure 44:
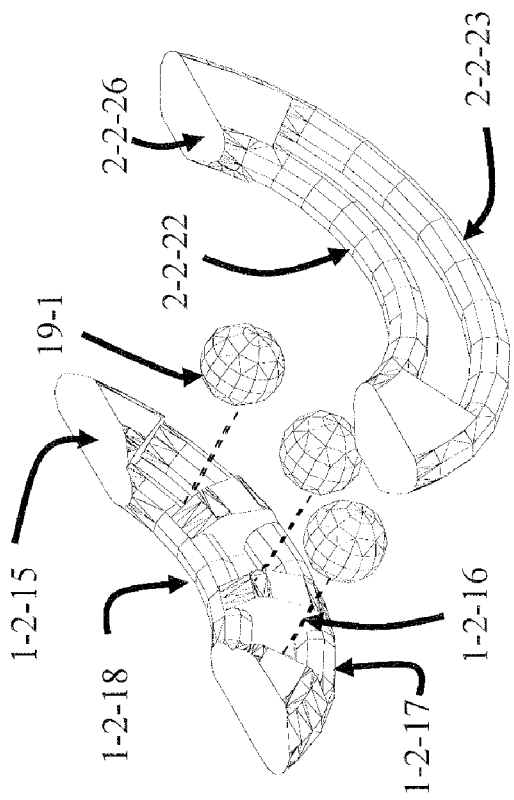
Figure 43:
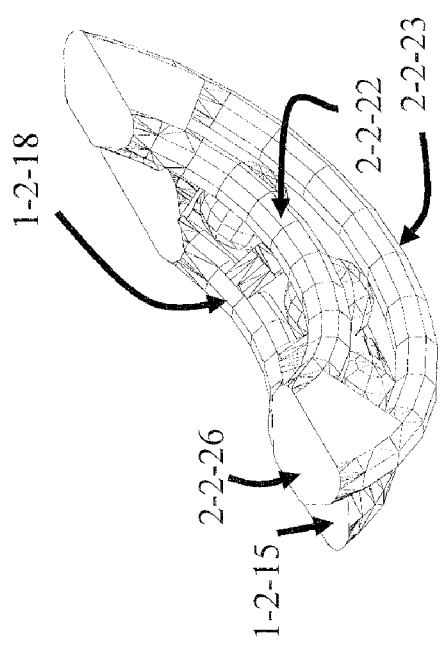
FIG. 43 shows details of sagittal rotation bearing elements for the inside raceways of 2-2 of an alternative embodiment of the subject invention. A mirror image of these bearing elements about a frontal plane through the center axis of the device, fit into the other inside raceway FIG. 44 provides a partially exploded view of the inner bearing elements of 2-2.
Figure 45:
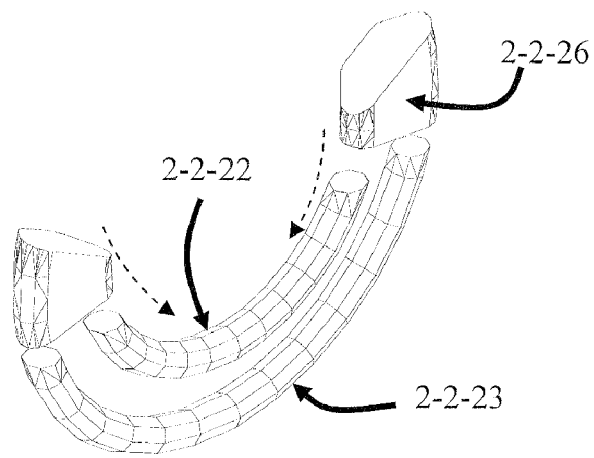
FIG. 45 shows an embodiment of a rod bearing that separates the bearing stops 2-26 from the bearing rods 2-2-22 and 2-2-23. The bearing stops fixedly join the rods into a unit, at least at one end. The other end can be movable and the rods insert into them with a press fit.

An embodiment of a set of raceway rods for 21-2-1 and 21-2-4 is shown in FIG. 41. The exploded perspective view FIG. 42 shows the curvate bearing separators 1-2-20 and bearing stops 1-2-19 that can be utilized with the inferior vertebral plate side of the raceway while the sagittal rotation cylinder portion has curvate bearing stops 2-2-27. The bearing separators and stops of rods 1-2-21 and 1-2-22 are designed so as to be able to conform- to the cylindrical curvature of the rods and raceway. In one embodiment, with the ball bearings 19-1 and bearing separators 1-2-20 in place, there is enough tolerance to slide the assembly into the left side of the raceway 2-22-4 and the right side of raceway 2-22-1, even with the sagittal cylinder in place within the inferior vertebral plate socket. The bearing separators and stops can block only half of the raceway, whereby that, plus a small tolerance in the socket size for 2-2, allows the rods 2-2-22 and 2-2-23 to slip into the right-side of 2-22-4 and the left side of 2-22-1. Bearing stops can be welded or otherwise attached to the ends of the bearing rods. The lengths of the configuration 2-2-22, 2-2-23, and stops 2-2-26, or equivalently, assuming the same length, of 2-2-24, 2-2-25, and 2-2-27, can determine the degrees of rotation of the sagittal cylinder within the inferior vertebral plate socket as the stops 2-2-26 and 2-2-27 cannot get past the first ball bearing. When assembled with stops the bearings can lock the sagittal cylinder and the inferior vertebra plate together and can simultaneously lock the bearings into place. A similar technique can be applied to assembling bearings 19-1, bearing separators 1-2-16, bearing stops 1-2-15 and 1-2-26, and curvate bearing rods 1-2-17, 1-2-18, 2-2-22, and 2-2-23 into raceways 2-22-2 and 2-22-3 (refer to FIGS. 43, 44, and 45, the latter highlighting the assembly of joint stops onto raceway rods).

Figure 46:
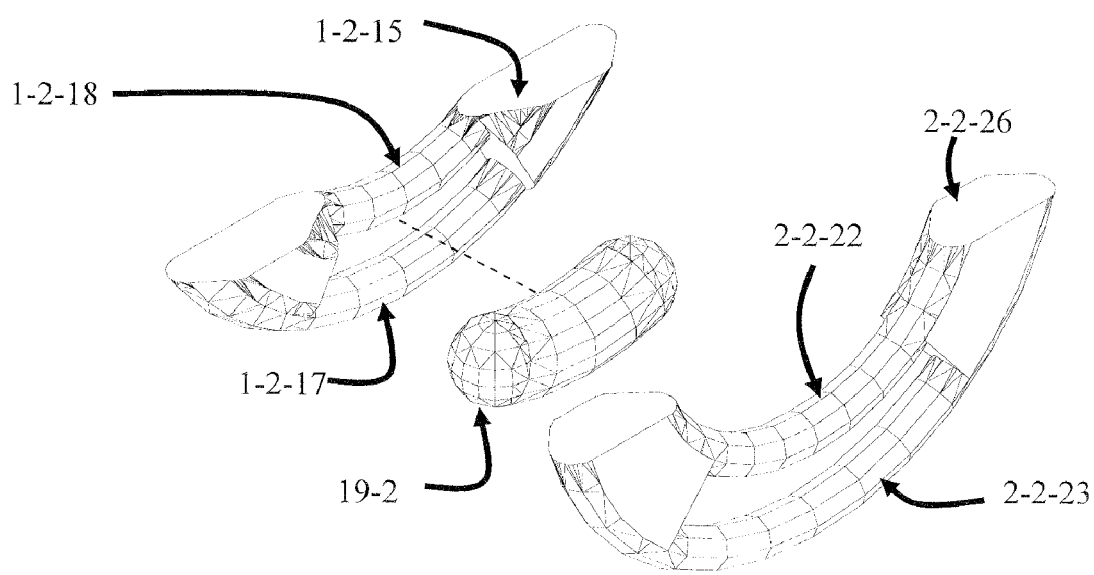
FIG. 46 shows a curvate rod bearing 19-2 embodiment that allows the curvate bearing rods (1-2-17, 1-2-18, 2-2-22, 2-2-23) to slide by as 1-2 rotates relative to 2-2.

In an alternative embodiment, bearings other than ball bearings can be used. For example, a rod-bearing 19-2 alternative to ball bearings is illustrated for one of the bearing assemblies in FIG. 46.

Figure 48:
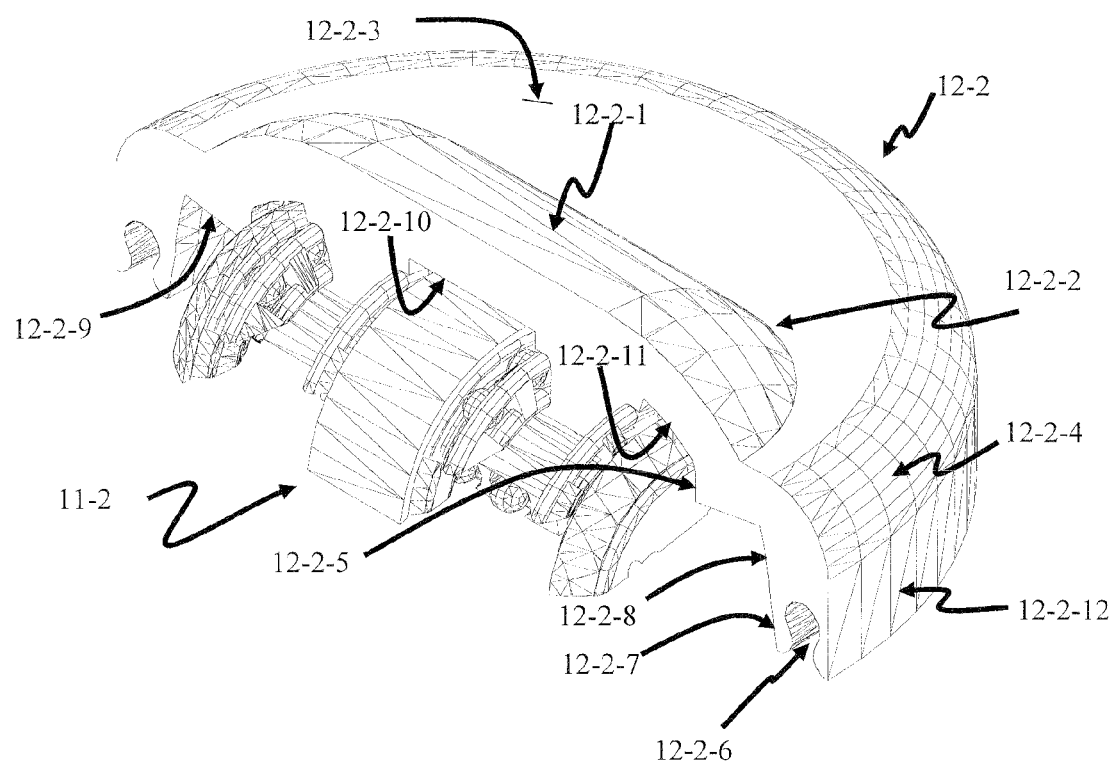
FIG. 48 displays an embodiment of the entire lateral rotation cylinder 11-2 embedded into a perspective half of the superior vertebral plate 12-2.

A set of bearing elements and four raceways identical to those of the sagittal rotation cylinder and inferior vertebral plate interface can be employed for the lateral rotation cylinder 11-2 and superior vertebral plate 12-2 interface that allows bearing placement in like manner (see FIG. 48). The cylindrical surface 12-2-10 and spherical surfaces 12-2-11 can interface to conforming surfaces on rotation cylinder 11-2. The surfaces 12-2-7, 12-2-8, 12-2-9, and boot ring groove 12-2-6 can have the same surface requirements and functions as the corresponding ones described previously; likewise for surfaces 12-2-1, 12-2-2, 12-2-3, 12-2-4. In one embodiment, planar surface 12-2-5 is cut back away from the end of the cylinder to allow enough lateral tolerance for assembling the locking bearing elements. In a further embodiment, the lateral revolute and slider joints are identical in structure to the sagittal revolute and slider joints, described above.

Figure 49:
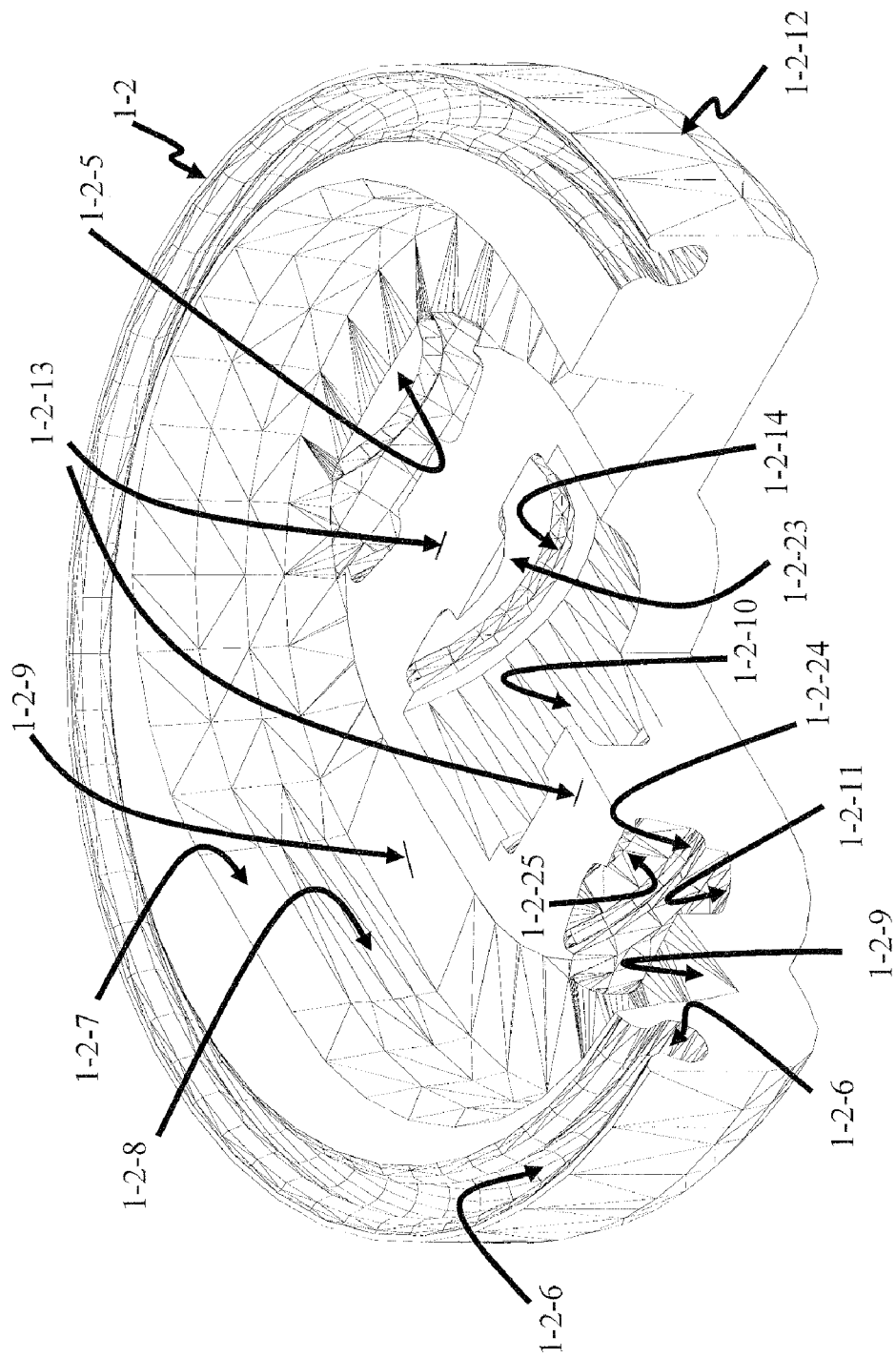
FIG. 49 details the socket surfaces in 1-2 which can be hidden by the cylinder 2-2.

One embodiment of the placement of the sagittal rotation cylinder with bearings 2-2 into the inferior vertebral plate with bearings 1-2 is shown, for example, in the perspective view of FIG. 47, wherein a quarter section of the inferior vertebral plate with bearings 1-2 is removed. Socket features visible here include 1-2-7, 1-2-8, and 1-2-9 which can have the same function and curvatures as those surface described above, in the previous embodiment. Other socket surface details appear in FIG. 49. Cylindrical concave surface 1-2-10 and spherical concave surfaces 1-2-11 can conform to corresponding surfaces on the sagittal rotation cylinder with bearings 2-2. In a further embodiment, planar surfaces 1-2-23, and 1-2-25 are bearing walls and curvate surfaces 1-2-14 and 1-2-24 hold bearing raceway rods. In a further embodiment, the planar surfaces 1-2-5 conform to the ends of the cylinder, but do not touch same in order to allow enough sagittal axis displacement for bearing insertion. Planar surfaces 1-2-13 do not come into contact with the cylinder 2-2, which can be completely supported by the bearing elements of the revolute joint between 1-2 and 2-2.

Figure 31:
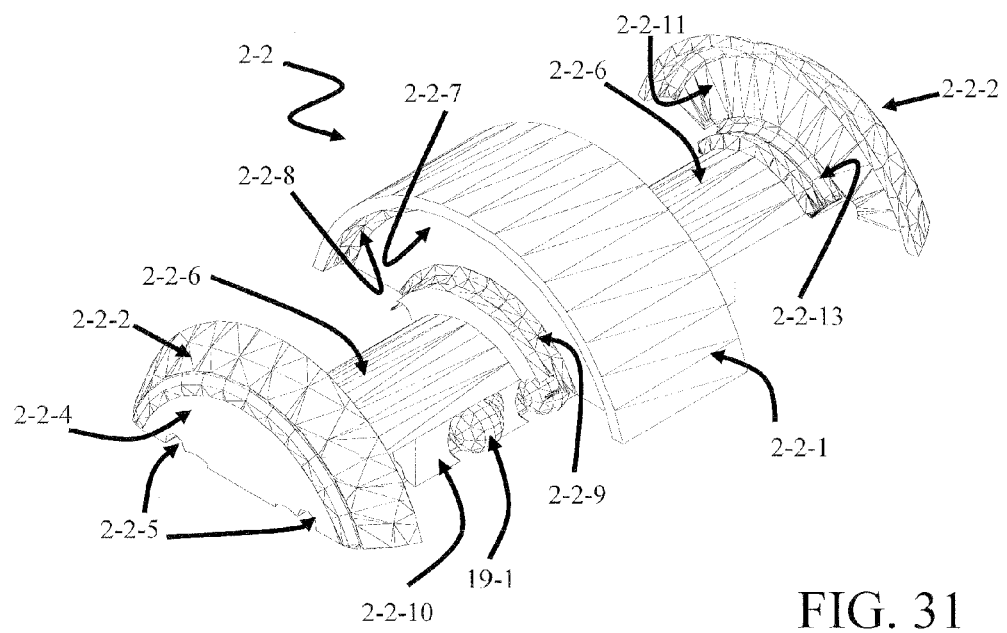
FIG. 31 shows the embodiment wherein the sagittal rotation cylinder 2-2 incorporates ball bearings and ball bearing raceways that mesh with the other half of the raceways embedded into the inferior vertebral plate 1-2. The rotational ball bearings are not shown so as to illustrate the raceways better. The sagittal slider ball bearings 19-1, however, are shown. In a further embodiment, the lateral rotation cylinder 11-2 is identical to the sagittal rotation cylinder 2-2 in structure.
Figure 32:
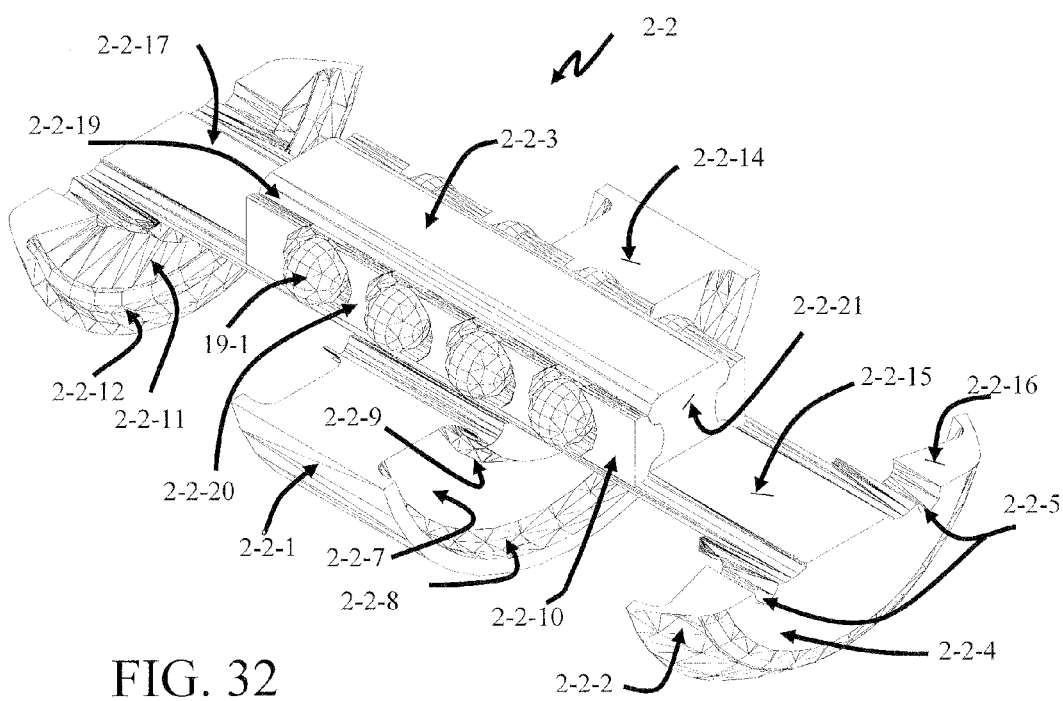
FIG. 32 shows the top features of the sagittal rotation cylinder 2-2. In this embodiment, on the sagittal bearing structure 2-2-3, the projections 2-2-18 and 2-2-19 can be replaced with bearing rods. The grooves 2-2-5 provide clearance for bearing rods in the sagittal slider raceway. Refer to bearing rods 10-2-5 of the lateral cylindrical joint configuration (FIG. 36) for one embodiment of how this is done for the sagittal cylindrical joint. The sagittal slider bearing stops 2-2-10 and bearing separators 2-2-20 can hold the bearings 19-1 in place and can be press fit or otherwise fixed into place. The sagittal slider bearing structure translates parallel to the rotation axis 16-1 within a concavity on the inferior surface of the spring platform base 3-2 FIG. 33 details features of the sagittal linear bearing stops 2-2-10 and bearing separators 2-2-20 of the alternative embodiment.
Figure 33:
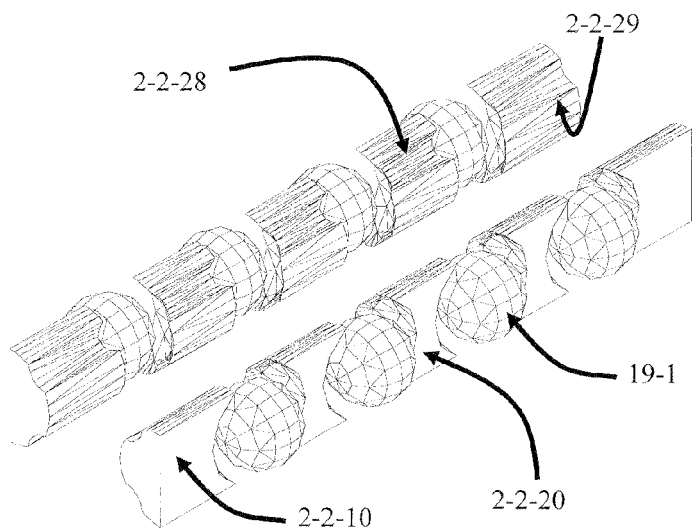
Figure 34:
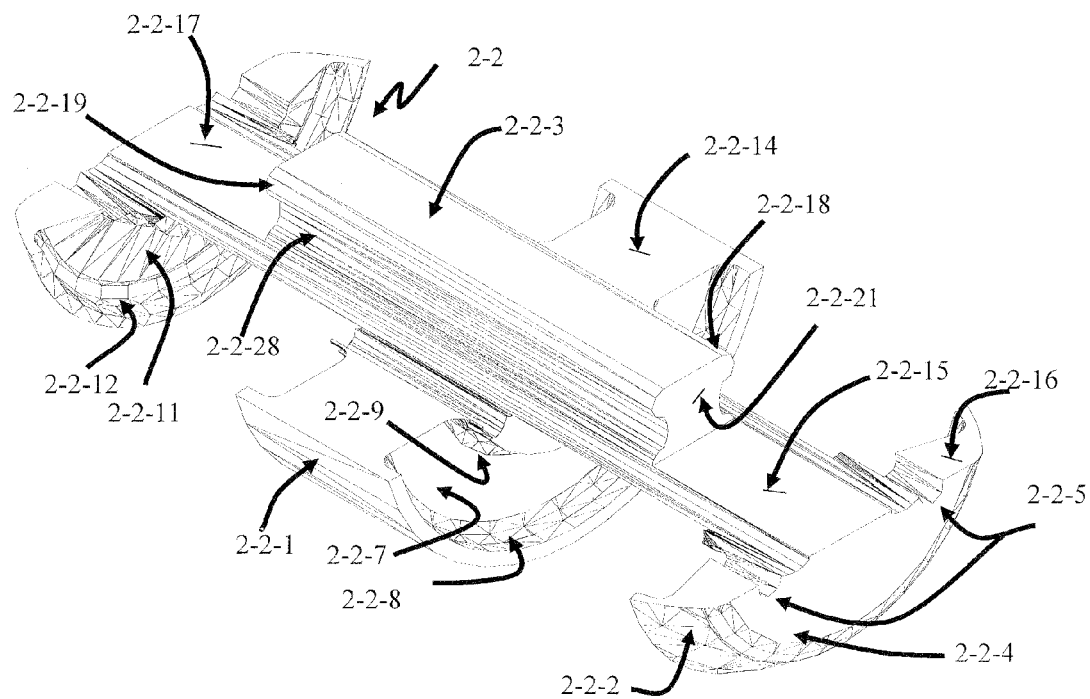
FIG. 34 illustrates the alternative embodiment wherein the sagittal rotation cylinder with the sagittal slider bearings and bearing stops are removed to expose the bearing raceway concavity 2-2-28 cut from the sagittal linear bearing structure 2-2-3. The rotational bearings have also been removed in this view to show the rotational bearing chambers.

FIG. 31 illustrates an embodiment of the sagittal rotation cylinder with bearings 2-2 in perspective from underneath, where the rotational bearing elements have been removed from the raceways. FIG. 32 illustrates an embodiment of cylinder 2-2 in perspective from above with the sagittal slider bearings added (FIG. 33). FIG. 34 illustrates 2-2 in perspective from above without the sagittal slider bearing elements.

Structure, construction and function of the central hydraulic cylinder with bearings of the second embodiment closely resemble the central hydraulic cylinder of the first embodiment (FIGS. 35, 36, and 37). For example, both include an axial revolute joint and an axial slider joint. Slider joint construction differs considerably between the first and second embodiments and is discussed throughout the subject application. The embodiments disclosed herein disclose that component elements of the central hydraulic cylinder include centering and fixing 6-2 and 7-2 to the under side of 10-2; centering and fixing 4-2 and 5-2 to the top side of 3-2; and joining and slidably locking the two subassemblies together with guard rings 6-2-2 and 4-2-2. Hydraulic portals 3-2-3, 4-2-3, 6-2-3, and 10-2-3 can be drilled through the associated elements of the central hydraulic cylinder. These portals allow the passage of lubricating fluid and provide damping action to sudden compressive or extensive forces acting on the cylinder.

Surfaces 6-2-1 and 4-2-1 can also be shaped into conforming walls with polygonal cross sections or cross sections with combinations of curvate segments. For all possible motions of the central hydraulic "cylinder", convex surfaces 1-2-7 and 12-2-7, cut from the socket of the vertebral plates, can be constructed to conform to the rotated and translated surfaces of the central hydraulic "cylinder" without interference with 1-2 or 12-2.

In further embodiments, the convex edge curvate surface 3-2-1 (10-2-1) and the concave wall surfaces 1-2-8 and 1-2-9

(12-2-8 and 12-2-9) of the inferior (superior) vertebral socket which plate 3-2 (10-2) encounters during all its possible motions with respect to 1-2 (10-2) are all conformal to 3-2-1 (10-2-1) and do not interfere with each other, just like the corresponding surface in the first embodiment do not interfere. Planar surface 1-2-9 (12-2-9) can act as a joint limit stop for the sagittal (lateral) revolute joints. Plate 3-2 (10-2) when rotated about 16-1 (17-1) against surface 1-2-9 (12-2-9), will inhibit any further rotation of the sagittal (lateral) revolute joint.

Figure 38:
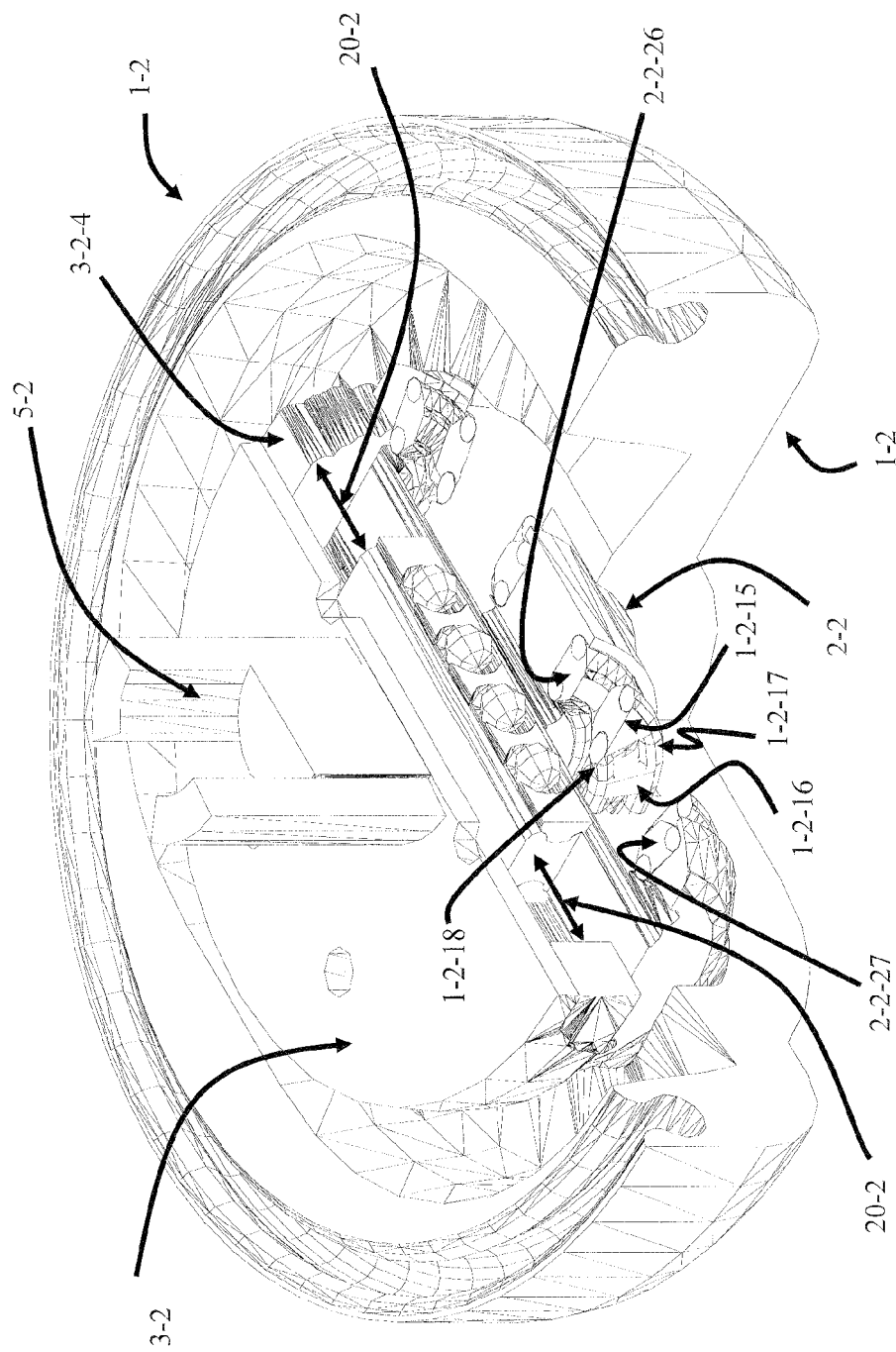
FIG. 38 provides a quadrant cutaway perspective of an embodiment of the elements 1-2, 2-2 and a split of an embodiment of elements 3-2, and 5-2. In this embodiment, the rods and the ball bearings that slide along them, retain 2-2 within 1-2, once the bearing stops 2-26 and 2-27 that fit in the curvate bearing raceways of 2-2 and the bearing stops 1-2-15 and 1-2-19 that fit in the curvate bearing raceways of 1-2 (see FIG. 39) have been inserted.

A partial cutaway perspective of an embodiment of the sagittal revolute and slider joints is shown in FIG. 38. The slider displacements 20-2 can be seen in this view. Description of these joint embodiments and their constituent elements follow.

Many of the features of the sagittal rotation cylinder 2-1 (and by equivalence the lateral rotation cylinder 11-1) of the first embodiment are reflected in the second embodiment 2-2 (11-2). For example, in the second or alternative embodiment, surface 2-2-1 is cylindrical and surfaces 2-2-2 are spherical with center of curvature on the sagittal axis 16-1 and the planar surfaces 2-2-4 terminate the cylinder.

Surfaces in the second embodiment that can differ from the first embodiment are now described. Furrows 2-2-5 allow two of the four bearing rods welded, or otherwise fixedly attached, to plate 3-10, to pass without touching 2-2. The equivalent embodiments of lateral slider joint rods 10-2-5 are seen in the lateral slider joint raceway 10-2-2 of FIG. 36. FIG. 36 also illustrates an assembly of the lateral rotation cylinder with bearings 11-2 with the plate 10-2. After sliding the cylinder 11-2 into the raceway 10-2-2, the bearing-stop and joint-limit elements 10-2-4 can be press-fit, or otherwise fixed or positioned, into the ends of raceway 10-2-2. The length of 10-2-4 can determine the amount of travel permitted by 11-2 within the slider joint. FIG. 37 illustrates the same concept for the sagittal cylinder with the bearing-stop and joint-limit elements 3-2-4.

In a particular embodiment, cylindrical surface 2-2-6 does not touch 1-2-13 (FIG. 49), letting all the bearing elements bear the loads. Concave surface 2-2-8, 2-2-9, 2-2-12, and 2-2-13 can serve as bearing rod revolute raceways, as discussed above. The sides 2-2-7, and 2-2-11 of the revolute raceways can be cut planar. In a specific embodiment, the bearing elements of the subject invention can comprise hardened stainless steel.

In a further embodiment, on top of the sagittal revolute cylinder with bearings is a bearing support structure 2-2-3 which accommodates the sagittal slider bearing elements (FIG. 32): ball bearings 19-1, bearing separators 2-2-20, and bearing stops 2-2-10. The separators and stops can be welded or otherwise fixedly attached to block 2-2-3. Concave surface 2-2-28 and convex surface 2-2-29 of the bearing stops and separators can also conform to the lateral surfaces of block 2-2-3 and facilitate joining them to the block (FIG. 33). In a specific embodiment, projections 2-2-18 and 2-2-19 on the upper edge can be hardened steel raceway rods. In an alternative embodiment, the entire block 2-2-3 can be hardened stainless steel. These projections or rods can provide interlock surfaces with the sagittal bearing elements when the sagittal cylinder is joined to the spring platform plate 3-1. The discussion here is meant in no way to limit or restrict other means of implementing slider bearings, or any of the bearing elements in this invention. A person with skill in the art and having benefit of the subject application would be able to devise alternative bearing elements presently or prospectively known that can be utilized with the subject invention.

Such variations are considered to be within the scope of the subject invention, unless specifically taught otherwise.

In a further embodiment, planar surfaces 2-2-14, 2-2-15, 2-2-16, and 2-2-17 do not touch the lower planar surface of plate 3-1 in order to transfer all loads to the bearing elements as the sagittal slider joint between 3-2 and 2-2 operates. The planar surfaces 2-2-21 at either end of 2-2-3 can abut the ends of joint limit stops 3-2-4 at the two extreme slider positions. A similar description applies to corresponding elements of the lateral rotation cylinder with bearings.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

It should be understood that any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is submitted that it is within the purview of one skilled in the art to affect such feature, structure, or characteristic in connection with other ones of the embodiments.

The invention has been described herein in considerable detail, in order to comply with the Patent Statutes and to provide those skilled in the art with information needed to apply the novel principles, and to construct and use such specialized components as are required. However, it is to be understood that the invention can be carried out by specifically different equipment and devices, and that various modifications, both as to equipment details and operating procedures can be effected without departing from the scope of the invention itself. Further, it should be understood that, although the present invention has been described with reference to specific details of certain embodiments thereof, it is not intended that such details should be regarded as limitations upon the scope of the invention except as and to the extent that they are included in the accompanying claims.

I claim:

1. A prosthetic device for approximating spinal disc movement comprising:
 a spring-dashpot system having a superior end and an inferior end that includes,
 a superior segmented-wall inner core;
 an inferior segmented-wall inner core that engages with the superior segmented-wall inner core;
 one or more spring elements positioned around the segmented-wall inner cores,
 an inferior hydraulic cylinder wall positioned around the one or more spring elements; and
 a superior hydraulic cylinder wall that slidably engages telescopically with and is inseparable from the inferior hydraulic cylinder wall, such that the inferior and superior hydraulic cylinder walls confine the one or more spring elements;

a superior hydraulic cylinder plate having a top and bottom side, wherein the bottom side is fixedly attached to the superior end of the spring-dashpot system;
a first slide bearing block fixedly attached to the top side of the superior hydraulic cylinder plate;
a first rotation cylinder with a bearing raceway slidably affixed to the first slide bearing block;
an inferior hydraulic cylinder base having a top and bottom side, wherein the top side is fixedly attached to the inferior end of the spring-dashpot system;
a second slide bearing block fixedly attached to the bottom side of the inferior hydraulic cylinder base;
a second rotation cylinder with a bearing raceway slidably affixed to the second slide bearing block;
at least one means for attachment to a first vertebra being operably connected to the first rotation cylinder; and
at least one means for attachment to a second vertebra being operably connected to the second rotation cylinder, such that when said device is implanted in the spine with said attachment means engaged with a first and second vertebra, said device forms a kinematic chain of inseparably connected, articulating components between said first and second vertebra, wherein said device can provide at least one and up to three independent rotational degrees of freedom and at least one and up to three independent linear degrees of freedom.

2. The device, according to claim 1, further comprising at least one hydraulic portal.

3. The device, according to claim 1, further comprising at least one indented wall slot within the bottom side of the superior hydraulic cylinder plate and capable of cooperatively engaging with the inferior segmented-wall inner core.

4. The device, according to claim 3, further comprising at least one indented wall slot within the top side of the inferior hydraulic cylinder base and capable of cooperatively engaging with the superior segmented-wall inner core.

5. The device, according to claim 1, further comprising a toroidal belt at least partially surrounding the spring-dashpot system.

6. The device, according to claim 5, wherein the toroidal belt comprises a solid fiber-weave-embedded elastomer material.

7. The device, according to claim 6, wherein the toroidal belt further comprises an interior cushioning material.

8. The device, according to claim 7, wherein the cushioning material is air, compressible fluid, or hydrogel material.

9. The device, according to claim 5 wherein the toroidal belt is unconnected and can move freely around the spring-dashpot system.

10. The device, according to claim 5, wherein the toroidal belt is fixedly engaged with each of said means for attachment to the vertebrae and surrounds the functional elements.

11. The device, according to claim 5, further comprising an impermeable boot fixedly engaged with each of said means for attachment to the vertebrae and to the toroidal belt.

12. The device, according to claim 11, further comprising a biocompatible lubricant sealed within the boot.

13. The device, according to claim 11, wherein the boot comprises a fiber-reinforced elastomer matrix.

14. The device, according to claim 13, wherein the fiber-reinforcement comprises a spherical cross weave, such that the weave direction of the embedded fibers is diagonal relative to the central axis of the boot structure.

15. The device, according to claim 13, wherein the elastomer matrix is a flexible silicon.

16. The device, according to claim 11, wherein the toroidal belt comprises a solid fiber-weave-embedded elastomer material.

17. The device, according to claim 16, wherein the toroidal belt further comprises an interior cushioning material.

18. The device, according to claim 17, wherein the cushioning material is air, compressible fluid, or hydrogel material.

19. The device, according to claim 1, further comprising at least one bearing stop.

20. The device, according to claim 1, further comprising a locking key slot within at least one of the rotation cylinders for engaging with a locking key.

21. The device, according to claim 20, wherein the means for attachment to the vertebrae is affixed to at least one of the rotation cylinders utilizing the locking key.

22. The device, according to claim 1, wherein the one or more spring elements comprise one or more Belleville springs.

23. The device, according to claim 22, further comprising at least one matched-pair, or approximately matched-pair of Belleville springs.

24. The device, according to claim 23, further comprising at least one guard ring between matched, or approximately matched, Belleville spring pairs.

25. The device, according to claim 23, further comprising a raised lip on at least one of the Belleville springs in an approximately matched-pair.

26. The device, according to claim 1, further comprising at least one lock ring on both the inferior hydraulic cylinder wall and the superior hydraulic cylinder wall, wherein the lock rings render the cylinder walls inseparable.

27. The device, according to claim 1, further comprising at least one locking projection on at least one of the slide bearing blocks that, when engaged with the bearing raceway, renders the slide bearing block and rotating cylinder inseparable.

28. The device, according to claim 1, the device comprising one or more of titanium steel, titanium-carbide-coated stainless steel, bio-inert hardened stainless steel, polyurethane, polyurethane thermoplastic, cobalt-chromium-molybdenum alloy, plastic, ceramics, glass, or other materials or combinations thereof.

29. The device, according to claim 1, further comprising an impermeable boot fixedly engaged with each of said means for attachment to the vertebrae and surrounding the functional elements.

30. The device, according to claim 29, further comprising a biocompatible lubricant sealed within the boot.

31. The device, according to claim 29, wherein the boot comprises a fiber-reinforced elastomer matrix.

32. The device, according to claim 31, wherein the fiber-reinforcement comprises a spherical cross weave, such that the weave direction of the embedded fibers is diagonal relative to the central axis of the boot structure.

33. The device, according to claim 5, wherein the elastomer matrix is a flexible silicon.

* * * * *

UNITED STATES PATENT AND TRADEMARK OFFICE
CERTIFICATE OF CORRECTION

PATENT NO. : 7,927,375 B2  
APPLICATION NO. : 12/209363  
DATED : April 19, 2011  
INVENTOR(S) : Keith L. Doty Page 1 of 1

It is certified that error appears in the above-identified patent and that said Letters Patent is hereby corrected as shown below:

Column 2,  
Line 30, "Buttner-Jantz K.," should read --Buettner-Jantz, K.,--.

Column 4,  
Line 10, "LAR" should read --IAR--.

Column 11,  
Line 41, "are a mirror images" should read --are mirror images--.

Column 21,  
Line 5, "arc matched" should read --are matched--.

Column 32,  
Line 59, "according to claim 5" should read --according to claim 31--.

Signed and Sealed this  
Twenty-eighth Day of June, 2011

David J. Kappos  
*Director of the United States Patent and Trademark Office*